(12) United States Patent
Jahangir et al.

(10) Patent No.: US 8,318,764 B2
(45) Date of Patent: Nov. 27, 2012

(54) MACROCYCLIC INHIBITORS OF JAK

(75) Inventors: Alam Jahangir, San Jose, CA (US);
Stephen M Lynch, Westfield, NJ (US);
Michael Soth, Glen Rock, NJ (US);
Hanbiao Yang, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 124 days.

(21) Appl. No.: 12/884,243

(22) Filed: Sep. 17, 2010

(65) Prior Publication Data
US 2011/0071179 A1 Mar. 24, 2011

Related U.S. Application Data

(60) Provisional application No. 61/244,216, filed on Sep. 21, 2009, provisional application No. 61/372,969, filed on Aug. 12, 2010.

(51) Int. Cl.
*C07D 487/18* (2006.01)
*A61P 29/00* (2006.01)
*A61P 35/00* (2006.01)
*A61P 37/00* (2006.01)
*A61K 31/33* (2006.01)

(52) U.S. Cl. ......... 514/281; 514/287; 540/457; 540/460
(58) Field of Classification Search .................. 540/457, 540/460; 514/281, 287
See application file for complete search history.

(56) References Cited

U.S. PATENT DOCUMENTS
6,235,740 B1 5/2001 Barrish et al.

FOREIGN PATENT DOCUMENTS
| WO | 9945009 | 9/1999 |
| WO | 2005/030776 | 4/2005 |
| WO | 2008079965 | 7/2008 |
| WO | 2009152133 | 12/2009 |

OTHER PUBLICATIONS

Clark et al, Bioorganic & Medicinal Chemistry Letters, 17:5 (2007) 1250-1253 XP005888458.
International Search Report for PCT/EP2010/063682 dated Nov. 30, 2010.
Annu. Rev. Immunol. 16 (1998) pp. 293-322.
Leonard et al., (2000) J. Allergy Clin. Immunol. 105:877-888.
Oncogene 19 (2000) pp. 5652-5679.
Demoulin et al., (1996) Mol. Cell. Biol. 16:4710-6.
Jurlander et al. (1997) Blood 89:4146-52.
Kaneko et al. (1997) Clin. Exp. Immun. 109:185-193.
Nakamura et al., (1996) J. Biol. Chem. 271:19483-8.
Kudlacz et al., (2004) Am. J. Transplant 4:51-57.
Changelian (2003) Science 302:875-878.
Suzuki et al., (2000) Blood 96:2172-2180.
Malaviya et al., (1999) Biochem. Biophys. Res. Commun. 257:807-813.
Malaviya et al. (1999) J. Biol. Chem. 274:27028-27038.
Kirken (2001) Transpl. Proc. 33:3268-3270.
Muller-Ladner et al., (2000) J. Immunol. 164:3894-3901.
Trieu et al., (2000) Biochem. Biophys. Res. Commun. 267:22-25.
Sudbeck et al. (1999) Clin. Cancer Res. 5:1569-1582.
Nielsen et al. (1997) Prac. Natl. Acad. Sci. USA 94:6764-6769.
Yu et al. (1997) J. Immunol. 159:5206-5210.
Catlett-Falcone et al. (1999) Immunity 10:105-115.
J. Immunol. 168 (2002) pp. 2475-2482.
Blood 103 (2004) pp. 2009-2018.
J. Investig. Med. 44 (1996) pp. 304-311.
Curr. Opin. Cell Biol. 9 (1997) pp. 233-239.

*Primary Examiner* — Bruck Kifle
(74) *Attorney, Agent, or Firm* — George W. Johnston; Dennis P. Tramaloni; Jennifer L. Kisko

(57) ABSTRACT

The present invention relates to the use of novel macrocyclic compounds of Formula I,

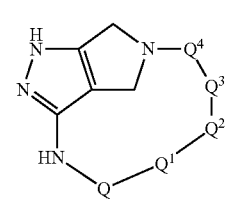

wherein the variables Q, $Q^1$, $Q^2$, $Q^3$, and $Q^4$ are defined as described herein, which inhibit JAK and are useful for the treatment of auto-immune and inflammatory diseases.

30 Claims, No Drawings

MACROCYCLIC INHIBITORS OF JAK

CROSS-REFERENCE TO RELATED APPLICATIONS

This application is entitled to the benefit of U.S. provisional patent application Ser. No. 61/244,216 filed on Sep. 21, 2009, and 61/372,969 filed on Aug. 12, 2010, the disclosures of which are incorporated herein by reference.

FIELD OF THE INVENTION

The present invention relates to the use of novel macrocyclic JAK inhibitors and selectively inhibit JAK3 and are useful for the treatment of auto-immune and inflammatory diseases.

BACKGROUND OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

The JAKs (JAnus Kinases) are a family of cytoplasmic protein tyrosine kinases including JAK1, JAK2, JAK3 and TYK2. Each of the JAKs is preferentially associated with the intracytoplasmic portion of discrete cytokine receptors (*Annu. Rev. Immunol.* 16 (1998), pp. 293-322). The JAKs are activated following ligand binding and initiate signaling by phosphorylating cytokine receptors that, per se, are devoid of intrinsic kinase activity. This phosphorylation creates docking sites on the receptors for other molecules known as STAT proteins (signal transducers and activators of transcription) and the phosphorylated JAKs bind various STAT proteins. STAT proteins, or STATs, are DNA binding proteins activated by phosphorylation of tyrosine residues, and function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Thus, the JAKs and STATs are components of multiple potentially intertwined signal-transduction pathways (*Onco-gene* 19 (2000), pp. 5662-5679), which indicates the difficulty of specifically targeting one element of the JAK-STAT pathway without interfering with other signal transduction pathways.

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important to lymphocyte differentiation, function and survival. JAK3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions which can benefit for inhibition of JAK3 are discussed in greater detail below.

However, in contrast to the relatively ubiquitous expression of JAK1, JAK2 and Tyk2, JAK3 has a more restricted and regulated expression. Whereas some JAKs (JAK1, JAK2, Tyk2) are used by a variety of cytokine receptors, JAK3 is used only by cytokines that contain a γc in their receptor. JAK3, therefore, plays a role in cytokine signaling for cytokines which receptor was shown to date to use the common gamma chain; IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-alpha. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

In particular, JAK3 has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad.

Sci. USA 94:6764-6769); and abnormal cell growth (Yu et al., (1997), J. Immunol. 159:5206-5210; Catlett-Falcone et al., (1999), Immunity 10:105-115).

JAK3 inhibitors are useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

Non-hematopoietic expression of JAK3 has also been reported, although the functional significance of this has yet to be clarified (J. Immunol. 168 (2002), pp. 2475-2482). Because bone marrow transplants for SCID are curative (Blood 103 (2004), pp. 2009-2018), it seems unlikely that JAK3 has essential non-redundant functions in other tissues or organs. Hence, in contrast with other targets of immunosuppressive drugs, the restricted distribution of JAK3 is appealing. Agents that act on molecular targets with expression limited to the immune system might lead to an optimal efficacy:toxicity ratio. Targeting JAK3 would, therefore, theoretically offer immune suppression where it is needed (i.e. on cells actively participating in immune responses) without resulting in any effects outside of these cell populations. Although defective immune responses have been described in various STAT$^{-/-}$ strains (J. Investig. Med. 44 (1996), pp. 304-311; Curr. Opin. Cell Biol. 9 (1997), pp. 233-239), the ubiquitous distribution of STATs and the fact that those molecules lack enzymatic activity that could be targeted with small-molecule inhibitors has contributed to their non-selection as key targets for immunosuppression.

In view of the numerous conditions that are contemplated to benefit by treatment involving modulation of the JAK pathways it is immediately apparent that new compounds that modulate JAK pathways and methods of using these compounds should provide substantial therapeutic benefits to a wide variety of patients. Provided herein are novel macrocyclic compounds for use in the treatment of conditions in which targeting of the JAK pathways or inhibition of JAK kinases, particularly JAK3, and are therapeutically useful for the treatment of auto-immune and inflammatory diseases.

SUMMARY OF THE INVENTION

The novel macrocyclic compounds provided herein selectively inhibit JAK3 and are useful for the treatment of auto-immune and inflammatory diseases. The compounds of the invention modulate the JAK pathways and are useful novel macrocyclic compounds for the treatment of auto-immune and inflammatory diseases, wherein preferred compounds selectively inhibit JAK3. For example, the compounds of the invention may inhibit JAK3, wherein preferred compounds are selective for JAK3 of the JAK kinases and are useful novel macrocyclic compounds for the treatment of auto-immune and inflammatory diseases. Furthermore, the compounds of the invention may inhibit JAK3 and JAK2, wherein preferred compounds are selective for JAK3 of the JAK kinases, and are useful novel macrocyclic compounds for the treatment of auto-immune and inflammatory diseases. Similarly, the compounds of the invention may inhibit JAK3 and JAK1, wherein preferred compounds are selective for JAK3 of the JAK kinases, and are useful novel macrocyclic compounds for the treatment of auto-immune and inflammatory diseases.

The application provides a compound of Formula I

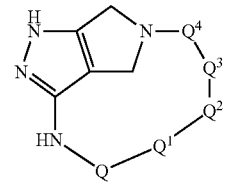

wherein:
Q is phenyl or heteroaryl, optionally substituted with one or more Q';
Q' is halogen, hydroxy, lower alkyl, lower haloalkyl, lower hydroxyalkyl, amino, lower alkoxy, or lower haloalkoxy;
$Q^1$ is O or $C(Q^{1'})_2$;
each $Q^{1'}$ is independently H, halogen, hydroxy, lower alkyl, lower haloalkyl, lower hydroxyalkyl, amino, lower alkoxy, or lower haloalkoxy;
$Q^2$ is $(C(Q^{2'})_2)_n$, $N(Q^{2''})$, or $C(Q^{2'})_2C(Q^{2'})_2$;
each $Q^{2'}$ is independently H, halogen, hydroxy, lower alkyl, lower haloalkyl, lower hydroxyalkyl, amino, lower alkoxy, or lower haloalkoxy;
or $Q^{2''}$ and $Q^{3'}$ together form a heterocyclic ring;
n is 2, 3, 4, or 5;
$Q^3$ is O, $N(Q^{3'})$, $C(Q^{3'})_2$, carbocyclyl, or heterocyclyl;
each $Q^{3'}$ is independently H, halogen, hydroxy, lower alkyl, lower haloalkyl, lower hydroxyalkyl, amino, lower alkoxy, phenyl, benzyl, or lower haloalkoxy;
or both $Q^{3'}$ together form a spirocyclic carbocyclic or heterocyclic ring; and
$Q^4$ is $C(=O)$ or $S(=O)_2$;
with the proviso that when $Q^2$ is $N(Q^{2''})$, then $Q^3$ is not $N(Q^{3'})$;
or a pharmaceutically acceptable salt thereof.

The application provides a method for treating an inflammatory or autoimmune condition comprising administering to a patient in need thereof a therapeutically effective amount of the compound of Formula I.

The application provides a pharmaceutical composition comprising the compound of Formula I, admixed with at least one pharmaceutically acceptable carrier, excipient or diluent.

DETAILED DESCRIPTION OF THE INVENTION

The application provides a compound of Formula I

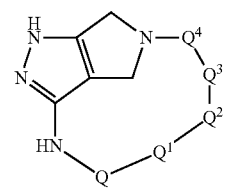

wherein:
Q is phenyl or heteroaryl, optionally substituted with one or more Q';
Q' is halogen, hydroxy, lower alkyl, lower haloalkyl, lower hydroxyalkyl, amino, lower alkoxy, or lower haloalkoxy;
$Q^1$ is O or $C(Q^{1'})_2$;
each $Q^{1'}$ is independently H, halogen, hydroxy, lower alkyl, lower haloalkyl, lower hydroxyalkyl, amino, lower alkoxy, or lower haloalkoxy;
$Q^2$ is $(C(Q^{2'})_2)_n$, $N(Q^{2''})$, or $C(Q^{2'})_2C(Q^{2'})_2$;

each Q²' is independently H, halogen, hydroxy, lower alkyl, lower haloalkyl, lower hydroxyalkyl, amino, lower alkoxy, or lower haloalkoxy;
  or Q²'' and Q³' together form a heterocyclic ring;
  n is 2, 3, 4, or 5;
Q³ is O, N(Q³'), C(Q³')$_2$, carbocyclyl, or heterocyclyl;
  each Q³' is independently H, halogen, hydroxy, lower alkyl, lower haloalkyl, lower hydroxyalkyl, amino, lower alkoxy, phenyl, benzyl, or lower haloalkoxy;
  or both Q³' together form a spirocyclic carbocyclic or heterocyclic ring; and
Q⁴ is C(=O) or S(=O)$_2$;
with the proviso that when Q² is N(Q²''), then Q³ is not N(Q³');
or a pharmaceutically acceptable salt thereof.
  In one variation of Formula I, Q is pyridine.
  In one variation of Formula I, Q⁴ is C(=O).
  In one variation of Formula I, Q⁴ is C(=O) and Q is pyridine.
  In one variation of Formula I, Q⁴ is S(=O)$_2$.
  In one variation of Formula I, Q⁴ is S(=O)$_2$ and Q is pyridine.
  In one variation of Formula I, Q³ is C(CH$_3$)$_2$ or C(CH$_3$)(CH$_2$CH$_3$).
  In one variation of Formula I, Q³ is C(CH$_3$)$_2$ or C(CH$_3$)(CH$_2$CH$_3$) and Q⁴ is C(=O).
  In one variation of Formula I, Q³ is C(CH$_3$)$_2$ or C(CH$_3$)(CH$_2$CH$_3$) and Q is pyridine.
  In one variation of Formula I, Q³ is C(CH$_3$)$_2$ or C(CH$_3$)(CH$_2$CH$_3$), Q is pyridine, and Q⁴ is C(=O).
  In one variation of Formula I, Q¹ is CH$_2$.
  In one variation of Formula I, Q¹ is CH$_2$ and Q⁴ is C(=O).
  In one variation of Formula I, Q¹ is CH$_2$ and Q is pyridine.
  In one variation of Formula I, Q¹ is CH$_2$, Q⁴ is C(=O), and Q is pyridine.
  In one variation of Formula I, Q¹ is CH$_2$, Q³ is C(CH$_3$)$_2$ or C(CH$_3$)(CH$_2$CH$_3$), Q is pyridine, and Q⁴ is C(=O).
  In one variation of Formula I, Q² is C(CH$_2$)$_n$.
  In one variation of Formula I, Q² is C(Q²')$_2$C(Q²')$_2$;
  In one variation of Formula I, Q² is C(CH$_2$)$_n$ and Q¹ is CH$_2$.
  In one variation of Formula I, Q² is C(CH$_2$)$_n$ and Q is pyridine.
  In one variation of Formula I, Q² is C(CH$_2$)$_n$, Q¹ is CH$_2$, and Q is pyridine.
  In one variation of Formula I, Q² is C(CH$_2$)$_n$, Q⁴ is C(=O), Q¹ is CH$_2$, and Q is pyridine.
  In one variation of Formula I, Q² is C(CH$_2$)$_n$, Q³ is C(CH$_3$)$_2$ or C(CH$_3$)(CH$_2$CH$_3$), Q⁴ is C(=O), Q¹ is CH$_2$, and Q is pyridine.
  In one variation of Formula I, n is 2.
  In one variation of Formula I, n is 3.
  In one variation of Formula I, n is 4.
  In one variation of Formula I, n is 2, Q² is C(CH$_2$)$_n$, Q³ is C(CH$_3$)$_2$ or C(CH$_3$)(CH$_2$CH$_3$), Q⁴ is C(=O), Q¹ is CH$_2$, and Q is pyridine.
  In one variation of Formula I, n is 3, Q² is C(CH$_2$)$_n$, Q³ is C(CH$_3$)$_2$ or C(CH$_3$)(CH$_2$CH$_3$), Q⁴ is C(=O), Q¹ is CH$_2$, and Q is pyridine.
  In one variation of Formula I, n is 4, Q² is C(CH$_2$)$_n$, Q³ is C(CH$_3$)$_2$ or C(CH$_3$)(CH$_2$CH$_3$), Q⁴ is C(=O), Q¹ is CH$_2$, and Q is pyridine.
  In one variation of Formula I, Q¹ is O.
  In one variation of Formula I, Q¹ is O and Q is pyridine.
  In one variation of Formula I, Q¹ is O, Q is pyridine, and Q⁴ is C(=O).
  In one variation of Formula I, Q¹ is O, Q³ is C(CH$_3$)$_2$ or C(CH$_3$)(CH$_2$CH$_3$), Q is pyridine, and Q⁴ is C(=O).
  In one variation of Formula I, Q¹ is O, Q² is C(CH$_2$)$_n$, Q³ is C(CH$_3$)$_2$ or C(CH$_3$)(CH$_2$CH$_3$), Q is pyridine, and Q⁴ is C(=O).
  In one variation of Formula I, Q¹ is O, n is 2, Q² is C(CH$_2$)$_n$, Q³ is C(CH$_3$)$_2$ or C(CH$_3$)(CH$_2$CH$_3$), Q is pyridine, and Q⁴ is C(=O).
  In one variation of Formula I, Q¹ is O, n is 3, Q² is C(CH$_2$)$_n$, Q³ is C(CH$_3$)$_2$ or C(CH$_3$)(CH$_2$CH$_3$), Q is pyridine, and Q⁴ is C(=O).
  In one variation of Formula I, Q¹ is O, n is 4, Q² is C(CH$_2$)$_n$, Q³ is C(CH$_3$)$_2$ or C(CH$_3$)(CH$_2$CH$_3$), Q is pyridine, and Q⁴ is C(=O).
  The application provides a compound of Formula II

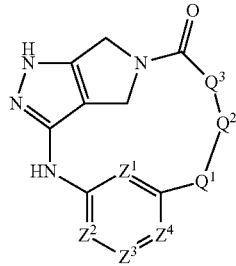

wherein:
each of Z¹, Z², Z³, and Z⁴ are independently C(Z') or N;
  each Z' is independently H, halogen, hydroxy, lower alkyl, lower haloalkyl, lower hydroxyalkyl, amino, lower alkoxy, or lower haloalkoxy;
Q¹ is O or C(Q¹')$_2$;
  each Q¹' is independently H, halogen, hydroxy, lower alkyl, lower haloalkyl, lower hydroxyalkyl, amino, lower alkoxy, or lower haloalkoxy;
Q² is (C(Q²')$_2$)$_n$, N(Q²''), or C(Q²')$_2$C(Q²')$_2$;
  each Q²' is independently H, halogen, hydroxy, lower alkyl, lower haloalkyl, lower hydroxyalkyl, amino, lower alkoxy, or lower haloalkoxy;
  or Q²'' and Q³' together form a heterocyclic ring;
  n is 2, 3, 4, or 5;
Q³ is O, N(Q³'), C(Q³')$_2$, carbocyclyl, or heterocyclyl;
  each Q³' is independently H, halogen, hydroxy, lower alkyl, lower haloalkyl, lower hydroxyalkyl, amino, lower alkoxy, phenyl, benzyl, or lower haloalkoxy;
  or both Q³' together form a spirocyclic carbocyclic or heterocyclic ring; and
with the proviso that when Q² is N(Q²''), then Q³ is not N(Q³');
or a pharmaceutically acceptable salt thereof.
  In one variation of Formula II, Z¹ is N, Z² is CH, Z³ is CH, and Z⁴ is CH.
  In one variation of Formula II, Q³ is C(CH$_3$)$_2$ or C(CH$_3$)(CH$_2$CH$_3$).
  In one variation of Formula II, Q³ is C(CH$_3$)$_2$ or C(CH$_3$)(CH$_2$CH$_3$), Z¹ is N, Z² is CH, Z³ is CH, and Z⁴ is CH.
  In one variation of Formula II, Q¹ is CH$_2$.
  In one variation of Formula II, Q¹ is CH$_2$, Z¹ is N, Z² is CH, Z³ is CH, and Z⁴ is CH.
  In one variation of Formula II, Q³ is C(CH$_3$)$_2$ or C(CH$_3$)(CH$_2$CH$_3$), Q¹ is CH$_2$, Z¹ is N, Z² is CH, Z³ is CH, and Z⁴ is CH.
  In one variation of Formula II, Q² is C(CH$_2$)$_n$.
  In one variation of Formula II, Q² is C(Q²')$_2$C(Q²')$_2$;
  In one variation of Formula II, Q² is C(CH$_2$)$_n$ and Q¹ is CH$_2$.

In one variation of Formula II, $Q^2$ is $C(CH_2)_n$, $Q^3$ is $C(CH_3)_2$ or $C(CH_3)(CH_2CH_3)$, and $Q^1$ is $CH_2$.

In one variation of Formula II, $Q^2$ is $C(CH_2)_n$, $Q^3$ is $C(CH_3)_2$ or $C(CH_3)(CH_2CH_3)$, $Q^1$ is $CH_2$, $Z^1$ is N, $Z^2$ is CH, $Z^3$ is CH, and $Z^4$ is CH.

In one variation of Formula II, n is 2.
In one variation of Formula II, n is 3.
In one variation of Formula II, n is 4.
In one variation of Formula II, n is 2, $Q^2$ is $C(CH_2)_n$, $Q^3$ is $C(CH_3)_2$ or $C(CH_3)(CH_2CH_3)$, $Q^1$ is $CH_2$, $Z^1$ is N, $Z^2$ is CH, $Z^3$ is CH, and $Z^4$ is CH.
In one variation of Formula II, n is 3, $Q^2$ is $C(CH_2)_n$, $Q^3$ is $C(CH_3)_2$ or $C(CH_3)(CH_2CH_3)$, $Q^1$ is $CH_2$, $Z^1$ is N, $Z^2$ is CH, $Z^3$ is CH, and $Z^4$ is CH.
In one variation of Formula II, n is 4, $Q^2$ is $C(CH_2)_n$, $Q^3$ is $C(CH_3)_2$ or $C(CH_3)(CH_2CH_3)$, $Q^1$ is $CH_2$, $Z^1$ is N, $Z^2$ is CH, $Z^3$ is CH, and $Z^4$ is CH.
In one variation of Formula II, $Q^1$ is O.
In one variation of Formula II, $Q^1$ is O and $Q^2$ is $C(CH_2)_n$.
In one variation of Formula II, $Q^1$ is O, $Q^3$ is $C(CH_3)_2$ or $C(CH_3)(CH_2CH_3)$, and $Q^2$ is $C(CH_2)_n$.
In one variation of Formula II, $Q^1$ is O and $Z^1$ is N, $Z^2$ is CH, $Z^3$ is CH, and $Z^4$ is CH.
In one variation of Formula II, $Q^1$ is O, $Q^3$ is $C(CH_3)_2$ or $C(CH_3)(CH_2CH_3)$, $Q^2$ is $C(CH_2)_n$, and $Z^1$ is N, $Z^2$ is CH, $Z^3$ is CH, and $Z^4$ is CH.
In one variation of Formula II, $Q^2$ is $C(CH_2)_n$.
In one variation of Formula II, $Q^2$ is $C(CH_2)_n$ and $Q^1$ is O.
In one variation of Formula II, $Q^3$ is $C(CH_3)_2$ or $C(CH_3)(CH_2CH_3)$, $Q^2$ is $C(CH_2)_n$ and $Q^1$ is O.
In one variation of Formula II, $Z^1$ is N, $Z^2$ is CH, $Z^3$ is CH, and $Z^4$ is CH, $Q^3$ is $C(CH_3)_2$ or $C(CH_3)(CH_2CH_3)$, $Q^2$ is $C(CH_2)_n$ and $Q^1$ is O.
In one variation of Formula II, n is 3.
In one variation of Formula II, n is 4.
In one variation of Formula II, n is 3, $Z^1$ is N, $Z^2$ is CH, $Z^3$ is CH, and $Z^4$ is CH, $Q^3$ is $C(CH_3)_2$ or $C(CH_3)(CH_2CH_3)$, $Q^2$ is $C(CH_2)_n$ and $Q^1$ is O.
In one variation of Formula II, n is 4, $Z^1$ is N, $Z^2$ is CH, $Z^3$ is CH, and $Z^4$ is CH, $Q^3$ is $C(CH_3)_2$ or $C(CH_3)(CH_2CH_3)$, $Q^2$ is $C(CH_2)_n$ and $Q^1$ is O.

The application provides a compound selected from the group consisting of:

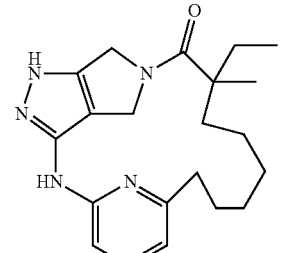

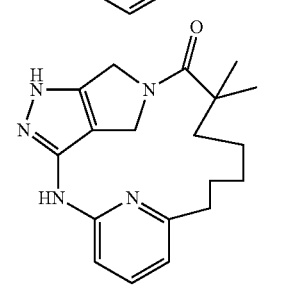

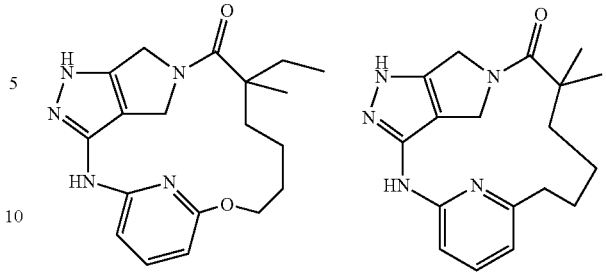

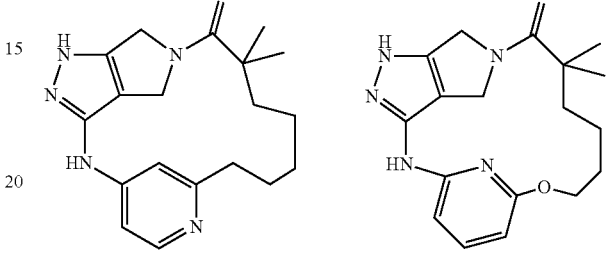

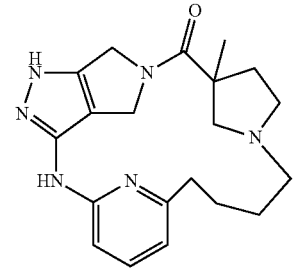

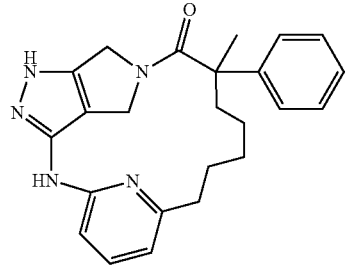

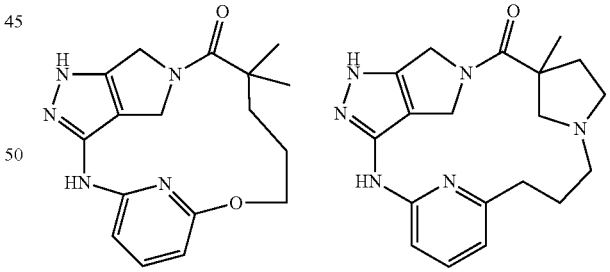

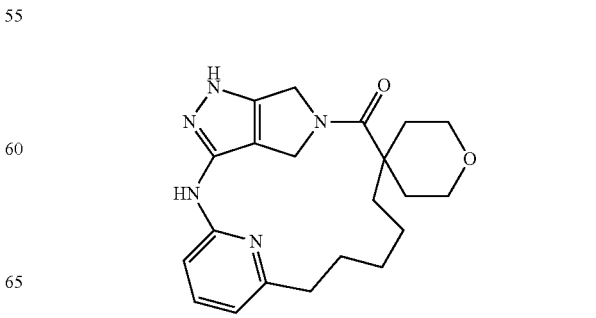

-continued

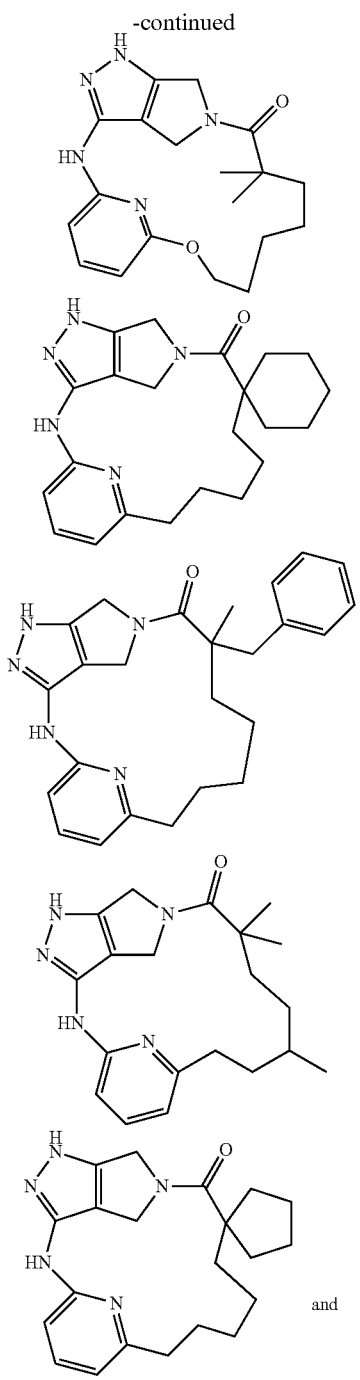

and

The application provides a method for treating an inflammatory or autoimmune condition comprising administering to a patient in need thereof a therapeutically effective amount of the compound of Formula I or Formula II.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I or Formula II.

The application provides a method for inhibiting T-cell proliferative disorder comprising administering to a patient in need thereof a therapeutically effective amount of the compound of Formula I or Formula II.

The application provides a method for inhibiting T-cell proliferative disorder comprising administering to a patient in need thereof a therapeutically effective amount of the compound of Formula I or Formula II.

The application provides the above method, wherein the proliferative disorder is cancer.

The application provides a method for treating a B-cell proliferative disorder comprising administering to a patient in need thereof a therapeutically effective amount of the compound of Formula I or Formula II.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I or Formula II.

The application provides a method for preventing or treating all forms of organ rejection, including acute allograft or xenograft rejection and chronic allograft or xenograft rejection, of vascularized or non-vascularized transplants, comprising administering to a patient in need thereof the compound of Formula I or Formula II.

The application provides a method for inhibiting JAK3 activity comprising administering the compound of Formula I or Formula II, wherein the compound exhibits an $IC_{50}$ of 50 micromolar or less in an in vitro biochemical assay of JAK3 activity.

The application provides the above method, wherein the compound exhibits an $IC_{50}$ of 100 nanomolar or less in an in vitro biochemical assay of JAK3 activity.

The application provides the above method, wherein the compound exhibits an $IC_{50}$ of 10 nanomolar or less in an in vitro biochemical assay of JAK3 activity.

The application provides a method for treating an inflammatory condition comprising co-administering to a patient in need thereof a therapeutically effective amount of an anti-inflammatory compound in combination with the compound of Formula I or Formula II.

The application provides a method for treating an immune disorder comprising co-administering to a patient in need thereof a therapeutically effective amount of an immunosuppressant compound in combination with the compound of Formula I or Formula II.

The application provides a pharmaceutical composition comprising the compound of Formula I or Formula II, admixed with at least one pharmaceutically acceptable carrier, excipient or diluent.

The application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides a use of the compound of Formula I or Formula II in the manufacture of a medicament for the treatment of an inflammatory disorder.

The application provides a use of the compound of Formula I or Formula II in the manufacture of a medicament for the treatment of an autoimmune disorder.

The application provides a method for treating rheumatoid arthritis comprising administering to a patient in need thereof a therapeutically effective amount of the compound of Formula I or Formula II.

The application provides a method for treating asthma comprising administering to a patient in need thereof a therapeutically effective amount of the compound of Formula I or Formula II.

The application provides a compound, method, or composition as described herein.

The application provides a compound of Formula I'

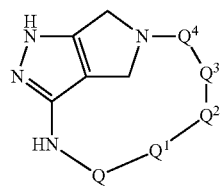

wherein:
Q is phenyl or heteroaryl, optionally substituted with one or more Q';
Q' is halogen, hydroxy, lower alkyl, lower haloalkyl, lower hydroxyalkyl, amino, lower alkoxy, or lower haloalkoxy;
$Q^1$ is O or $C(Q^{1'})_2$;
each $Q^{1'}$ is independently H, halogen, hydroxy, lower alkyl, lower haloalkyl, lower hydroxyalkyl, amino, lower alkoxy, or lower haloalkoxy;
$Q_2$ is $(C(Q^{2'})_2)_n$, $N(Q^{2''})$, or $C(Q^{2'})_2C(Q^{2'})_2$;
each $Q^{2'}$ is independently H, halogen, hydroxy, lower alkyl, lower haloalkyl, lower hydroxyalkyl, amino, lower alkoxy, or lower haloalkoxy;
or $Q^{2''}$ and $Q^{3'}$ together form a heterocyclic ring;
n is 2, 3 or 4;
$Q^3$ is O, $N(Q^{3'})$, or $C(Q^{3'})_2$;
each $Q^{3'}$ is independently H, halogen, hydroxy, lower alkyl, lower haloalkyl, lower hydroxyalkyl, amino, lower alkoxy, or lower haloalkoxy;
or both $Q^{3'}$ together form a spirocyclic carbocyclic or heterocyclic ring; and
$Q^4$ is C(=O) or $S(=O)_2$;
with the proviso that when $Q^2$ is $N(Q^{2''})$, then $Q^3$ is not $N(Q^{3'})$;
or a pharmaceutically acceptable salt thereof.

In one variation of Formula I', Q is pyridine.
In one variation of Formula I', $Q^4$ is C(=O).
In one variation of Formula I', $Q^4$ is C(=O) and Q is pyridine.
In one variation of Formula I', $Q^4$ is $S(=O)_2$.
In one variation of Formula I', $Q^4$ is $S(=O)_2$ and Q is pyridine.
In one variation of Formula I', $Q^3$ is $C(CH_3)_2$ or $C(CH_3)(CH_2CH_3)$.
In one variation of Formula I', $Q^3$ is $C(CH_3)_2$ or $C(CH_3)(CH_2CH_3)$ and $Q^4$ is C(=O).
In one variation of Formula I', $Q^3$ is $C(CH_3)_2$ or $C(CH_3)(CH_2CH_3)$ and Q is pyridine.
In one variation of Formula I', $Q^3$ is $C(CH_3)_2$ or $C(CH_3)(CH_2CH_3)$, Q is pyridine, and $Q^4$ is C(=O).
In one variation of Formula I', $Q^1$ is $CH_2$.
In one variation of Formula I', $Q^1$ is $CH_2$ and $Q^4$ is C(=O).
In one variation of Formula I', $Q^1$ is $CH_2$ and Q is pyridine.
In one variation of Formula I', $Q^1$ is $CH_2$, $Q^4$ is C(=O), and Q is pyridine.
In one variation of Formula I', $Q^1$ is $CH_2$, $Q^3$ is $C(CH_3)_2$ or $C(CH_3)(CH_2CH_3)$, Q is pyridine, and $Q^4$ is C(=O).
In one variation of Formula I', $Q^2$ is $C(CH_2)_n$.
In one variation of Formula I', $Q^2$ is $C(Q^{2'})_2C(Q^{2'})_2$;
In one variation of Formula I', $Q^2$ is $C(CH_2)_n$ and $Q^1$ is $CH_2$.
In one variation of Formula I', $Q^2$ is $C(CH_2)_n$ and Q is pyridine.
In one variation of Formula I', $Q^2$ is $C(CH_2)_n$, $Q^1$ is $CH_2$, and Q is pyridine.
In one variation of Formula I', $Q^2$ is $C(CH_2)_n$, $Q^4$ is C(=O), $Q^1$ is $CH_2$, and Q is pyridine.
In one variation of Formula I', $Q^2$ is $C(CH_2)_n$, $Q^3$ is $C(CH_3)_2$ or $C(CH_3)(CH_2CH_3)$, $Q^4$ is C(=O), $Q^1$ is $CH_2$, and Q is pyridine.
In one variation of Formula I', n is 2.
In one variation of Formula I', n is 3.
In one variation of Formula I', n is 4.
In one variation of Formula I', n is 2, $Q^2$ is $C(CH_2)_n$, $Q^3$ is $C(CH_3)_2$ or $C(CH_3)(CH_2CH_3)$, $Q^4$ is C(=O), $Q^1$ is $CH_2$, and Q is pyridine.
In one variation of Formula I', n is 3, $Q^2$ is $C(CH_2)_n$, $Q^3$ is $C(CH_3)_2$ or $C(CH_3)(CH_2CH_3)$, $Q^4$ is C(=O), $Q^1$ is $CH_2$, and Q is pyridine.
In one variation of Formula I', n is 4, $Q^2$ is $C(CH_2)_n$, $Q^3$ is $C(CH_3)_2$ or $C(CH_3)(CH_2CH_3)$, $Q^4$ is C(=O), $Q^1$ is $CH_2$, and Q is pyridine.
In one variation of Formula I', $Q^1$ is O.
In one variation of Formula I', $Q^1$ is O and Q is pyridine.
In one variation of Formula I', $Q^1$ is O, Q is pyridine, and $Q^4$ is C(=O).
In one variation of Formula I', $Q^1$ is O, $Q^3$ is $C(CH_3)_2$ or $C(CH_3)(CH_2CH_3)$, Q is pyridine, and $Q^4$ is C(=O).
In one variation of Formula I', $Q^1$ is O, $Q^2$ is $C(CH_2)_n$, $Q^3$ is $C(CH_3)_2$ or $C(CH_3)(CH_2CH_3)$, Q is pyridine, and $Q^4$ is C(=O).
In one variation of Formula I', $Q^1$ is O, n is 2, $Q^2$ is $C(CH_2)_n$, $Q^3$ is $C(CH_3)_2$ or $C(CH_3)(CH_2CH_3)$, Q is pyridine, and $Q^4$ is C(=O).
In one variation of Formula I', $Q^1$ is O, n is 3, $Q^2$ is $C(CH_2)_n$, $Q^3$ is $C(CH_3)_2$ or $C(CH_3)(CH_2CH_3)$, Q is pyridine, and $Q^4$ is C(=O).
In one variation of Formula I', $Q^1$ is O, n is 4, $Q^2$ is $C(CH_2)_n$, $Q^3$ is $C(CH_3)_2$ or $C(CH_3)(CH_2CH_3)$, Q is pyridine, and $Q^4$ is C(=O).

The application provides a compound of Formula II'

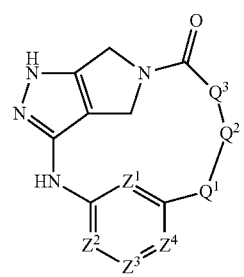

wherein:
each of $Z^1$, $Z^2$, $Z^3$, and $Z^4$ are independently C(Z') or N;
each Z' is independently H, halogen, hydroxy, lower alkyl, lower haloalkyl, lower hydroxyalkyl, amino, lower alkoxy, or lower haloalkoxy;

$Q^1$ is O or $C(Q^{1'})_2$;

each $Q^{1'}$ is independently H, halogen, hydroxy, lower alkyl, lower haloalkyl, lower hydroxyalkyl, amino, lower alkoxy, or lower haloalkoxy;

$Q^2$ is $(C(Q^{2'})_2)_n$, $N(Q^{2''})$, or $C(Q^{2'})_2C(Q^{2'})_2$;

each $Q^{2'}$ is independently H, halogen, hydroxy, lower alkyl, lower haloalkyl, lower hydroxyalkyl, amino, lower alkoxy, or lower haloalkoxy;

or $Q^{2''}$ and $Q^{3'}$ together form a heterocyclic ring;

n is 2, 3 or 4;

$Q^3$ is O, $N(Q^3)$, or $C(Q^{3'})_2$;

each $Q^{3'}$ is independently H, halogen, hydroxy, lower alkyl, lower haloalkyl, lower hydroxyalkyl, amino, lower alkoxy, or lower haloalkoxy;

or both $Q^{3'}$ together form a spirocyclic ring; and with the proviso that when $Q^2$ is $N(Q^{2''})$, then $Q^3$ is not $N(Q^{3'})$;

or a pharmaceutically acceptable salt thereof.

In one variation of Formula II', $Z^1$ is N, $Z^2$ is CH, $Z^3$ is CH, and $Z^4$ is CH.

In one variation of Formula II', $Q^3$ is $C(CH_3)_2$ or $C(CH_3)(CH_2CH_3)$.

In one variation of Formula II', $Q^3$ is $C(CH_3)_2$ or $C(CH_3)(CH_2CH_3)$, $Z^1$ is N, $Z^2$ is CH, $Z^3$ is CH, and $Z^4$ is CH.

In one variation of Formula II', $Q^1$ is $CH_2$.

In one variation of Formula II', $Q^1$ is $CH_2$, $Z^1$ is N, $Z^2$ is CH, $Z^3$ is CH, and $Z^4$ is CH.

In one variation of Formula II', $Q^3$ is $C(CH_3)_2$ or $C(CH_3)(CH_2CH_3)$, $Q^1$ is $CH_2$, $Z^1$ is N, $Z^2$ is CH, $Z^3$ is CH, and $Z^4$ is CH.

In one variation of Formula II', $Q^2$ is $C(CH_2)_n$.

In one variation of Formula II', $Q^2$ is $C(Q^{2'})_2C(Q^{2'})_2$;

In one variation of Formula II', $Q^2$ is $C(CH_2)_n$ and $Q^1$ is $CH_2$.

In one variation of Formula II', $Q^2$ is $C(CH_2)_n$, $Q^3$ is $C(CH_3)_2$ or $C(CH_3)(CH_2CH_3)$, and $Q^1$ is $CH_2$.

In one variation of Formula II', $Q^2$ is $C(CH_2)_n$, $Q^3$ is $C(CH_3)_2$ or $C(CH_3)(CH_2CH_3)$, $Q^1$ is $CH_2$, $Z^1$ is N, $Z^2$ is CH, $Z^3$ is CH, and $Z^4$ is CH.

In one variation of Formula II', n is 2.

In one variation of Formula II', n is 3.

In one variation of Formula II', n is 4.

In one variation of Formula II', n is 2, $Q^2$ is $C(CH_2)_n$, $Q^3$ is $C(CH_3)_2$ or $C(CH_3)(CH_2CH_3)$, $Q^1$ is $CH_2$, $Z^1$ is N, $Z^2$ is CH, $Z^3$ is CH, and $Z^4$ is CH.

In one variation of Formula II', n is 3, $Q^2$ is $C(CH_2)_n$, $Q^3$ is $C(CH_3)_2$ or $C(CH_3)(CH_2CH_3)$, $Q^1$ is $CH_2$, $Z^1$ is N, $Z^2$ is CH, $Z^3$ is CH, and $Z^4$ is CH.

In one variation of Formula II', n is 4, $Q^2$ is $C(CH_2)_n$, $Q^3$ is $C(CH_3)_2$ or $C(CH_3)(CH_2CH_3)$, $Q^1$ is $CH_2$, $Z^1$ is N, $Z^2$ is CH, $Z^3$ is CH, and $Z^4$ is CH.

In one variation of Formula II', $Q^1$ is O.

In one variation of Formula II', $Q^1$ is O and $Q^2$ is $C(CH_2)_n$.

In one variation of Formula II', $Q^1$ is O, $Q^3$ is $C(CH_3)_2$ or $C(CH_3)(CH_2CH_3)$, and $Q^2$ is $C(CH_2)$.

In one variation of Formula II', $Q^1$ is O and $Z^1$ is N, $Z^2$ is CH, $Z^3$ is CH, and $Z^4$ is CH.

In one variation of Formula II', $Q^1$ is O, $Q^3$ is $C(CH_3)_2$ or $C(CH_3)(CH_2CH_3)$, $Q^2$ is $C(CH_2)_n$, and $Z^1$ is N, $Z^2$ is CH, $Z^3$ is CH, and $Z^4$ is CH.

In one variation of Formula II', $Q^2$ is $C(CH_2)_n$.

In one variation of Formula II', $Q^2$ is $C(CH_2)_n$ and $Q^1$ is O.

In one variation of Formula II', $Q^3$ is $C(CH_3)_2$ or $C(CH_3)(CH_2CH_3)$, $Q^2$ is $C(CH_2)_n$ and $Q^1$ is O.

In one variation of Formula II', $Z^1$ is N, $Z^2$ is CH, $Z^3$ is CH, and $Z^4$ is CH, $Q^3$ is $C(CH_3)_2$ or $C(CH_3)(CH_2CH_3)$, $Q^2$ is $C(CH_2)_n$ and $Q^1$ is O.

In one variation of Formula II', n is 3.

In one variation of Formula II', n is 4.

In one variation of Formula II', n is 3, $Z^1$ is N, $Z^2$ is CH, $Z^3$ is CH, and $Z^4$ is CH, $Q^3$ is $C(CH_3)_2$ or $C(CH_3)(CH_2CH_3)$, $Q^2$ is $C(CH_2)_n$ and $Q^1$ is O.

In one variation of Formula II', n is 4, $Z^1$ is N, $Z^2$ is CH, $Z^3$ is CH, and $Z^4$ is CH, $Q^3$ is $C(CH_3)_2$ or $C(CH_3)(CH_2CH_3)$, $Q^2$ is $C(CH_2)_n$ and $Q^1$ is O.

The application provides a compound selected from the group consisting of:

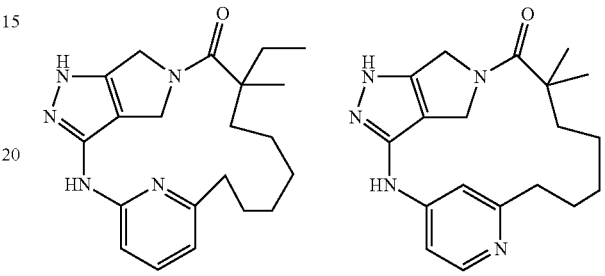

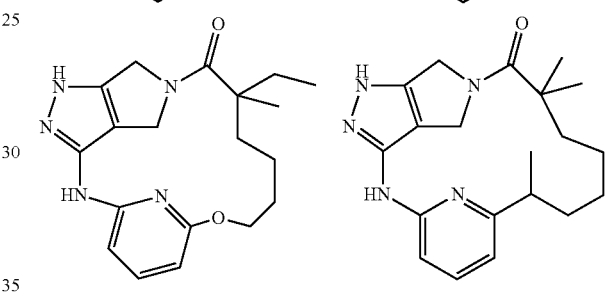

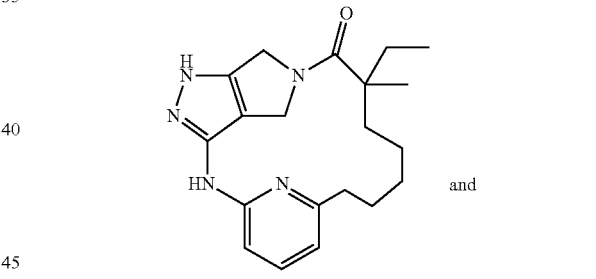

and

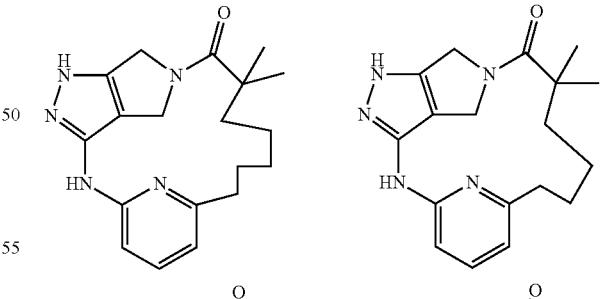

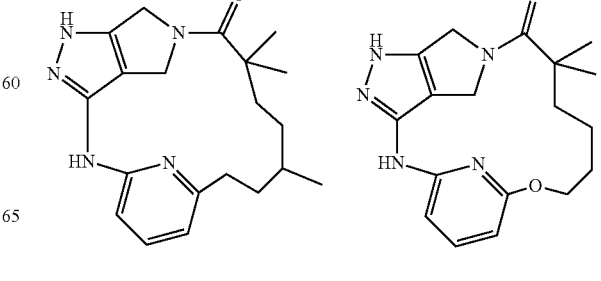

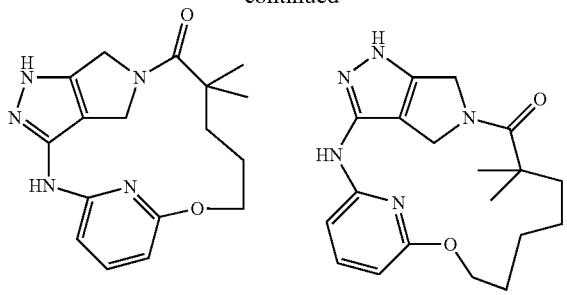

The application provides a method for treating an inflammatory or autoimmune condition comprising administering to a patient in need thereof a therapeutically effective amount of the compound of Formula I' or Formula II'.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I' or Formula II'.

The application provides a method for inhibiting T-cell proliferative disorder comprising administering to a patient in need thereof a therapeutically effective amount of the compound of Formula I' or Formula II'.

The application provides a method for inhibiting T-cell proliferative disorder comprising administering to a patient in need thereof a therapeutically effective amount of the compound of Formula I' or Formula II'.

The application provides the above method, wherein the proliferative disorder is cancer.

The application provides a method for treating a B-cell proliferative disorder comprising administering to a patient in need thereof a therapeutically effective amount of the compound of Formula I' or Formula II'.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I' or Formula II'.

The application provides a method for preventing or treating all forms of organ rejection, including acute allograft or xenograft rejection and chronic allograft or xenograft rejection, of vascularized or non-vascularized transplants, comprising administering to a patient in need thereof the compound of Formula I' or Formula II'.

The application provides a method for inhibiting JAK3 activity comprising administering the compound of Formula I' or Formula II', wherein the compound exhibits an $IC_{50}$ of 50 micromolar or less in an in vitro biochemical assay of JAK3 activity.

The application provides the above method, wherein the compound exhibits an $IC_{50}$ of 100 nanomolar or less in an in vitro biochemical assay of JAK3 activity.

The application provides the above method, wherein the compound exhibits an $IC_{50}$ of 10 nanomolar or less in an in vitro biochemical assay of JAK3 activity.

The application provides a method for treating an inflammatory condition comprising co-administering to a patient in need thereof a therapeutically effective amount of an anti-inflammatory compound in combination with the compound of Formula I' or Formula II'.

The application provides a method for treating an immune disorder comprising co-administering to a patient in need thereof a therapeutically effective amount of an immunosuppressant compound in combination with the compound of Formula I' or Formula II'.

The application provides a pharmaceutical composition comprising the compound of Formula I' or Formula II', admixed with at least one pharmaceutically acceptable carrier, excipient or diluent.

The application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides a use of the compound of Formula I' or Formula II' in the manufacture of a medicament for the treatment of an inflammatory disorder.

The application provides a use of the compound of Formula I' or Formula II' in the manufacture of a medicament for the treatment of an autoimmune disorder.

The application provides a method for treating rheumatoid arthritis comprising administering to a patient in need thereof a therapeutically effective amount of the compound of Formula I' or Formula II'.

The application provides a method for treating asthma comprising administering to a patient in need thereof a therapeutically effective amount of the compound of Formula I' or Formula II'.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R, R', or Q) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:
MeC(=O)OR$^4$ wherein

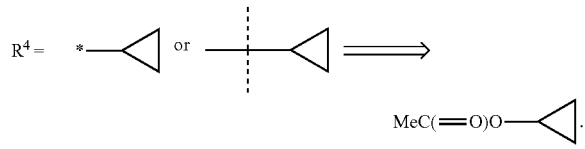

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "come together to form a bicyclic ring system" as used herein means join to form a bicyclic ring system, wherein each ring may be made up of either 4-7 carbon atoms or 4-7 carbon and heteroatoms, and may be saturated or unsaturated.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The definitions described herein may be appended to form chemically-relevant combinations, such as "heteroalkylaryl," "haloalkylheteroaryl," "arylalkylheterocyclyl," "alkylcarbonyl," "alkoxyalkyl," "cycloalkylalkyl" and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

Compounds of formula I may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term C$_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "C$_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl", "aryl alkyl", or "aralkyl" are interpreted similarly except R' is an aryl radical. The terms "heteroaryl alkyl" or "heteroarylalkyl" are interpreted similarly except R' is optionally an aryl or a heteroaryl radical.

The term "haloalkyl" as used herein denotes a unbranched or branched chain alkyl group as defined above wherein 1, 2, 3 or more hydrogen atoms are substituted by a halogen. The term "lower haloalkyl" denotes a straight or branched chain hydrocarbon residue containing 1 to 6 carbon atoms, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "hydroxyalkyl" as used herein denotes an alkyl radical as herein defined wherein one to three hydrogen atoms on different carbon atoms is/are replaced by hydroxyl groups.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "halogen" or "halo" as used herein means fluorine, chlorine, bromine, or iodine.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocycloalkyl", "heterocyclyl" or "heterocycle" as used herein denotes a monovalent saturated cyclic radical, consisting of one or more rings, preferably one to two rings, of three to eight atoms per ring, incorporating one or more ring carbon atoms and one or more ring heteroatoms (chosen from N, O or $S(=O)_{0-2}$), wherein the point of attachment can be through either a carbon atom or a heteroatom, and which can optionally be independently substituted with one or more, preferably one or two or three substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The phrase "organ rejection" includes acute allograft or xenograft rejection and chronic allograft or xenograft rejection in the setting of vascularized and/or non-vascularized (e.g. bone marrow, pancreatic islet cells) transplants.

Commonly used abbreviations include: acetyl (Ac), azobis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), trimethylsilanyl-ethoxymethyl (SEM), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me₃Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts exemplified compounds according to Formula I.

TABLE I

| COMPOUND | STRUCTURE |
| --- | --- |
| I-1 | |
| I-2 | |
| I-3 | 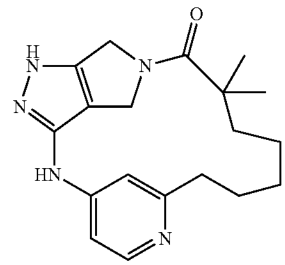 |
| I-4 | 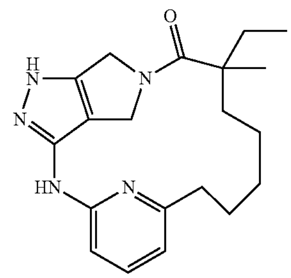 |
| I-5 | 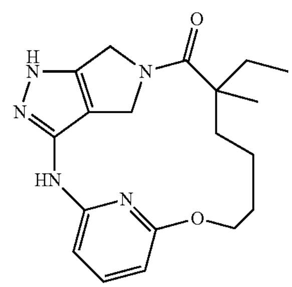 |
| I-6 | 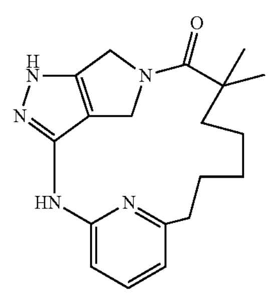 |
| I-7 | 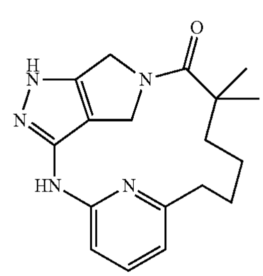 |

TABLE I-continued

| COMPOUND | STRUCTURE |
|---|---|
| I-8 | 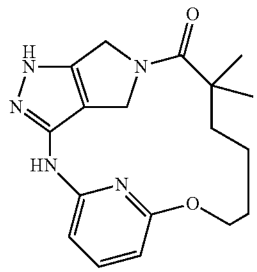 |
| I-9 | 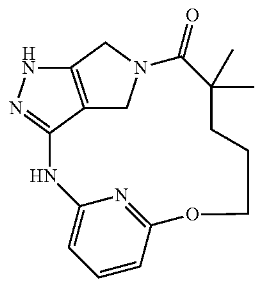 |
| I-10 | 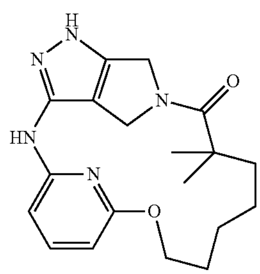 |
| I-11 | 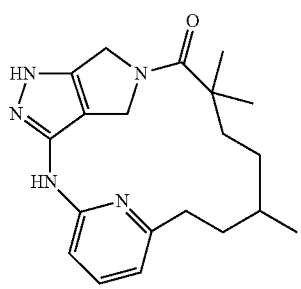 |
| I-12 | 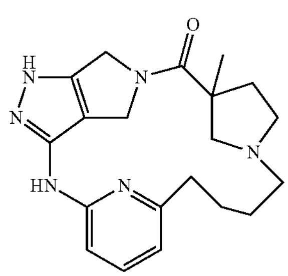 |
| I-13 | |
| I-14 | |
| I-15 | |
| I-16 | |
| I-17 | |

TABLE I-continued

| COMPOUND | STRUCTURE |
|---|---|
| I-18 | 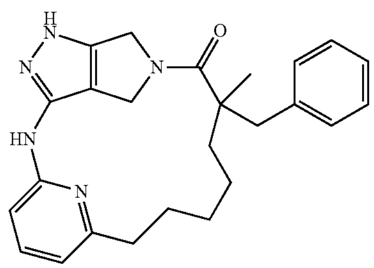 |

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzene-sulfonic acid, 4-chlorobenzenesulfonic acid, 2-naphthalene-sulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLES

Scheme 1.

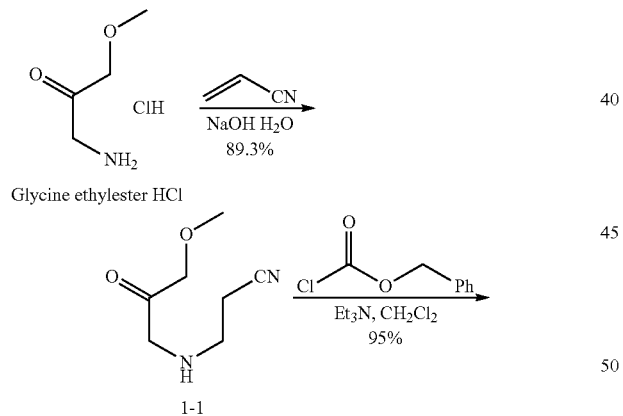

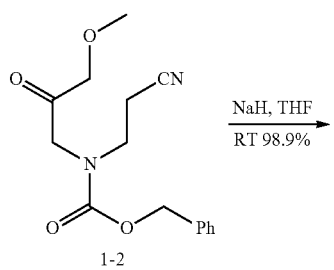

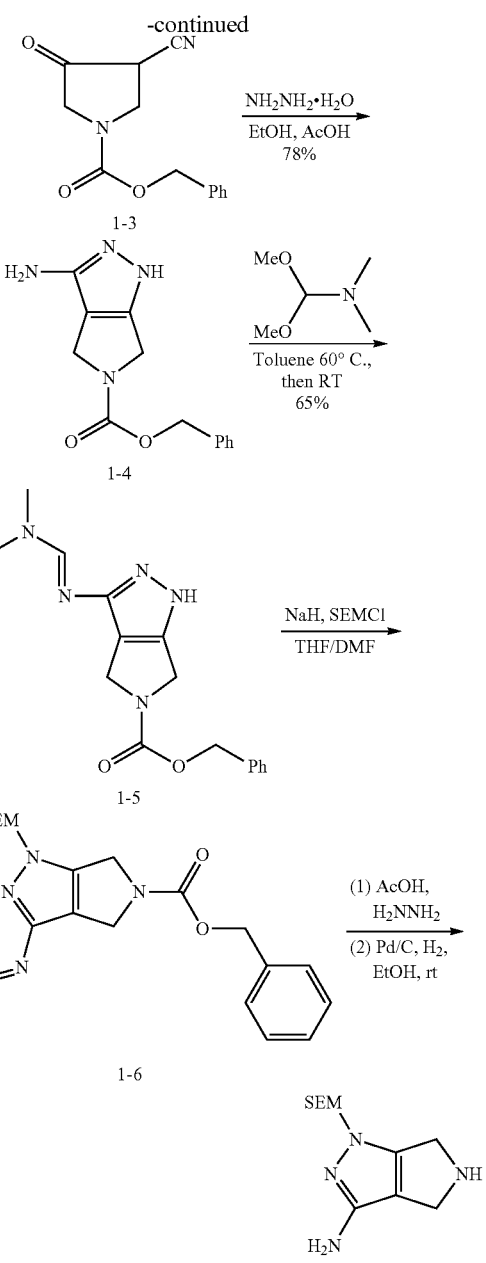

Experimental

Preparation of 1-1

To a mixture of 139.6 g (1 mole) of glycine ethylester HCl and 131.76 ml (2 mole) of acrylonitrile in 80 ml of water in an ice bath was treated drop wise with a solution of 516.11 g (1 mole) of KOH in 200 ml of water. After the addition completed, stirring continued at ice bath temp for two hrs and then stirred at ambient temperature over night. The pH of the reaction mixture adjusted to 7-8 with 1 N NaOH solution and the mixture extracted with $CH_2Cl_2$ (3×). The organic layer washed with water and brine, then dried and the solvent removed in vacuum to give 140 g of 1-1 as a light yellow oil.

Preparation of 1-2

A solution of 279 g (1.786 mole) of 1-1 and 498 ml (3.572 mole) of triethylamine in a 1000 ml of CH$_2$Cl$_2$ was cooled in an ice bath under nitrogen atmosphere. To this reaction, 253 ml (1.80 mol) of benzylchloroformate was slowly added while stirring using mechanical stirrer. Addition took 1 hr. The reaction mixture stirred for an additional 2 hrs at ice bath temp, then diluted with cold water. The organic layer separated and washed with dilute citric acid solution, water and brine. The organic layer dried and the solvent removed in vacuum to give 493 g (95%) of 1-2 as an amber color oil.

Preparation of 1-3

To a solution of 174.2 g (0.6 mole) of 1-2 in 1000 ml of THF was added 28.8 g (0.72 mole) of 60% NaH in portions and the resulting mixture stirred at ambient temperature under nitrogen atmosphere over night. The reaction mixture was concentrated and the yellow residue was dissolved in 300 ml of ice water and then pH adjusted to 3 with aq. Citric acid solution. The reaction mixture extracted with EtOAc (4×). The organic layer separated and washed with, water and brine. The organic layer dried and the solvent removed in vacuum to give 145.08 g (99%) of 1-3 as light yellow color oil.

Preparation of 1-4

A mixture containing 25.22 g (0.1044 mole) of 1-3 and 22.76 g (0.217 mole) of hydrazine dihydrochloride in 1000 ml of EtOH was heated at 60° C. for 2.5 hrs. The reaction mixture was concentrated in vacuum to give off white solid which was dissolved in cold water and then basified with aqueous saturated sodium carbonate solution. The solid formed was collected by filtration and washed several times with water and air dried, then washed with a small amount of cold EtOAc. The solid dried under vacuum to give 20.94 g (78.5%) of 1-4 as off white solid.

Preparation of 1-5

A mixture containing 51.66 g (0.200 mole) of 1-4 and 95.33 g (0.800 mole) of N,N-dimethylformamide dimethyl acetal in 600 ml of toluene was heated at 50-60° C. for 1 hr, then stirred at ambient temperature over night. The reaction mixture was concentrated in vacuum to give creamy light orange solid which was stirred in 1:1 EtOAc:Hexanes. The solid was collected by filtration and dried to give 40.74 g (65%) of 1-5 as light pink solid.

Preparation of 1-6

Preparation of 3-(Dimethylamino-methyleneamino)-1-(2-trimethylsilanyl-ethoxymethyl)-4,6-dihydro-1H-pyrrolo[3,4-c]pyrazole-5-carboxylic acid benzyl ester

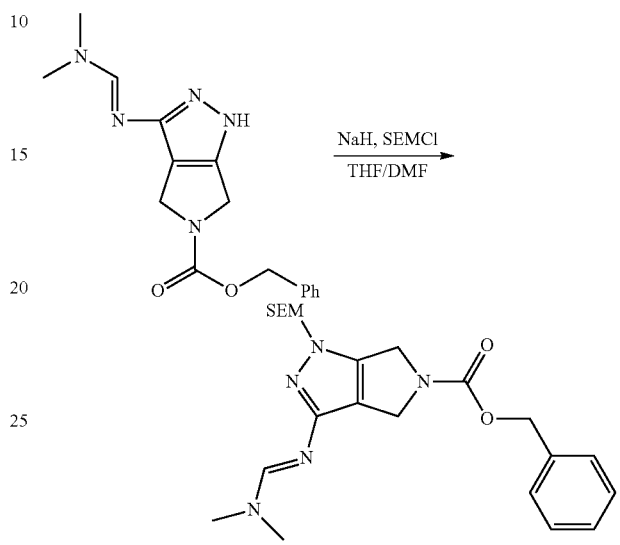

To a solution of 3-Amino-4,6-dihydro-1H-pyrrolo[3,4-c]pyrazole-5-carboxylic acid benzyl ester 1-5 (15.38 g, 49.1 mmol) in THF/DMF (2:1 ratio, 67 mL total) at 0° C. was added 2.36 g of sodium hydride (98.2 mmol, 3.928 g of NaH 60% dispersion in mineral oil). The reaction mixture was stirred for 15 minutes before the addition of (2-Chloromethoxy-ethyl)-trimethyl-silane (11.26 mL, 10.64 g, 63.8 mmol) via syringe. The reaction was slowly warmed to room temperature and stirred overnight. The reaction was quenched with sat. aq. NaHCO3 and extracted twice with EtOAc. The combined organics were dried over MgSO4, filtered and concentrated in vacuo. The crude product was purified by flash column chromatography (15→85% EtOAc/hexanes over 30 minutes). The desired product 1-6 was isolated as a brown oil, 17.5 g, 80% yield. 1H-NMR (300 MHz, CDCl3): 7.62 (d, J=16.6 Hz, 1H), 7.3-7.5 (m, 5H), 5.46 (d, J=2.5 Hz, 2H), 5.24 (d, J=3.6 Hz, 2H), 4.55 (d, J=14.5 Hz, 2H), 4.50 (d, J=11.2 Hz, 2H), 3.04 (s, 6H), 0.98 (m, 2H), 0.0 ppm (s, 9H). MS (E/I): 444 (M+H).

Preparation of 1-7

Step 1:

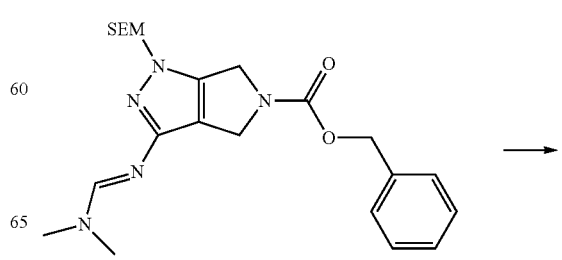

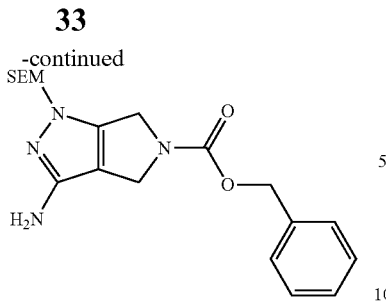

Procedure I

To a solution of 3-(Dimethylamino-methyleneamino)-1-(2-trimethylsilanyl-ethoxymethyl)-4,6-dihydro-1H-pyrrolo[3,4-c]pyrazole-5-carboxylic acid benzyl ester in 250 mL of ethanol was added 6.78 mL of acetic acid (7.11 g) and 15.31 mL of hydrazine hydrate (15.8 g). The reaction was heated to 50° C. and stirred overnight. The reaction was concentrated in vacuo and purified via flash column chromatography (15→80% EtOAc/hexanes over 30 minutes). The desired product was isolated as a yellow solid (5.73 g, 37% yield).

Procedure II

To a solution of 3-Amino-4,6-dihydro-1H-pyrrolo[3,4-c]pyrazole-5-carboxylic acid benzyl ester (16.7 g, 64.66 mmol) in 170 mL of anhydrous THF was added 1.86 g of sodium hydride (77.6 mmol, 3.10 g of NaH 60% dispersion in mineral oil) at 0° C. The suspension was stirred for 20 minutes at this temperature before the addition of 13.7 mL of (2-Chloromethoxy-ethyl)-trimethyl-silane (77.6 mmol, 12.9 g). The reaction was slowly warmed to room temperature and stirred overnight. The reaction was quenched with sat. aq. NH4Cl and extracted twice with EtOAc. The combined organic layers were dried over MgSO4, filtered and concentrated in vacuo. The crude reaction product was purified by flash column chromatography (10→70% EtOAc/hexanes over 35 minutes). The desired product was isolated as a yellow solid (10.18 g, 41% yield). 1H-NMR (CDCl3, 500 MHz): 7.3-7.45 (m, 5H), 5.31 (s, 2H), 5.21 (d, J=3.75, 2H), 4.46 (d, J=16.2 Hz, 2H), 4.41 (s, 2H), 3.83 (d, J=22.9 Hz, 2H), 3.57 (m, 2H), 1.26 (br s, 2H), 0.92 (m, 2H), 0.0 ppm (s, 9H). 13C-NMR (CDCl3, 126 MHz): 156.5, 154.5, 140.3, 138.2, 130.0, 129.4, 129.3, 104.0, 67.9, 47.3, 46.4, 31.1, 19.2, 1.4, 0.0 ppm. MP=110-115° C. IR (KBr): 3421, 2952, 2878, 1708, 1646, 1532, 1450, 1405, 1352, 1302, 1248, 1174, 1106, 1030, 860, 836, 760, 698, 615 cm-1. MS (E/I): 389 (M+H). Elemental Analysis: Calculated C, 58.73%; H, 7.26%; N, 14.42%. Found C, 58.84%; H, 7.07%; N, 14.09%.

Step 2:

A suspension of the product from step 1 (0.3 g, 0.77 mmol), 10% palladium on carbon (0.3 g) in EtOH (50 mL) was evacuated and refilled with hydrogen three times. After stirring at room temperature under $H_2$ (1 atm) for 6 h, the reaction mixture was filtered through Solka Floc. The filter cake was rinsed with EtOH. The filtrate was concentrated under reduced pressure to give 0.155 g of the desired product 1-7 as a white powder. Trituration with a mixture of $CH_2Cl_2$/hexane give an analytical pure sample. $^1$HNMR (CDCl$_3$, 500 Hz): 5.29 (s, 2H), 3.91 (d, J=15 Hz, 4H), 3.82-7.75 (br, 2H), 3.59 (t, J=8.2 Hz, 2H), 2.63-2.57 (br, 1H), 0.94 (t, J=8.4 Hz, 2H), 0 (s, 9H); $^{13}$CNMR (CDCl$_3$, 125 Hz): 160.9, 139.7, 108.9, 78.1, 67.3, 46.5, 45.5, 19.2, 1.4; MS calcd for $C_{11}H_{23}N_4OSi$ [M+H]$^+$: 255. Found, 255. EA calcd for $C_{11}H_{23}N_4OSi$: C, 51.93; H, 8.72; N, 22.02. Found: C, 50.70; H, 8.40; N, 21.19. IR (KBr): 3333, 3169, 2953, 2919, 2868, 1645, 1609, 1521, 1384, 1249, 1182, 1073, 996, 919, 861, 836, 758, 692 cm$^{-1}$.

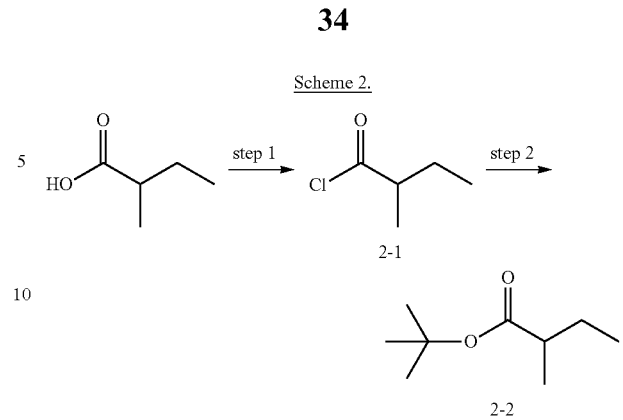

Step 1:

To a solution of 2-methyl-butyric acid (40 g, 392 mmol) and DMF (2 drops, ~0.1 mL) in $CH_2Cl_2$ (100 mL) at 0° C. was added oxalyl chloride (54.7 mL, 627 mmol, 1.6 equiv.) dropwise. The reaction was stirred at 0° C. for 1 h and then room temperature for 2 h. The reaction mixture was concentrated under reduced pressure with a rotary evaporator (bath temperature <20° C.). Dry $CH_2Cl_2$ was added and evaporated. The process was repeated three times to remove residual oxalyl chloride. The desired acid chloride 2-1 was collected as a yellow oil (38 g) in the bump trap after raising the bath temperature to ~40° C. The product was used in the next step without further purification.

Step 2:

To a solution of t-butyl alcohol (40.7 g, 549 mmol), Et$_3$N (70 mL, 505 mmol), and DMAP (0.366 mL, 3 mmol) in anhydrous $CH_2Cl_2$ (100 mL) at 0° C. was added 2-methyl-butyryl chloride (38 g from step 1). The reaction was stirred at 0° C. for 2 h and then room temperature overnight. The cloudy reaction mixture was filtered through celite and concentrated. The residue was diluted with Et$_2$O and washed with 0.1 N HCl. The organic layer was dried (MgSO$_4$), filtered, and concentrated. The residue was distilled at ~100° C. bath temperature under weak in-house vacuum twice to give the desired 2-methyl-butyric acid tert-butyl ester 2-2 as a clear oil (42 g, ~85% purity by $^1$HNMR analysis). $^1$HNMR (CDCl$_3$, 500 Hz): 2.28-2.20 (m 1H), 1.68-1.56 (m, 1H), 1.44 (s, 9H), 1.46-1.37 (m, 1H), 1.44 (s, 9H), 1.09 (d, J=7.0 hz, 3H), 0.9 (t, J=7.3 Hz, 3H).

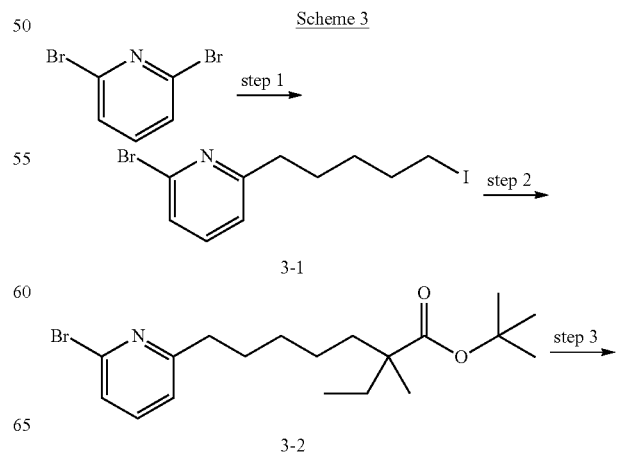

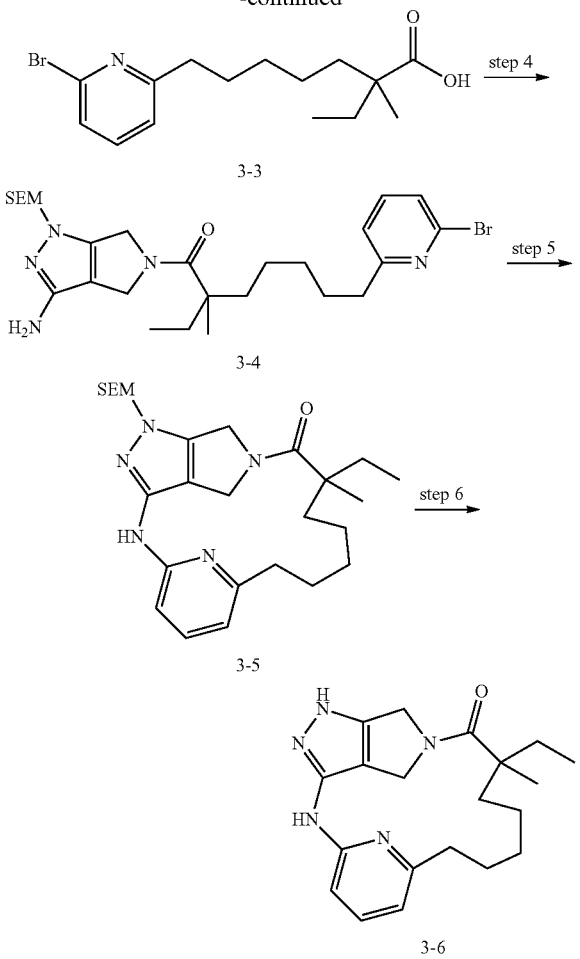

Step 1:

To a solution of n-BuLi (2.5 M in hexane, 5.4 mL, 13.4 mmol) in THF (30 mL) at −78° C. was added 2,6-dibromopyridine (3.18 g, 13.4 mmol) in THF (20 mL) dropwise. After completion of the addition, the resulting dark green solution was stirred for an additional 15 min. The solution was cannulated to a solution of 1,5-diiodopentane (5 mL, 10.9 g, 33.6 mmol) in THF (10 mL) at room temperature. After stirring at room temperature for 40 min, the reaction mixture was poured into brine and extracted with EtOAc (3×). The combined organic layer was dried ($Na_2SO_4$), filtered, and concentrated. The residue was purified by flash choloum chromatography with EtOAc in hexane (1% to 6% gradient over 20 min) to give the desired product 3-1 as a light yellow oil (3.18 g, 67% yield).

$^1$HNMR (CDCl$_3$, 500 Hz): 7.45 (t, J=7.7 Hz, 1H), 7.30 (d, J=7.7 Hz, 1H), 7.09 (d, J=7.4 Hz, 1H), 3.19 (t, J=7.0 Hz, 2H), 2.77 (t, J=7.6 Hz, 2H), 1.90-1.69 (m, 4H), 1.50-1.40 (m, 2H); $^{13}$CNMR (CDCl$_3$, 125 Hz): 164.0, 142.0, 139.0, 125.7, 121.9, 38.1, 33.6, 30.5, 29.0, 7.3. MS calcd for $C_{10}H_{14}BrIN$ [M+H]$^+$: 355.9. Found, 356.0. IR (KBr): 2930, 2855, 1581, 1553, 1435, 1404, 1224, 1198, 1163, 1127, 984, 858, 785, 759, 738, 674, 665 cm$^{-1}$.

Step 2:

To a solution of diisopropylamine (1.58 mL, 11.2 mmol) in THF (20 mL) at −78° C. was added n-BuLi (2.5 M in hexane, 4.1 mL, 10.2 mmol). The dry ice-acetone was removed after the addition. The reaction mixture was stirred for 10 min and then cooled to −78° C. A solution of 2-methyl-butyric acid tert-butyl ester (1.6 g, assuming 100% purity, 10.2 mmol) in THF (5 mL) was added to the above prepared LDA solution dropwise at −78° C. The mixture was stirred at −78° C. for 15 min during which the content turned orange-red. A solution of 3-1 (1.2 g, 3.4 mmol) in THF (4 mL+1 mL rinse) was added. After stirring at −78° C. for 30 min, the reaction was quenched with saturated aqueous NH$_4$Cl solution. The content was warmed to room temperature, diluted with 1/1 saturated aqueous NaHCO$_3$/brine, and extracted with EtOAc (2×). The combined organic layer was dried (Na$_2$SO$_4$), filtered, and concentrated. LC-MS analysis of the residue indicated a 1/1 mixture of 3-1/the desired product 3-2.

The same procedure was repeated with the above obtained 1/1 mixture except dry HMPA (3.4 mmol, 0.59 mL) was added 5 min after the addition of 2-methyl-butyric acid tert-butyl ester. Purification with flash column chromatography with EtOAc/hexane (1% to 6% gradient over 20 min) followed by preparative TLC with 3% EtOAc in hexane gave 0.63 g of the desired product 3-2 (48% yield) as a pale yellow oil.

$^1$HNMR (CDCl$_3$, 500 Hz): 7.43 (t, J=7.7 Hz, 1H), 7.29 (d, J=7.8 Hz, 1H), 7.08 (d, J=7.5 Hz, 1H), 2.74 (t, J=7.7 Hz, 2H), 1.74-1.55 (m, 4H), 1.47-1.29 (m, 6H), 1.42 (s, 9H), 1.03 (s, 3H), 0.82 (t, J=7.4 Hz, 3H); $^{13}$CNMR (CDCl$_3$, 125 Hz): 176.7, 164.1, 141.5, 138.5, 125.1, 121.4, 79.5, 46.5, 39.0, 38.0, 32.1, 29.9, 29.6, 28.0, 24.4, 20.4, 8.8. MS calcd for $C_{19}H_{31}BrNO_2$ [M+H]$^+$: 383. Found: 384. IR (neat); 2972, 2936, 2858, 1719, 1582, 1554, 1457, 1435, 1404, 1391, 1381, 1366, 1247, 1146, 984, 852, 786, 675 cm$^{-1}$.

Step 3:

A solution of compound 3-2 (0.6 g, 1.6 mmol) in hexafluoroisopropanol (6 mL) under Ar was heated in a microwave at 155° C. for 1.5 h. After cooling to room temperature, the solvent was removed under reduced pressure. The residue was used in the next step without further purification. MS calcd for $C_{15}H_{23}BrNO_2$ [M+H]$^+$: 330. Found: 330.

Step 4:

To a mixture of the above prepared acid 3-3, amine 1-7 (0.457 g, 1.8 mmol), EDCI (0.422 g, 2.2 mmol) and HOBT hydrate (0.298 g, 2.2 mmol) under Ar was added CH$_2$Cl$_2$ and i-Pr$_2$NEt sequentially. The reaction mixture was stirred at room temperature overnight, diluted with saturated aqueous NaHCO$_3$, and extracted with EtOAc (2×). The combined organic layer was dried (Na$_2$SO$_4$), filtered, and concentrated. The residue was purified by flash choloum chromatography with EtOAc in hexane (30% to 100% gradient over 30 min) to give the desired product 3-4 as a thick oil (0.21 g, 62% yield over two steps).

$^1$HNMR (CDCl$_3$, 500 Hz): 7.41 (t, J=7.7 Hz, 1H), 7.27 (d, J=7.2 Hz, 1H), 7.05 (d, J=7.5 Hz, 1H), 5.31 (s, 2H), 4.63-4.45 (br, 4H), 3.89 (br s, 2H), 3.63-3.58 (m, 2H), 2.72 (t, J=7.6 Hz, 2H), 1.89-1.63 (m, 4H), 1.52-1.39 (m, 6H), 1.24 (s, 3H), 0.96-0.85 (m, 5H); $^{13}$CNMR (CDCl$_3$, 125 Hz): 177.0, 165.4, 155.5, 142.8, 140.5, 139.9, 125.5, 122.8, 102.6, 67.5, 48.6, 48.4, 47.9, 40.0, 39.3, 32.7, 31.2, 30.9, 25.8, 24.4, 19.2, 10.4, 0.

Step 5:

A mixture of 1-[3-Amino-1-(2-trimethylsilanyl-ethoxymethyl)-4,6-dihydro-1H-pyrrolo[3,4-c]pyrazol-5-yl]-7-(6-bromo-pyridin-2-yl)-2-ethyl-2-methyl-heptan-1-one (0.20 g, 0.36 mmol), Pd$_2$(dba)$_3$ (0.050 g, 0.054 mmol, 15 mol %), XANTPHOS (0.63 g, 0.11 mmol, 30 mol %), and sodium tert-butoxide (0.048 g, 0.50 mmol, 1.4 equiv.) in a dry flask was evacuated and refilled with argon three times. Freshly degassed toluene (100 mL) was added to the mixture via cannula. The reaction was heated at 105° C. for 5 h. After cooling to room temperature, the content was poured into brine and extracted with EtOAc (3×). The combined organic layer was dried (Na$_2$SO$_4$), filtered, and concentrated. The residue was purified by flash choloum chromatography with EtOAc in hexane (30% to 100% gradient over 30 min) to give the desired product 3-5 as a yellow solid (0.134 g, 77% yield over two steps).

Mp: 128-130° C.; $^1$HNMR (CDCl$_3$, 300 Hz): 7.44 (dd, J=7.2, 8.0 Hz, 1H), 6.78 (s, 1H), 6.64 (d, J=7.5 Hz, 1H), 6.48 (d, J=8.3 Hz, 1H), 5.45 (d, J=11.5 Hz, 1H), 5.34 (d, J=11.6 Hz, 1H), 5.17 (d, J=12 Hz. 1H), 4.74 (t, J=11.5 Hz, 2H), 4.55 (d, J=15.7 Hz, 1H), 3.70-3.57 (m, 2H), 2.76-2.66 (m, 1H), 2.60-2.50 (m, 1H), 2.05-1.30 (m, 10H), 1.23 (s, 3H), 1.03-0.83 (m, 5H), 0 (s, 9H); $^{13}$CNMR (CDCl$_3$, 75 Hz): 177.4, 162.8, 154.0, 153.5, 139.7, 134.3, 115.7, 112.0, 108.1, 79.5, 78.5, 67.8, 50.5, 49.5, 48.6, 38.5, 33.9, 29.1, 28.7, 24.7, 23.0, 19.2, 10.2, 0; IR (neat): 3420, 3283, 2927, 2871, 1600, 1581, 1539, 1452, 1384, 1291, 1247, 1221, 1071, 1016, 944, 861, 836, 802, 778, 757 cm$^{-1}$; HRMS cacld for C26H42N5O2Si [M+H]$^+$: 484.3102. Found: 484.3092.

Step 6:

To a solution of compound 3-5 in CH$_2$Cl$_2$ (1.5 mL) at room temperature was added trifluoroacetic acid (1.5 mL). The reaction was stirred at room temperature for 1.5 h and then quenched with ice-cooled saturated NaHCO$_3$. The mixture was basified to about PH 9 with solid K$_2$HPO4 and extracted with EtOAc (3×). The combined organic layer was dried (Na$_2$SO$_4$), filtered, and concentrated. The residue was purified by preparative TLC with 4% MeOH in CH$_2$Cl$_2$ to give the desired product 3-6 as an off-white powder (0.060 g, 68% yield).

Mp: 282-284° C.; $^1$HNMR (DMSO-d$_6$, 500 Hz): 11.68 (br s, 1H), 8.81 (s, 1H), 7.39 (t, J=7.4 Hz, 1H), 6.59 (d, J=7.7 Hz, 1H), 6.54 (d, J=7.3 Hz, 1H), 5.11 (dd, J=1.8, 11.7 Hz, 1H), 4.73 (dd, J=1.8, 11.7 Hz, 1H), 4.57 (d, J=15.3 Hz, 1H), 4.39 (d, J=15.4 Hz, 1H), 2.67-2.57 (m, 1H), 2.53-2.44 (m 1H), 2.01-1.32 (m 10H), 1.13 (s, 3H), 0.80 (t, J=7.4 Hz, 3H); $^{13}$CNMR (CDCl$_3$, 125 Hz): 174.6, 159.9, 155.0, 151.7, 142.4, 141.2, 137.7, 112.0, 106.7, 49.0, 47.0, 46.3, 36.6, 36.4, 31.7, 27.4, 26.7, 23.1, 21.2, 8.7; HRMS calcd for C$_{20}$H$_{27}$N$_5$ [M+H]$^+$: 354.2288. Found: 354.2285; IR (KBr): 3298, 2922, 2865, 1609, 1531, 1490, 1456, 1384, 1304, 1197, 1153, 1090, 802, 769, 716, 635 cm$^{-1}$.

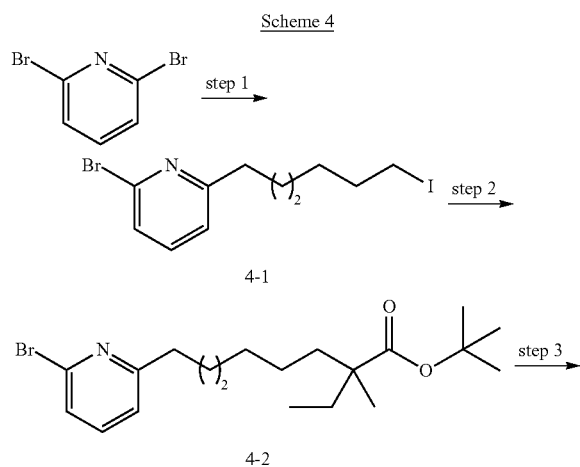

Scheme 4

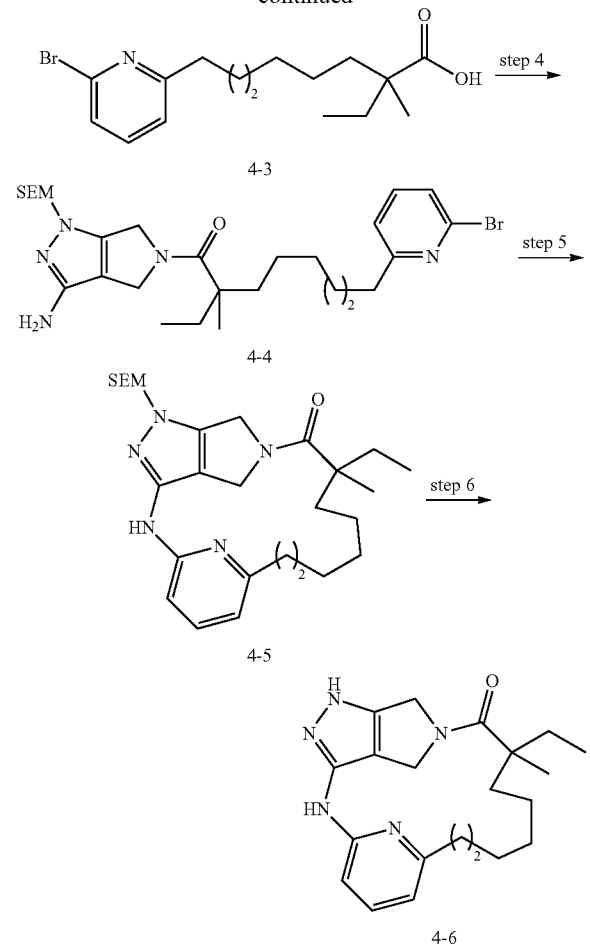

Step 1:

Followed step 1 in Scheme 3 except replacing 1,5-diiodopentane with 1,6-diiodohexane. Compound 4-1 (4 g, 65% yield) was obtained as a yellow oil.

$^1$HNMR (CDCl$_3$, 300 Hz): 7.44 (t, J=7.7 Hz, 1H), 7.28 (dd, J=0.7, 7.9 Hz, 1H), 7.08 (dd, J=0.7, 7.2 Hz, 1H), 3.18 (t, J=7.1 Hz, 2H), 2.73 (t, J=8.0 Hz, 2H), 1.85-1.66 (m, 4H), 1.48-1.30 (m, 4H); $^{13}$CNMR (CDCl$_3$, 75 Hz):163.9, 141.5, 138.5, 125.2, 121.4, 37.8, 33.3, 30.2, 29.4, 28.1, 7.0; MS calcd for C11H16BrIN [M+H]$^+$: 368. Found: 368; IR (KBr): 2928, 2854, 1581, 1552, 1434, 1404, 1350, 1192, 1161, 1126, 984, 858, 785, 736, 674, 664 cm$^{-1}$.

Step 2:

Followed step 2 in Scheme 3. Compound 4-2 (0.36 g, 22% yield) was obtained as a clear oil. $^1$HNMR (CDCl$_3$, 300 Hz): 7.42 (t, J=7.7 Hz, 1H), 7.28 (d, J=7.3 Hz, 1H), 7.07 (dd, J=0.6, 7.6 Hz, 1H), 2.74 (t, J=7.7 Hz, 2H), 1.72-1.55 (m, 4H), 1.38-1.25 (m 6H), 1.03 (s, 3H), 0.82 (t, J=7.5 Hz, 3H); $^{13}$CNMR (CDCl$_3$, 75 Hz): 176.8, 164.2, 141.5, 138.5, 125.2, 121.4, 79.6, 46.6, 39.2, 38.0, 32.2, 30.0, 29.7, 29.2, 28.1, 24.5, 20.5, 8.9; MS calcd for C20H33BrNO2 [M+H]$^+$: 398. Found: 398; IR (neat): 2971, 2934, 2857, 1720, 1582, 1554, 1458, 1435, 1404, 1391, 1381, 1366, 1344, 1247, 1147, 984, 852, 787, 675, 664 cm$^{-1}$.

Step 3:

Followed step 3 in Scheme 3. The crude product 4-3 was used in the next step without further purification. MS calcd for C16H25BrNO2 [M+H]$^+$: 342. Found: 342.

Step 4:

Followed step 4 in Scheme 3. Compound 4-4 was obtained as a pale yellow oil (0.226 g, 46% over two steps). ¹HNMR (CDCl₃, 500 Hz): 7.42 (t, J=7.6 Hz, 1H), 7.28 (d, J=7.8 Hz, 1H), 5.31 (s, 2H), 4.65-4.47 (m, 4H), 3.90 (s, 2H), 3.60 (t, J=8.3 Hz, 2H), 2.72 (t, J=7.7 Hz, 2H), 1.87-1.72 (m, 2H), 1.68-1.62 (m, 2H), 1.49-1.10 (m, 10H), 0.93 (t, J=6.4 Hz, 3H), 0.87 (t, J=7.4 Hz, 3H), 0 (s, 9H); ¹³CNMR (CDCl₃, 125 Hz): 177.1, 165.6, 142.9, 140.3, 140.0, 126.6, 122.9, 104.3, 102.5, 67.6, 49.2, 48.7, 48.4, 47.9, 47.2, 40.1, 39.4, 32.7, 31.5, 31.1, 30.5, 26.0, 24.4, 19.2, 10.4, 0; HRMS calcd for C27H45BrN5O2Si: 578.2520. Found: 578.2509; IR (neat): 2253, 1383, 909, 738, 650 cm⁻¹.

Step 5:

Followed step 5 in Scheme 3. Compound 4-5 was obtained as a yellow powder (0.1 g, 53% yield). ¹HNMR (CDCl₃, 500 Hz): 7.43 (t, J=7.6 Hz, 1H), 6.65 (d, J=7.4 Hz, 1H), 6.50 (d, J=8.1 Hz, 1H), 6.47 (s, 2H), 5.47 (d, J=11.4 Hz, 2H), 5.32 (d, J=11.4 Hz, 2H), 4.79 (d, J=12.1 Hz, 1H), 4.68 (dd, J=0.9, 15.8 Hz, 1H), 4.61-4.58 (m, 2H), 3.69-3.57 (m, 2H), 2.74-2.69 (m, 1H), 2.60-2.54 (m, 1H), 1.97-1.89 (m, 1H), 1.85-1.72 (m, 2H), 1.68-1.48 (m, 5H), 1.42-1.22 (m, 6H), 0.99-0.86 (m, 2H), 0.82 (t, J=7.4 Hz, 3H), 0 (s, 9H); ¹³CNMR (CDCl₃, 125 Hz): 177.2, 162.6, 155.0, 153.6, 139.6, 134.5, 117.2, 111.9, 109.0, 79.1, 67.9, 49.6, 48.9, 48.3, 40.1, 38.6, 32.5, 29.1, 28.4, 27.9, 24.6, 22.0, 19.3, 10.3, 0; IR (neat): 2253, 908, 735, 650 cm⁻¹.

Step 6:

Followed step 6 in Scheme 3. Compound 4-6 was obtained as a off-white powder (40 mg, 57% yield). ¹HNMR (DMSO-d₆, 500 Hz): 122.2-12.0 (m, 1H), 8.95 (s, 1H), 7.40 (br s, 1H), 6.60-6.49 (m, 2H), 4.82-4.35 (m, 4H), 2.57-2.46 (m, 1H), 1.88-1.70 (m, 3H), 1.54-1.38 (m, 9H), 1.23-1.16 (m, 1H), 1.08 (s, 3H), 0.72 (t, J=7.4 Hz, 3H); ¹³CNMR (DMSO-d₆, 125 Hz): 174.3, 159.4, 155.7, 154.9, 151.5, 141.9, 141.2, 137.5, 133.3, 113.5, 112.9, 112.1, 108.7, 107.3, 48.6, 47.1, 46.1, 37.9, 36.5, 30.4, 26.9, 26.4, 26.1, 23.1, 20.2, 8.8; MS calcd for C21H30N5O [M+H]⁺: 368. Found: 368; IR (KBr): 3260, 2935, 1597, 1534, 1505, 1458, 1395, 1300, 1218, 1195, 1158, 1110, 1061, 858, 787, 716 cm⁻¹.

Scheme 5

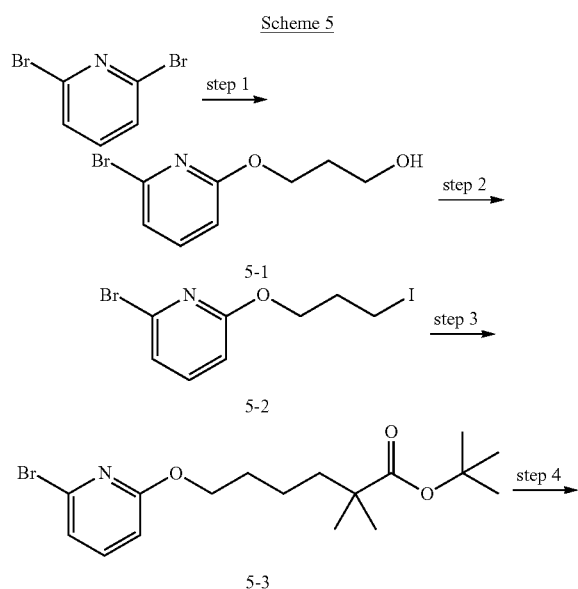

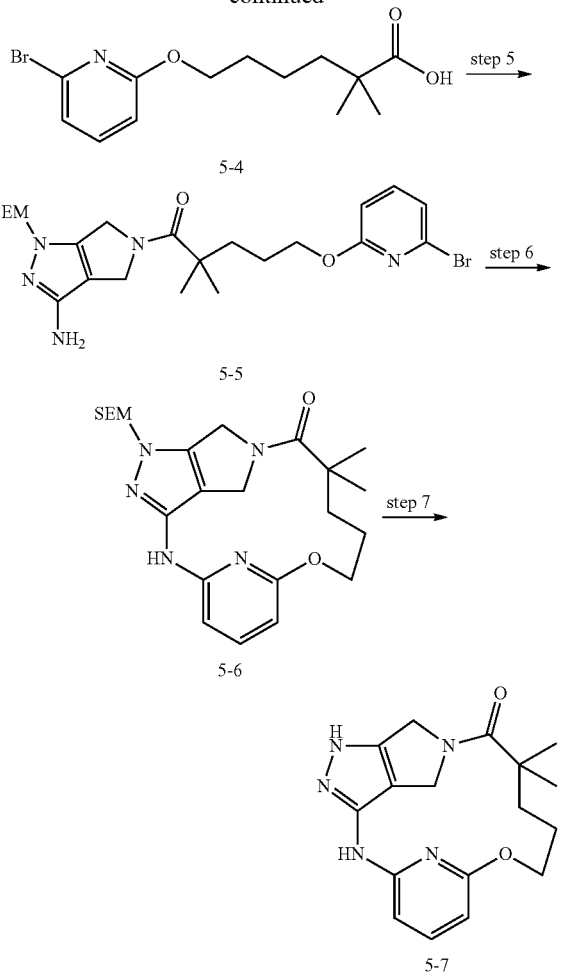

Step 1:

To a solution of 1,5-dibromopyridine (4.27 g, 18 mmol) and 1,3-propanediol (6.5 mL, 90 mmol) in DMF (30 mL) at 0° C. was added NaH (60% in mineral oil, 1.08 g, 27 mmol). The reaction was stirred at room temperature for 2 h and quenched with brine. The mixture was extracted with EtOAc (3×). The combined organic layer was dried (Na₂SO₄), filtered, and concentrated. The residue was purified by flash column chromatography with a mixture of CH₂Cl₂/MeOH/28% aqueous ammonium hydroxide (60:10:1) in CH₂Cl₂ (10% to 70% gradient over 30 min) to give 2.5 g of the desired product 5-1 (60% yield) as an oil.

¹HNMR (CDCl₃, 300 Hz): 7.42 (t, J=7.7 Hz, 1H), 7.04 (d, J=6.9 Hz, 1H), 6.67 (d, J=7.7 Hz, 1H), 4.46 (t, J=6.0 Hz, 2H), 3.74 (q, J=5.8 Hz, 2H), 2.03-1.95 (m, 2H); ¹³CNMR (CDCl₃, 75 Hz): 163.6, 140.6, 138.3, 120.3, 109.5, 63.8, 59.2, 32.1; EA calcd for C8H10BrNO2: C, 41.4; H, 4.34; N, 6.04. Found: C, 41.18; H, 4.26; N, 6.01. IR (neat): 3355, 2957, 2888, 1587, 1554, 1466, 1439, 1404, 1382, 1298, 1259, 1157, 1128, 1071, 1052, 1014, 982, 950, 878, 786 cm⁻¹.

Step 2:

To a solution of compound 5-1 (3.7 g, 15.9 mmol) and PPh₃ (3.75 g, 14.3 mmol) in anhydrous DMF (40 mL) at 0° C. was added N-iodosuccinimide (4.29 g, 19.1 mmol). The reaction was stirred at room temperature overnight. DMF (~30 mL) was removed under reduced pressure. The residue was diluted with brine and extracted with EtOAc (3×). The combined organic layer was dried (MgSO₄), filtered, and concentrated. The residue was purified by flash column chromatography with EtOAc/hexane (0% to 5% gradient over 30 min) to give 0.93 g of the desired product 5-2 as a clear oil.

¹HNMR (CDCl₃, 400 Hz): 7.42 (t, J=7.7 Hz, 1H), 7.06 (d, J=7.5 Hz, 1H), 6.67 (d, J=8.1 Hz, 1H), 4.36 (t, J=6.0 Hz, 2H), 3.32 (t, J=7.0 Hz, 2H), 2.31-2.25 (m, 2H); ¹³CNMR (CDCl₃, 75 Hz): 161.1, 138.4, 136.5, 118.4, 107.4, 64.1, 63.2, 30.7; HRMS calcd for C8H10BrINO [M+H]⁺: 341.8985. Found: 341.8980. IR (neat): 2961, 1587, 1555, 1439, 1404, 1372, 1299, 1260, 1181, 1156, 1125, 1077, 1011, 982, 926, 884, 845, 809, 786, 735 cm⁻¹.

Step 3:

To a solution of diisopropylamine (1.24 mL, 8.8 mmol) in THF (10 mL) at −78° C. was added n-BuLi (2.5 M in hexane, 3.2 mL, 8 mmol). The mixture was stirred at −78° C. for 10 min. Dry-ice acetone bath was removed. Stirring was continued for 10 min. The resulting pale-yellow LDA solution was cooled to −78° C. A solution of isobutyric acid t-butyl ester (1.15 g, 8 mmol) in THF (4 mL+1 mL rinse) was added via a syringe in a dropwise fashion. The mixture was stirred at −78° C. for 10 min before neat HMPA (0.61 mL, 3.5 mmol) was added. After stirring for another 5 min, compound 5-2 in THF (4 mL+1 mL rinse) was added. The reaction mixture was stirred at −78° C. for an additional 20 min and then quenched with saturated aqueous NH₄Cl. The content was warmed to room temperature, diluted with brine and extracted with EtOAc (3×). The combined organic layer was dried (MgSO₄), filtered and concentrated. The residue was purified by flash column chromatography with EtOAc/hexane (1% to 5% gradient over 30 min) to give 0.79 g of 5-3 as a clear oil.

¹HNMR (CDCl₃, 300 Hz): 7.39 (t, J=7.7 Hz, 1H), 7.02 (d, J=7.6 Hz, 1H), 6.65 (d, J=7.6 Hz, 1H), 4.66 (t, J=6.4 Hz, 2H), 1.77-1.48 (m, 2H), 1.43 (s, 9H), 1.15 (s, 6H); ¹³CNMR (CDCl₃, 75 Hz): 177.0, 163.6, 140.3, 138.6, 120.0, 109.5, 79.8, 67.1, 42.4, 37.0, 28.0, 25.2, 24.6; HRMS calcd for C16H25BrNO3 [M+H]⁺: 358.1012. Found: 358.1007; IR (neat): 2975, 1721, 1588, 1554, 1441, 1367, 1297, 1258, 1143, 1071, 1035, 1009, 981, 851, 787 cm⁻¹.

Step 4:

A solution of compound 5-3 (0.79 g, 2.2 mmol) in hexafluoroisopropanol (12 mL) was heated at 150° C. in a microwave for 2.5 h. After cooling to room temperature, the solvent was removed under reduced pressure to give the crude product 5-4, which was used in the next step without further purification. MS calcd for C12H17BrNO3 [M+H]⁺: 302. Found: 302.

Step 5:

To a mixture of acid 5-4 (crude from step 4), amine 1-7 (0.744 g, 2.36 mmol), 1-ethyl-3-(3-dimethylaminopropyl) carbodiimide hydrochloride (EDCI, 0.529 g, 2.76 mmol) and 1-hydroxybenzotriazole hydrate (Aldrich, 0.373 g, 2.76 mmol) was added CH₂Cl₂ (10 mL), followed by diisopropy-ethylamine (2.1 mL, 12 mmol). The reaction mixture was stirred at room temperature overnight and concentrated under reduced pressure. The residue was purified by flash column chromatography with EtOAc/hexane (20% to 100% gradient over 30 min) to give the desired product 5-5 as a white powder (0.5 g).

Mp: 133-135° C.; ¹HNMR (CDCl₃, 300 Hz): 7.34 (t, J=7.5 Hz, 1H), 6.98 (d, J=7.5 Hz, 1H), 6.59 (d, J=8.1 Hz, 1H), 5.30 (s, 2H), 4.64 (s, 2H), 4.54 (s, 2H), 4.29-4.24 (m, 2H), 3.64-3.59 (m, 2H), 1.82-1.73 (m, 4H), 1.32 (s, 6H), 0.96-0.89 (m, 2H), 0 (s, 9H); ¹³CNMR (CDCl₃, 75 Hz): 177.4, 164.8, 141.7, 140.5, 139.9, 121.5, 110.8, 78.6, 48.3, 67.6, 48.3, 44.1, 37.7, 27.5, 26.0, 19.2, 0; HRMS calcd for C23H37BrN5O3Si [M+H]⁺: 538. Found: 538; IR (KBr): 3428, 3319, 2956, 1651, 1593, 1554, 1527, 1441, 1403, 1382, 1363, 1301, 1249, 1161, 1071, 1018, 881, 859, 836, 778 cm⁻¹.

Step 6:

To a mixture of compound 5-5 (0.138 g, 0.23 mmol), Pd₂(dba)₃ (0.042 g, 0.046 mmol), XANTPHOS (0.053 g, 0.092 mmol) and sodium t-butoxide (0.033 g, 0.35 mmol) under Ar was added freshly degassed toluene via cannula. After the cannulation, the mixture was evacuated under high vacuum and then refilled with Ar. The process was repeated twice. The reaction was heated at 105° C. under Ar for 2.5 h and cooled to room temperature. The content was poured into brine and extracted with EtOAc (3×). The combined organic layer was dried (Na₂SO₄), filtered and concentrated. The residue was purified by flash column chromatography with EtOAc/hexane (80%) to give the desired product 5-6 as a yellow powder (0.065 g).

¹HNMR (CDCl₃, 300 Hz): 7.46 (t, J=7.9 Hz, 1H), 6.38 (br s, 1H), 6.26 (dd, J=2.1, 7.8 Hz, 1H), 5.40 (s, 2H), 4.68 (s, 2H), 4.56 (s, 2H), 4.20-4.15 (m, 2H), 3.62-3.57 (m, 2H), 1.80-1.74 (m, 4H), 1.28 (s, 6H), 0.97-0.91 (m, 2H), 0 (s, 9H); ¹³CNMR (CDCl₃, 75 Hz): 177.4, 165.8, 156.0, 154.8, 140.1, 134.8, 114.8, 104.2, 103.5, 79.0, 68.1, 67.8, 48.5, 47.6, 43.7, 36.7, 29.5, 26.2, 19.3, 0; HRMS cacld for C23H36N5O3Si [M+H]⁺: 458.2582. Found: 458.2570 IR (neat): 3422, 2952, 1606, 1522, 1473, 1448, 1428, 1384, 1364, 1299, 1248, 1223, 1164, 1079, 1022, 859, 835, 788, 730, 693 cm⁻¹.

Step 7:

To a solution of compound 5-6 (40 mg) in CH₂Cl₂ (1 mL) at room temperature was added TFA (1 mL). After stirring at room temperature for 1 h, the reaction mixture was poured into ~150 mL ice-cold saturated NaHCO₃ solution. PH of the aqueous layer was adjusted to >9 with K₂HPO₄. The biphasic mixture was extracted with EtOAc (3×). The combined organic layer was dried (Na₂SO₄), filtered and concentrated. The residue was purified by preparative TLC with a mixture of CH₂Cl₂/MeOH/28% aqueous ammonium hydroxide (60:10:1) and CH₂Cl₂ (2:3 volume ratio) to give the desired product 5-7 (7 mg, >98% purity based on absorption at 190-400 nM range by LC/MS analysis on an agilent SB-C18 2.1×35 mm column).

¹HNMR (DMSO-d₆ with TFA vapor, 500 Hz): 9.45 (br s, 1H), 9.16 (br s, 1H), 7.44 (t, J=7.7 Hz, 1H), 6.34 (d, J=7.8 Hz, 1H), 6.10 (d, J=7.8 Hz, 1H), 4.51 (s, 2H), 4.50 (s, 2H), 4.08 (t, J=6.3 Hz, 2H), 1.72-1.63 (m, 4H), 1.17 (s, 6H); ¹³CNMR (DMSO-d₆, 125 Hz): 17.0, 163.5, 154.0, 149.5, 140.3, 137.2, 111.9, 102.1, 100.0, 65.6, 46.8, 45.2, 41.6, 34.7, 27.9, 24.3; HRMS cacld for C17H22N5O3 [M+H]⁺: 328.1768. Found: 328.1773.

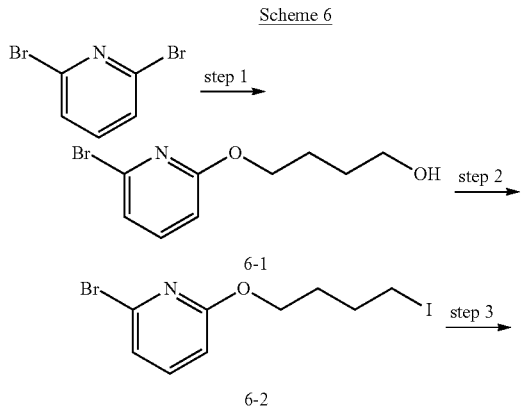

Scheme 6

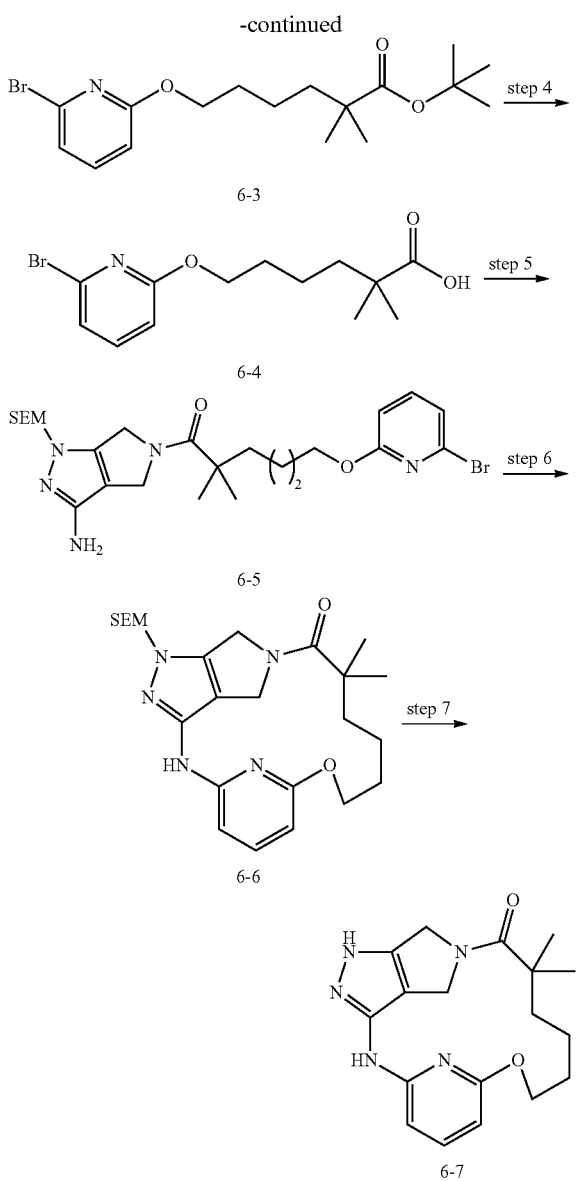

Step 1:

Followed step 1 in Scheme 5 except replacing 1,3-propanediol with 1,4-butanediol, 81% yield.

$^1$HNMR (CDCl$_3$, 300 Hz): 7.40 (dd, J=7.6, 0.7 Hz, 1H), 7.03 (dd, J=7.4, 0.7 Hz, 1H), 6.66 (dd, J=8.0, 0.7 Hz, 1H), 4.33 (t, J=6.3 Hz, 2H), 3.75-3.68 (m, 2H), 1.91-1.82 (m, 2H), 1.77-1.48 (m, 2H); $^{13}$CNMR (CDCl$_3$, 75 Hz): 163.5, 140.4, 138.6, 120.2, 109.5, 66.5, 62.6, 29.3, 25.3; EA calcd for C9H12BrNO2: C, 43.92; H, 4.91; N, 5.69. Found: 43.48; H, 4.78; N, 5.65; IR (neat): 3350, 2949, 2874, 1587, 1554, 1466, 1440, 1404, 1382, 1298, 1259, 1157, 1127, 1070, 1042, 1007, 982, 959, 786, 674 cm$^{-1}$.

Step 2:

To a solution of compound 6-1 (2.6 g, 10.6 mmol) and Ph$_3$P (2.5 g, 9.5 mmol) in anhydrous DMF (20 mL) at room temperature was added N-iodosuccinimide (3.2 g, 13.7 mmol) in five portions over 45 min. After completion of the addition, the reaction was stirred for an additional 3 h at room temperature in the dark. The content was diluted with 5/1 mixture of brine/saturated aqueous NaS$_2$O$_3$ and extracted with EtOAc. The combined organic layer was dried (Na$_2$SO$_4$), filtered and concentrated. The residue was purified by flash column chromatography with EtOAc/hexane (1% to 6% gradient over 30 min) to give the desired product 6-2 as a light pink oil (2.2 g, 59% yield).

$^1$HNMR (CDCl$_3$, 500 Hz): 7.41 (t, J=7.8 Hz, 1H), 7.04 (d, J=7.4 Hz, 1H), 6.66 (d, J=8.2 Hz, 1H), 4.32 (t, J=6.3 Hz, 2H), 3.26 (t, J=6.9 Hz, 2H), 2.03-1.97 (m, 2H), 1.92-1.85 (m, 2H); $^{13}$CNMR (CDCl$_3$, 125 Hz): 163.3, 140.4, 138.5, 120.2, 109.4, 65.6, 30.2, 29.8, 6.3; MS calcd for C9H12BrINO [M+H]$^+$: 356. Found: 356; IR (neat): 2953, 1588, 1554, 1465, 1440, 1403, 1378, 1296, 1259, 1223, 1155, 1126, 1071, 1011, 981, 943, 878, 785, 724, 674 cm$^{-1}$.

Step 3:

Followed step 3 in Scheme 5. Starting from 2.1 g of iodide 6-2, 2.65 g of compound 6-3 (~80% purity by $^1$HNMR analysis) was obtained after preparative TLC with EtOAc/hexane (1.5%). The impure 6-3 was used in step 4 without further purification. MS calcd for C17H27BrNO3 [M+H]$^+$: 372. Found: 372.

Step 4:

Followed step 4 in Scheme 5. MS calcd for C13H19BrNO3 [M+H]$^+$: 316. Found: 316.

Step 5:

Followed step 5 in Scheme 5. Starting from 0.744 g of 6-4, 0.3 g of 6-5 was obtained as a clear oil.

$^1$HNMR (CDCl$_3$, 400 Hz): 7.37 (t, J=7.7 Hz, 1H), 7.01 (d, J=7.5 Hz, 1H), 6.61 (d, J=8.1 hz, 1H), 5.32 (s, 2H), 4.70-4.48 (br m, 5H), 4.26 (t, J=6.5 Hz, 2H), 3.63-3.58 (m, 2H), 1.78-1.67 (m, 4H), 1.48-1.39 (m, 2H), 1.30 (s, 6H), 0.94-0.90 (m, 2H), 0 (s, 9H); $^{13}$CNMR (CDCl$_3$, 100 Hz): 177.7, 164.9, 141.7, 139.9, 121.4, 110.8, 78.6, 67.8, 67.6, 66.7, 44.3, 41.2, 30.7, 27.5, 22.9, 19.2, 0; MS calcd for C24H39BrN5O3Si [M+H]$^+$: 552. Found: 552; IR (neat): 3328, 2952, 1615, 1554, 1439, 1363, 1299, 1155, 1070, 836, 786, 732 cm$^{-1}$.

Step 6:

Followed step 6 in Scheme 5. Starting from 0.29 g of 6-5, 0.16 g of 6-6 was contained as a yellow foam (70% yield). $^1$HNMR (CDCl$_3$, 500 Hz): 7.50 (t, J=7.9 Hz, 1H), 6.64 (s, 1H), 6.33 (d, J=7.8 Hz, 1H), 6.29 (d, J=7.9 Hz, 1H), 5.40 (s, 2H), 4.75 (s, 2H), 4.64 (s, 2H), 4.30 (t, J=5.5 Hz, 2H), 3.61 (t, J=8.3 Hz, 2H), 1.86-1.81 (m, 2H), 1.80-1.76 (m, 2H), 1.58-1.53 (m, 2H), 1.23 (s, 6H), 0.95-0.92 (m, 2H), 0 (s, 9H); $^{13}$CNMR (CDCl$_3$, 125 Hz): 176.6, 163.8, 152.6, 151.8, 140.9, 133.1, 109.9, 103.1, 102.5, 77.9, 68.4, 66.5, 48.7, 47.7, 43.0, 38.3, 28.3, 26.5, 22.7, 17.9, 0; HRMS cacld for C24H38N5O3Si [M+H]$^+$: 472.2738. Found: 472.2730; IR (KBr): 3422, 2950, 1652, 1606, 1539, 1456, 1428, 1384, 1362, 1300, 1248, 1223, 1151, 1077, 859, 836, 790, 754, 694, 667 cm$^{-1}$.

Step 7:

Followed step 7 in Scheme 5, 16 mg of 6-7 was obtained (55% yield). $^1$HNMR (DMSO-d$_6$ with TFA vapor, 500 Hz): 7.51 (t, J=7.7 Hz, 1H), 6.43 (d, J=7.9 Hz, 1H), 6.20 (d, J=7.7 Hz, 1H), 4.71 (s, 2H), 4.49 (s, 2H), 4.19 (t, J=5.3 Hz, 2H), 1.80-1.77 (m, 2H), 1.72-1.68 (m, 2H), 1.48-1.42 (m, 2H), 1.12 (s, 6H); $^{13}$CNMR (CDCl$_3$, 125 Hz): 175.2, 163.1, 153.3, 146.0, 140.7, 138.7, 110.4, 103.3, 99.9, 67.9, 48.5, 46.8, 42.4, 37.6, 27.8, 26.3, 22.2; HRMS cacld for C18H24N5O2 [M+H]$^+$: 342.1925. Found: 342.1929.

Scheme 7

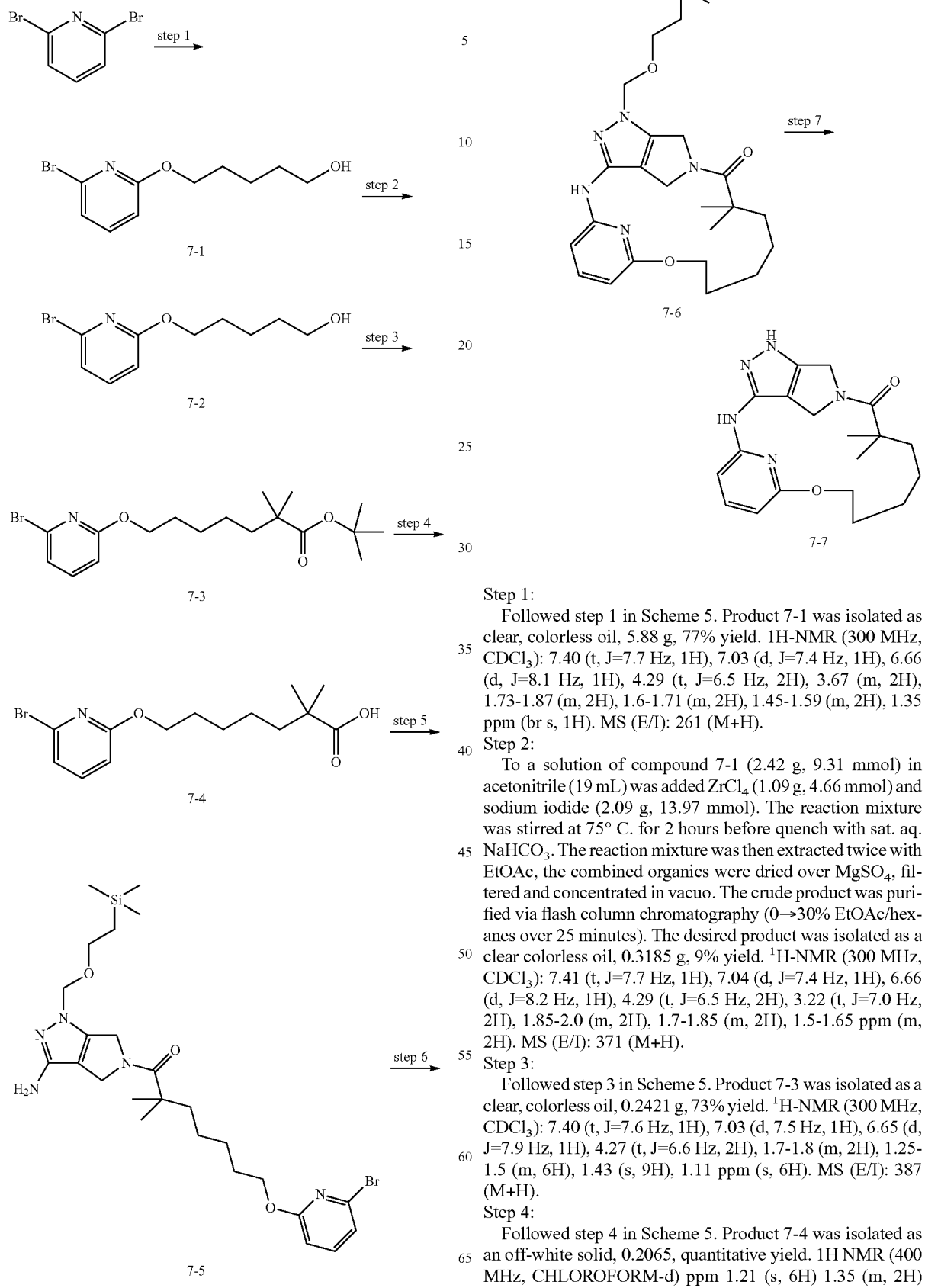

Step 1:
Followed step 1 in Scheme 5. Product 7-1 was isolated as clear, colorless oil, 5.88 g, 77% yield. 1H-NMR (300 MHz, CDCl$_3$): 7.40 (t, J=7.7 Hz, 1H), 7.03 (d, J=7.4 Hz, 1H), 6.66 (d, J=8.1 Hz, 1H), 4.29 (t, J=6.5 Hz, 2H), 3.67 (m, 2H), 1.73-1.87 (m, 2H), 1.6-1.71 (m, 2H), 1.45-1.59 (m, 2H), 1.35 ppm (br s, 1H). MS (E/I): 261 (M+H).

Step 2:
To a solution of compound 7-1 (2.42 g, 9.31 mmol) in acetonitrile (19 mL) was added ZrCl$_4$ (1.09 g, 4.66 mmol) and sodium iodide (2.09 g, 13.97 mmol). The reaction mixture was stirred at 75° C. for 2 hours before quench with sat. aq. NaHCO$_3$. The reaction mixture was then extracted twice with EtOAc, the combined organics were dried over MgSO$_4$, filtered and concentrated in vacuo. The crude product was purified via flash column chromatography (0→30% EtOAc/hexanes over 25 minutes). The desired product was isolated as a clear colorless oil, 0.3185 g, 9% yield. $^1$H-NMR (300 MHz, CDCl$_3$): 7.41 (t, J=7.7 Hz, 1H), 7.04 (d, J=7.4 Hz, 1H), 6.66 (d, J=8.2 Hz, 1H), 4.29 (t, J=6.5 Hz, 2H), 3.22 (t, J=7.0 Hz, 2H), 1.85-2.0 (m, 2H), 1.7-1.85 (m, 2H), 1.5-1.65 ppm (m, 2H). MS (E/I): 371 (M+H).

Step 3:
Followed step 3 in Scheme 5. Product 7-3 was isolated as a clear, colorless oil, 0.2421 g, 73% yield. $^1$H-NMR (300 MHz, CDCl$_3$): 7.40 (t, J=7.6 Hz, 1H), 7.03 (d, 7.5 Hz, 1H), 6.65 (d, J=7.9 Hz, 1H), 4.27 (t, J=6.6 Hz, 2H), 1.7-1.8 (m, 2H), 1.25-1.5 (m, 6H), 1.43 (s, 9H), 1.11 ppm (s, 6H). MS (E/I): 387 (M+H).

Step 4:
Followed step 4 in Scheme 5. Product 7-4 was isolated as an off-white solid, 0.2065, quantitative yield. 1H NMR (400 MHz, CHLOROFORM-d) ppm 1.21 (s, 6H) 1.35 (m, 2H) 1.39-1.49 (m, 2H) 1.50-1.65 (m, 2H) 1.67-1.86 (m, 2H) 4.27

(t, J=7.33 Hz, 2H) 6.66 (d, J=8.08 Hz, 1H) 7.03 (d, J=7.58 Hz, 1H) 7.40 (t, J=7.83 Hz, 1H). MS (E/I): 331 (M+H).

Step 5:

Followed step 5 in Scheme 5. Product 7-5 was isolated as a white solid, 0.402 g, 67% yield. 1H NMR (300 MHz, CHLOROFORM-d) ppm 0.00 (s, 9H) 0.88-0.99 (m, 2H) 1.30 (s, 6H) 1.33-1.50 (m, 4H) 1.58-1.78 (m, 4H) 3.56-3.69 (m, 2H) 3.87 (br. s, 2H) 4.25 (t, J=6.61 Hz, 2H) 4.49 (br. s., 2H) 4.66 (br. s., 2H) 5.31 (s, 1H) 6.64 (d, J=8.31 Hz, 1H) 7.02 (d, J=7.18 Hz, 1H) 7.38 (t, J=7.93 Hz, 1H). MS (E/I): 567 (M+H).

Step 6:

Followed step 6 in Scheme 5. Product 7-6 was isolated as yellow solid, 0.243 g, 71% yield. 1H NMR (300 MHz, CHLOROFORM-d) ppm 0.00 (s, 9H) 0.83-1.07 (m, 2H) 1.26 (s, 6H) 1.31-1.55 (m, 4H) 1.59-1.93 (m, 4H) 3.48-3.64 (m, 2H) 4.31 (t, J=7.37 Hz, 2H) 4.66 (s, 2H) 4.77 (s, 2H) 5.40 (s, 2H) 6.23 (d, J=7.93 Hz, 2H) 6.60 (s, 1H) 7.44 (t, J=7.93 Hz, 1H). MS (E/I): 486 (M+H). IR (KBr): 3421, 2935, 2871, 1611, 1535, 1457, 1429, 1395, 1362, 1304, 1248, 1232, 1152, 1079, 989, 860, 836, 785, 694 cm$^{-1}$.

Step 7:

Followed step 7 in Scheme 5. Product 7-6 was isolated as a yellow solid, 0.029 g, 13% yield. 1H-NMR (500 MHz, DMSO-$d_6$ with TFA): ppm 9.29 (br s, 1H), 7.60 (t, J=7.75 Hz, 1H), 6.48 (d, J=7.9 Hz), 6.22 (d, J=7.85 Hz, 1H), 4.89 (s, 2H), 4.65 (s, 2H), 4.42 (t, J=7.25, 2H), 1.75-1.9 (m, 4H), 1.62 (m, 2H), 1.44 (m, 2H), 1.33 (s, 6H). 13C-NMR (126 MHz, DSMO-$d_6$ with TFA): ppm 174.8, 162.8, 154.2, 146.1, 140.2, 137.6, 110.9, 101.2, 98.9, 62.1, 47.1, 42.1, 37.7, 26.7, 26.1, 23.6, 21.3. IR (KBr): 3408, 2932, 2870, 1610, 1530, 1461, 1429, 1400, 1383, 1365, 1309, 1234, 1203, 1153, 1095, 1067, 1046, 788, 724 cm$^{-1}$. MS (E/I): 356 (M+H). MP=234.0-237.0° C.

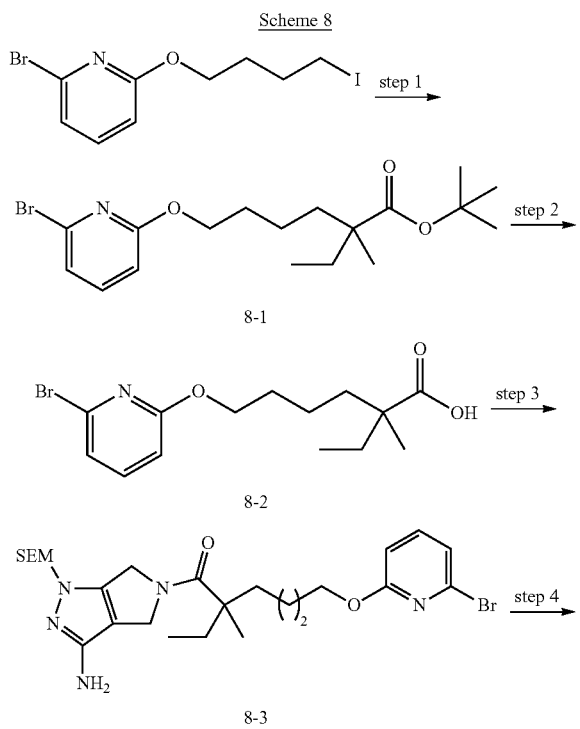

Scheme 8

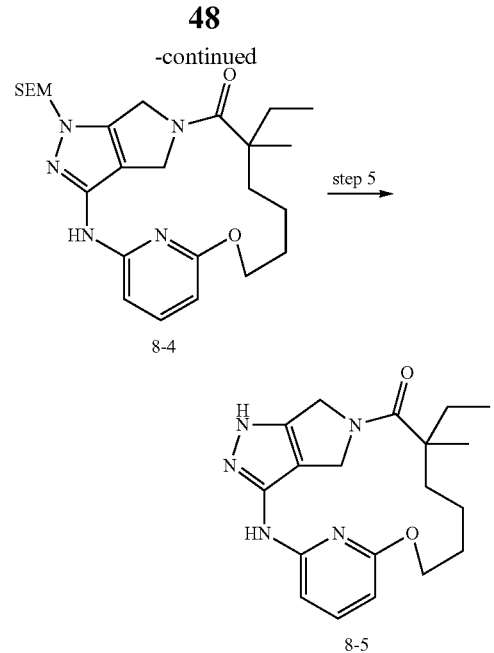

Step 1:

Followed step 3 in Scheme 5 except replacing isobutyric acid t-butyl ester with 2-methyl-butyric acid tert-butyl ester, 53% yield of 8-1. $^1$HNMR (CDCl$_3$, 500 Hz): 7.39 (t, J=7.7 Hz, 1H), 7.04 (d, J=8.4 Hz, 1H), 6.63 (d, J=8.2 Hz, 1H), 4.27 (t, J=6.5 Hz, 1H), 1.76-1.71 (m, 2H), 1.68-1.62 (m, 2H), 1.48-1.37 (m, 2H), 1.42 (s, 9H), 1.06 (s, 3H), 0.81 (t, J=7.0 Hz, 3H); $^{13}$CNMR (CDCl$_3$, 125 Hz): 176.6, 163.6, 140.2, 138.6, 120.0, 109.5, 79.7, 66.6, 46.6, 38.8, 32.2, 29.4, 28.1, 21.1, 20.4, 8.8; IR (neat): 2971, 1721, 1587, 1554, 1440, 1403, 1367, 1297, 1250, 1142, 1071, 1008, 981, 965, 881, 852, 787, 725, 675 cm$^{-1}$; MS calcd for C16H27BrNO3 [M+H]$^+$: 386. Found: 386.

Step 2:

Followed step 4 in Scheme 5. 0.65 g of compound 8-1 was used to give crude 8-2, which was used in the next step without further purification. MS calcd for C14H21BrNO3 [M+H]$^+$: 332. Found: 332.

Step 3:

Followed step 5 in Scheme 5. Compound 8-3 was obtained as a thick clear oil (0.53 g, 57% yield over two steps). $^1$HNMR (CDCl$_3$, 500 Hz): 7.37 (t, J=7.9 Hz, 1H), 7.01 (d, J=7.4 Hz, 1H), 6.61 (d, J=8.1 Hz, 1H), 5.31 (s, 2H), 4.68-4.48 (br m, 4H), 4.60-4.53 (m 2H), 3.61 (t, J=8.5 Hz, 2H), 1.92-1.83 (m, 2H), 1.77-1.70 (m, 2H), 1.58-1.45 (m, 3H), 1.38-1.30 (m, 1H), 1.26 (s, 3H), 0.93 (t, J=8.4 Hz, 3H), 0.88 (t, J=7.4 Hz, 3H); $^{13}$CNMR (CDCl$_3$, 125 Hz): 175.5, 163.5, 154.1, 152.2, 140.3, 139.3, 138.5, 120.0, 109.4, 103.1, 101.1, 77.4, 66.4, 66.2, 48.1, 47.2, 47.1, 46.6, 38.4, 31.3, 29.3, 23.0, 21.2, 17.8, 9.0, −1.4; HRMS calcd for C25H41BrN5O3Si [M+H]$^+$: 566.2157. Found: 566.2152; IR (neat): 4358, 4064, 3853, 3331, 3219, 2917, 2661, 2361, 2331, 2238, 2179, 1995, 1793, 1734, 1652, 1558, 1456, 1127, 1066, 939, 879, 770, 725 cm$^1$.

Step 4:

Followed step 6 in Scheme 5. Compound 8-4 was obtained as a yellow foam (0.2 g, 59% yield). Mp: 95-100° C. $^1$HNMR (CDCl$_3$, 300 Hz): 7.51 (t, J=7.9 Hz, 1H), 6.62 (s, 1H), 6.34 (d, J=7.8 Hz, 1H), 6.31 (d, J=7.9 hz, 1H), 5.47 (d, J=7.4 Hz, 1H), 5.35 (d, J=11.5 Hz, 1H), 5.04 (d, J=12.5 Hz, 1H), 4.78 (dd, J=1.1, 15.7 Hz, 1H), 4.60-4.43 (m, 3H), 4.08-4.02 (m, 1H), 3.67-3.55 (m, 2H), 2.03-1.65 (m, 4H), 1.47-1.38 (m, 2H), 1.23 (s, 3H), 1.02-0.90 (m, 2H), 0.87 (t, J=7.4 Hz, 3H), 0 (s, 9H); $^{13}$CNMR (CDCl$_3$, 75 Hz): 177.1, 165.2, 154.0, 153.2, 142.3, 134.5, 111.6, 104.3, 104.0, 79.2, 69.8, 67.8, 49.7, 49.0, 48.6, 39.1, 32.8, 29.9, 24.5, 24.0, 19.3, 10.4, 0; HRMS calcd for C25H40N5O3Si [M+H]$^+$: 486.2895. Found: 486.2889; IR (KBr): 3268, 2950, 2875, 1606, 1532, 1456, 1427, 1384, 1347, 1300, 1248, 1224, 1151, 1077, 941, 859, 836, 789, 732, 694 cm$^{-1}$.

Step 5:

Followed step 7 in Scheme 5. Compound 8-4 was obtained as a light brown solid (70 mg, 49% yield, >98% purity based on absorption at 190-400 nM range after separation on an agilent SB-C18 2.1×35 mm column). Mp: 248-252° C.; $^1$HNMR (DMSO-d$_6$ with TFA vapor, 500 Hz): 7.50 (t, J=7.7 Hz, 1H), 6.40 (d, J=8.0 hz, 1H), 6.17 (d, J=7.7 Hz, 1H), 4.95 (d, J=11.0 Hz, 1H), 4.59 (dd, J=1.5, 15.1 Hz, 1H), 4.41 (t, J=12.1 Hz, 2H), 4.43-4.38 (m, 1H), 3.98-3.94 (m, 1H), 1.96-1.90 (m, 1H), 1.84-1.76 (m, 1H), 1.74-1.68 (m, 1H), 1.65-1.56 (m, 3H), 1.38-1.28 (m, 2H), 1.09 (s, 3H), 0.76 (t, J=7.2 Hz, 3H); $^{13}$CNMR (DMSO-d6 with TFA vapor, 125 Hz): 174.3, 163.0, 153.6, 145.5, 140.5, 138.6, 110.5, 103.0, 99.6, 67.8, 48.2, 46.7, 46.5, 37.0, 30.9, 27.9, 22.9, 22.1, 8.5; HRMS calcd for C19H26N5O2 [M+H]$^+$: 356.2081. Found: 356.2078; IR (KBr): 3250, 2965, 2934, 2875, 1599, 1528, 1458, 1430, 1394, 1319, 1229, 1203, 1149, 1103, 1043, 789, 731 cm$^{-1}$.

Scheme 9

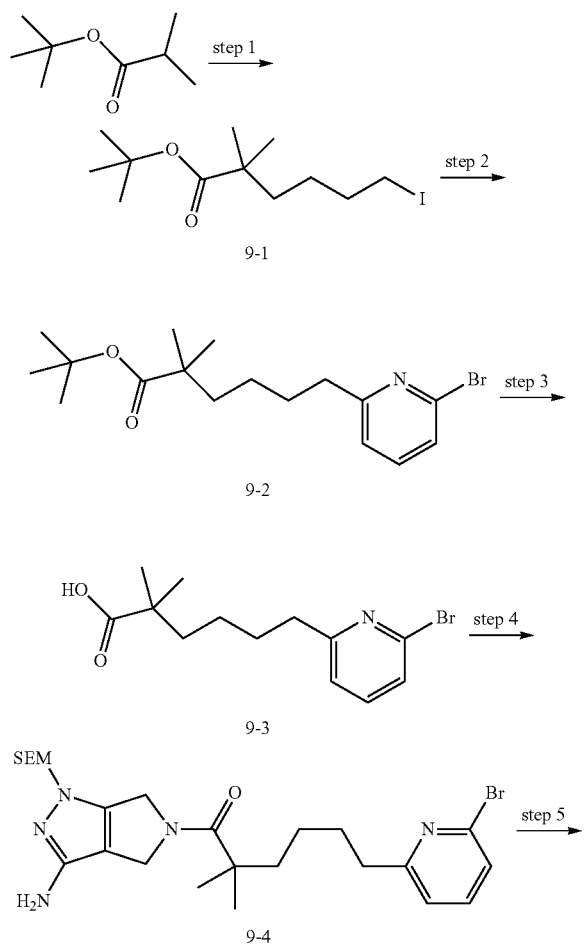

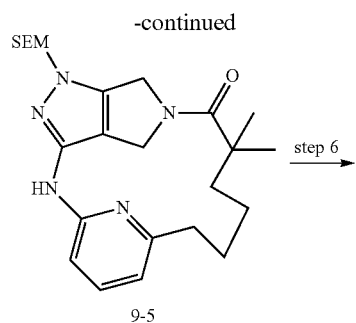

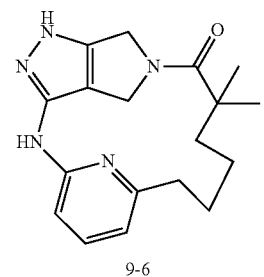

Step 1:

To a solution of LDA (22 mmol, prepared according the protocol in step 3 in Scheme 5) in THF (30 mL) at −78° C. was added isobutyric acid t-butyl ester (2.85 g, 20 mmol) in THF (10 mL) dropwise. The reaction mixture was stirred at −78° C. for 10 min. HMPA (3.48 mL, 20 mmol) was added. After stirring for an additional 10 min at −78° C., the resulting solution was cannulated to a solution of 1,4-diiodobutane (7.9 mL, 60 mmol) in THF (10 mL) at −78° C. After the addition, the dry ice-acetone bath was removed. The reaction mixture was stirred at room temperature for 1.5 h, diluted with brine, and extracted with EtOAc (3×). The combined organic layer was dried (Na$_2$SO$_4$), filtered, and concentrated. The residue was purified by flash column chromatography with EtOAc/hexane (0% to 6% gradient over 20 min) to give 3.5 g of 9-1 as a pale yellow oil (52% yield).

$^1$HNMR (CDCl$_3$, 300 Hz): 3.19 (t, J=6.4 Hz, 2H), 1.86-1.76 (m, 2H), 1.50-1.30 (m, 4H), 1.45 (s, 9H), 1.13 (s, 6H); $^{13}$CNMR (CDCl$_3$, 75 Hz): 177.0, 79.7, 42.5, 39.5, 33.9, 28.0, 25.9, 25.2, 6.6; EA calcd for C13H25IO2: C, 45.89; H. 7.41. Found: C, 45.26; H, 7.28; IR (neat); 3426, 2930, 1708, 1612, 1536, 1487, 1454, 1242, 1215, 1175, 1123, 914, 796, 770 cm$^{-1}$.

Step 2:

To a suspension of Zn (0.312 g, 4.8 mmol) in THF (1.5 mL) at room temperature was added dibromoethane (40 μL). The mixture was stirred at 65° C. for 3 min and cooled to room temperature. TMSCl (55 μL) was added. After stirring at room temperature for 20 min, iodide 9-1 (1.5 g, 4.6 mmol) in THF (3 mL) was added. The reaction mixture was stirred at 40° C. for 3 h, 48° C. for 1 h, 55° C. for 1 h, and then cooled to room temperature.

In a separate flask, Pd$_2$(dba)$_3$ (0.11 g, 0.115 mmol) and tris(2-furyl)phosphine (0.12 g, 0.46 mmol) were dissolved in THF (1.5 mmol) under Ar and stirred at room temperature for 20 min.

To a flask containing 1,5-dibromopyridine (2.18 g, 9.2 mmol) at room temperature under Ar was added the above prepared zinc reagent and palladium catalyst. The reaction was heated at 65° C. for 8 h. After cooling to room temperature, the mixture was diluted with brine and extracted with EtOAc (3×). The combined organic layer was dried (Na$_2$SO$_4$), filtered, and concentrated. The residue was purified by flash column chromatography with EtOAc/hexane (1% to 6% gradient over 30 min) to give 0.67 g of 9-2 as a pale yellow oil (41% yield). $^1$HNMR (CDCl$_3$, 500 Hz): 7.43 (t, J=7.7 Hz, 1H), 7.28 (d, J=7.7 Hz, 1H), 7.08 (d, J=7.5 Hz, 1H), 2.75 (t, J=7.8 Hz, 2H), 1.72-1.66 (m, 2H), 1.54-1.48 (m, 2H), 1.41 (s, 9H), 1.33-1.27 (m, 2H), 1.12 (s, 6H); $^{13}$CNMR (CDCl$_3$, 125 Hz): 177.3, 164.0, 141.5, 138.5, 125.2, 121.5, 79.6, 42.6, 40.5, 37.9, 30.2, 28.0, 25.2, 24.6.

Step 3:

Followed step 4 in Scheme 5 with 0.65 g of 9-2 as starting material. MS calcd for C18H29BrNO2 [M+H]$^+$: 302. Found: 302.

Step 4:

Followed step 5 in Scheme 5. 0.145 g of 9-4 was obtained (15% yield over two steps). $^1$HNMR (CDCl$_3$, 300 Hz): 7.41 (t, J=7.6 Hz, 1H), 7.26 (d, J=7.8 hz, 1H), 7.05 (d, J=7.5 Hz, 1H), 5.31 (s, 2H), 4.67-4.45 (br m, 4H), 3.90 (s, 1H), 3.60 (t, J=8.4 Hz, 2H), 2.73 (t, J=7.6 Hz, 2H), 1.72-1.64 (m, 4H), 1.36-1.30 (m, 2H), 1.28 (s, 6H), 0.93 (t, J=8.2 Hz, 2H), 0 (s, 9H); $^{13}$CNMR (CDCl$_3$, 75 Hz): 177.7, 165.2, 155.5, 153.3, 142.9, 140.5, 140.0, 126.6, 122.9, 104.5, 102.6, 67.6, 49.4, 48.5, 48.2, 47.4, 44.3, 41.2, 39.2, 31.7, 27.6, 26.0, 19.4, 0; HRMS calcd for C24H39BrN5O2Si [M+H]$^+$: 538.2034. Found: 538.2029; IR (neat): 2924, 2253, 911, 741, 650 cm$^{-1}$.

Step 5:

Followed step 6 in Scheme 5 except heating the reaction at 105° C. for 5 h. Compound 9-5 was obtained as a yellow oil (40 mg, 37% yield). $^1$HNMR (CDCl$_3$, 300 Hz): 7.45 (t, J=7.7 Hz, 1H), 6.79 (s, 1H), 6.65 (d, J=7.3 Hz, 1H), 6.48 (d, J=8.1 Hz, 1H), 5.40 (s, 2H), 4.96 (s, 2H), 4.66 (s, 2H), 3.62 (t, J=8.3 Hz, 2H), 2.63 (t, J=8.3 Hz, 2H), 1.77-1.72 (, 2H), 1.60-1.53 (m, 2H), 1.49-1.43 (m, 2H), 1.26 (s, 6H), 0.93 (t, J=8.2 Hz, 2H); $^{13}$CNMR (CDCl$_3$, 125 Hz): 178.3, 162.8, 154.0, 153.6, 139.8, 134.3, 115.8, 111.9, 108.1, 79.5, 67.8, 50.7, 49.6, 44.7, 39.7, 38.5, 29.0, 28.6, 23.1, 19.3, 0; HRMS calcd for C25H40N5O2Si [M+H]$^+$: 470.2951. Found: 470.2941.

Step 6:

Followed step 7 in Scheme 5. Compound 9-6 was obtained as a pale-yellow solid (20 mg, 70% yield, >98% purity based on absorption at 190-400 nM range after separation on an agilent SB-C18 2.1×35 mm column). $^1$HNMR (DMSO-d$_6$ with TFA vapor, 500 Hz): 7.77 (br s, 1H), 6.90-6.82 (m, 2H), 4.52 (s, 2H), 4.46 (s, 2H), 2.72-2.68 (m, 2H), 1.78-0.172 (m, 2H), 1.63 (t, J=7.6 Hz, 2H), 1.43-1.38 (m, 2H), 1.11 (s, 6H); $^{13}$CNMR (DMSO-d$_6$ with TFA vapor, 125 Hz): 176.1, 152.8, 149.8, 141.5, 136.9, 114.3, 111.7, 111.6, 110.0, 47.3, 45.9, 35.2, 31.7, 28.6, 26.1, 21.9; HRMS calcd for C18H24N5O [M+H]$^+$: 326.1975. Found: 326.1967.

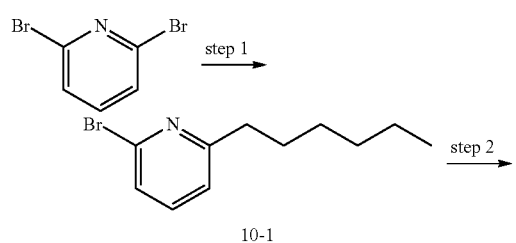

Scheme 10

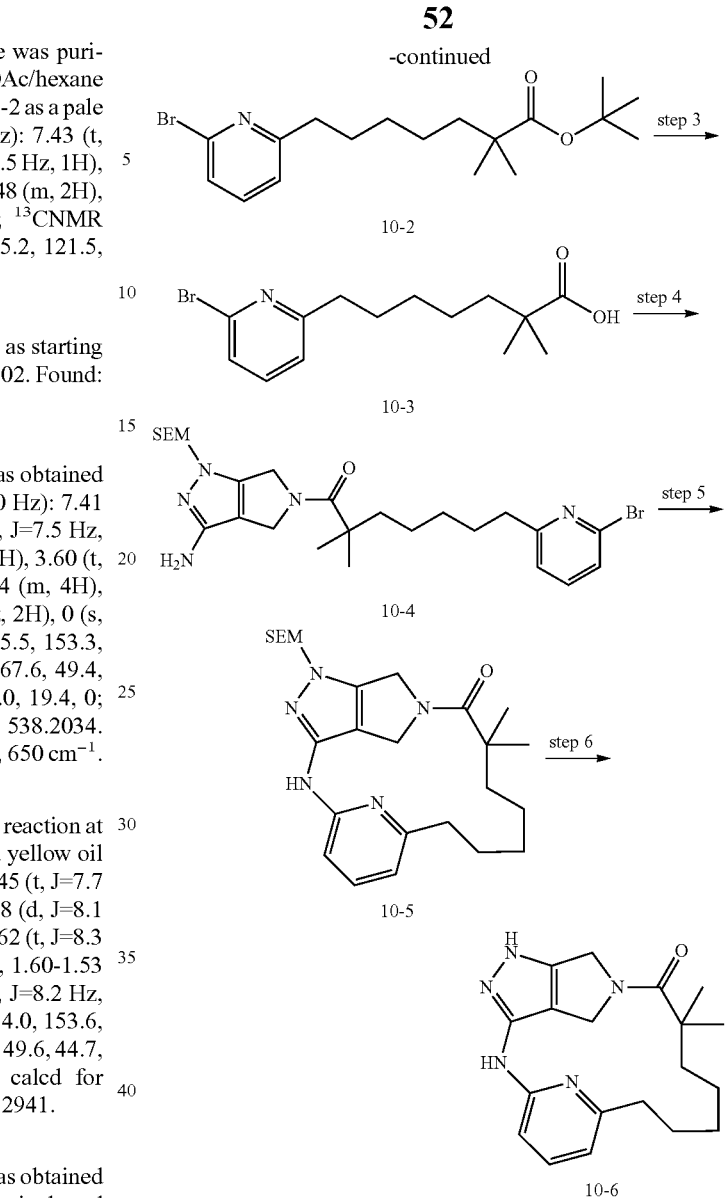

Step 1:

To a solution of n-BuLi (2.5 M in hexane, 1.12 mL) in THF (3 mL) at −78° C. was added a solution of 2,5-dibromopyridine (0.664 g) in THF (4 mL) dropwise. After the addition, the resulting dark green solution was stirred for an additional 15 min at −78° C. and then cannulated to a solution of 1,5-diiodopentane (2.28 g, 7.0 mmol) in THF at room temperature. The mixture was stirred at room temperature for 40 min during which it turned orange. The content was poured into brine and extracted with EtOAc (3×). The combined organic layer was dried (Na$_2$SO$_4$), filtered, and concentrated. The residue was purified by flash column chromatography with EtOAc/hexane (1% to 6% gradient over 20 min) to give 0.61 g of 10-1 as a pale yellow oil (61% yield). $^1$HNMR (CDCl$_3$, 300 Hz): 7.45 (t, J=7.8 hz, 1H), 7.30 (dd, J=0.9, 7.8 Hz, 1H), 7.09 (dd, J=0.9, 7.5 Hz), 3.19 (t, 7.0 Hz, 2H), 2.77 (t, J=7.5 Hz, 2H), 1.91-1.69 (m, 4H), 1.52-1.41 (m, 2H); $^{13}$CNMR (CDCl$_3$, 75 Hz): 164.1, 142.1, 139.0, 125.7, 122.0, 38.1, 33.6, 30.5, 29.0, 7.3; MS calcd for C10H14BrIN [M+H]$^+$: 354. Found: 354.

Step 2:

To a solution of LDA in THF (5 mmol, 1.0 M in THF) at −78° C. was added a solution of isobutyric acid t-butyl ester (0.72 g, 5 mmol) in THF (5 mL) dropwise. The resulting solution was stirred at −78° C. for 10 min. HMPA (0.43 mL, 2.5 mmol) was added via syringe. The reaction mixture was stirred for an additional 10 min. A solution of iodide 10-1 in THF (4 mL+2×1 mL rinse) was added via syringe. The reaction mixture turned orange upon addition of the iodide. After stirring for an additional 30 min at −78° C., the reaction was quenched with 2 mL of saturated aqueous NH$_4$Cl. The mixture was warmed to room temperature, diluted with 1/1 brine/saturated aqueous NaHCO$_3$, and extracted with EtOAc (2×). The combined organic layer was dried (Na$_2$SO$_4$), filtered, and concentrated. The residue was purified by flash column chromatography with EtOAc/hexane (1% to 6% gradient over 20 min) to give 0.49 g of 10-2 as a clear oil (contaminated by ~13% iodide 10-1 estimated by LCMS analysis). MS calcd for C18H29BrNO2 [M+H]$^+$: 370. Found: 370.

Step 3:

Followed step 4 in Scheme 5 with the product from step 2. MS calcd for C14H21BrNO2 [M+H]$^+$: 314. Found: 314.

Step 4:

Followed step 5 in Scheme 5 with the crude product from step 3. Compound 10-4 was obtained as a off-white foam (0.29 g). $^1$HNMR (CDCl$_3$, 300 Hz): 7.41 (t, J=7.7 Hz, 1H), 7.27 (d, J=7.0 Hz, 1H), 7.05 (d, J=7.4 Hz, 1H), 5.31 (s, 2H), 4.65-4.48 (br, 2H), 3.90 (s, 2H), 3.63-3.58 (m, 2H), 2.69 (t, J=7.6 Hz, 2H), 1.72-1.58 (m, 4H), 1.33-1.28 (m, 4H), 1.28 (s, 6H), 0.95-0.90 (m, 2H); $^{13}$CNMR (CDCl$_3$, 75 Hz): 177.8, 165.9, 165.4, 142.9, 140.5, 139.9, 139.0, 133.5, 126.6, 123.2, 122.8, 67.6, 48.3, 44.3, 41.4, 39.3, 31.2, 30.9, 27.6, 26.2, 19.2, 0; IR (neat): 2917, 2253, 1606, 1554, 1470, 1378, 1092, 908, 734, 650 cm$^{-1}$; HRMS calcd for C25H41BrN5O2Si [M+H]$^+$: 552.2191. Found: 552.2173.

Step 5:

Followed step 5 in Scheme 9. Compound 10-5 was obtained as a yellow powder (166 mg, 70% yield after flash column chromatography with EtOAc/hexane (40% to 100% gradient over 20 min). $^1$HNMR (CDCl$_3$, 500 Hz): 7.44 (t, J=7.7 Hz, 1H), 6.79 (s, 1H), 6.65 (d, J=7.3 Hz, 1H), 6.49 (d, J=8.1 Hz, 1H), 5.40 (s, 2H), 4.96 (s, 2H), 4.66 (s, 2H), 3.62 (t, J=8.3 Hz, 2H), 2.63 (t, J=8.3 Hz, 2H), 1.78-1.70 (m 2H), 1.58-1.52 (, 2H), 1.49-1.43 (m 2H), 1.26 (s, 6H), 0.93 (t, J=8.2 Hz, 2H); $^{13}$CNMR (CDCl$_3$, 125 Hz): 178.3, 162.8, 154.0, 153.6, 139.8, 134.3, 115.8, 111.9, 108.1, 79.5, 67.8, 50.7, 49.6, 44.7, 39.7, 38.5, 29.0, 28.6, 23.1, 19.3, 0; IR (neat): 2918, 2253, 1600, 1468, 1380, 1094, 908, 731, 650 cm$^{-1}$; HRMS calcd for C25H40N5O2Si [M+H]$^+$: 470.2946. Found: 470.2935.

Step 6:

Followed step 7 in Scheme 5. Compound 10-6 was obtained as a off-white powder (58 mg, 50% yield). Mp: 265-270° C.; $^1$HNMR (DMSO-d$_6$ with TFA vapor, 500 Hz): 7.68-7.62 (m, 1H), 6.78 (d, J=8.4 Hz, 1H), 6.75 (d, J=7.2 Hz, 1H), 4.78 (s, 2H), 4.53 (s, 2H), 2.51 (t, J=1.7 Hz, 2H), 1.68 (d, J=7.7 Hz, 2H), 1.44-1.34 (m, 4H), 1.16 (s, 6H); $^{13}$CNMR (DMSO-d$_6$ with TFA vapor, 125 Hz): 175.4, 158.0, 153.0, 146.0, 140.5, 137.5, 113.2, 111.1, 108.7, 48.3, 47.1, 42.6, 37.7, 34.3, 27.1, 26.8, 21.4; IR (KBr): 3280, 2926, 2867, 1604, 1529, 1492, 1454, 1393, 1360, 1330, 1305, 1241, 1227, 1209, 1155, 801, 764, 738, 717, 633 cm$^{-1}$; HRMS calcd for C19H26N5O [M+H]$^+$: 340.2132. Found: 340.2129.

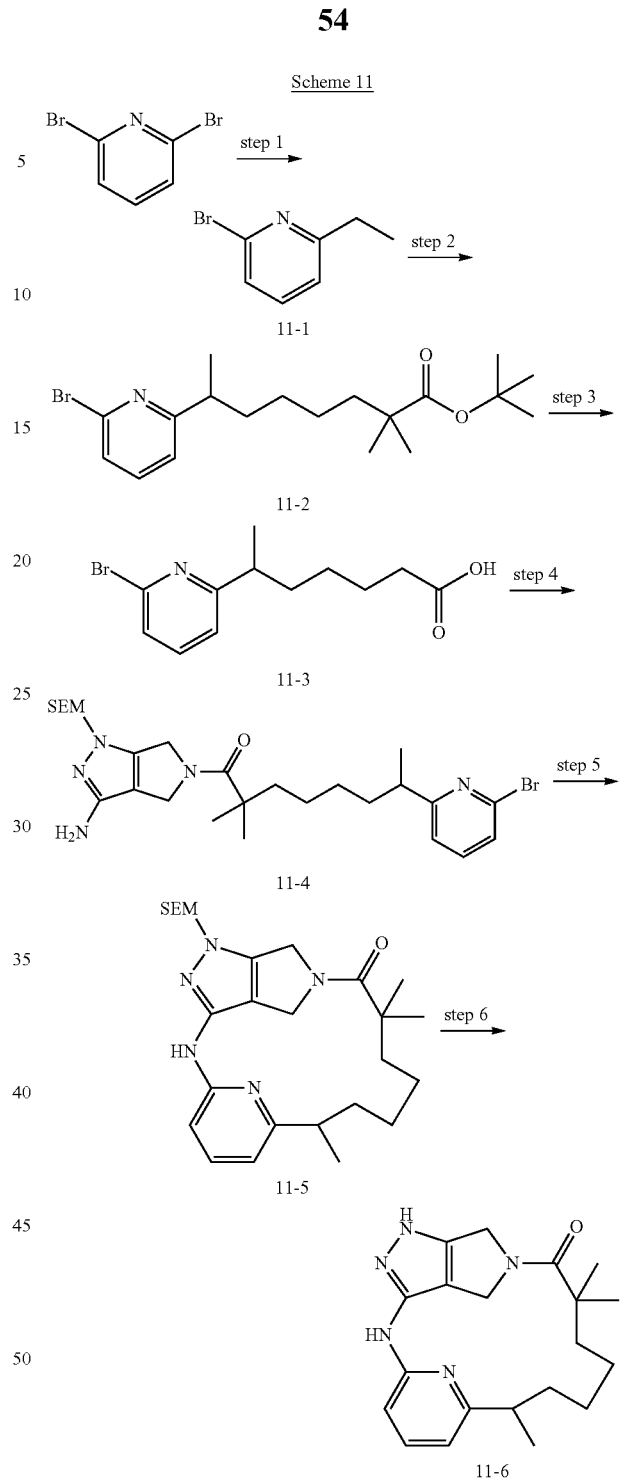

Scheme 11

Step 1:

Followed step 1 in Scheme 10 except replacing 1,5-diiodopentane with iodoethane. Compound 11-1 was obtained as a yellow oil (5.4 g, 90% yield). $^1$HNMR (CDCl$_3$, 300 Hz): 7.44 (t, J=7.6 Hz, 1H), 7.29 (d, J=7.9 Hz, 1H), 7.10 (d, J=7.6 Hz, 1H), 2.80 (q, J=7.6 Hz, 2H), 1.29 (t, J=7.6 Hz, 3H); $^{13}$CNMR (CDCl$_3$, 75 Hz): 165.3, 141.5, 138.6, 125.2, 120.7, 31.1, 13.7; MS calcd for C7H9BrN [M+H]$^+$: 186. Found: 186; IR (neat): 2970, 2935, 2876, 1582, 1553, 1462, 1436, 1405, 1371, 1226, 1160, 1128, 1089, 1045, 985, 819, 800, 735, 665 cm$^{-1}$.

Step 2:

To a solution of LDA (6.6 mmol) in THF (10 mL) at −78° C. was added compound 11-1 (1.12 g, 6 mmol) in THF (4 mL+1 mL rinse). The resulting deep orange solution was stirred at −78° C. for 5 min. Then a solution of iodide 9-1 (2.35 g, 7.2 mmol) in THF (6 mL+2 mL rinse) was added. The reaction mixture was warmed to room temperature overnight, poured into brine and extracted with EtOAc (3×). The combined organic layer was dried (Na$_2$SO$_4$), filtered and concentrated. Purification of the residue with flash column chromatography with EtOAc in hexane (1% to 8% gradient over 20 min) followed by distillation gave 0.37 g of the desired product 11-2 as an orange oil (37% yield).

$^1$HNMR (CDCl$_3$, 300 Hz): 7.43 (t, J=7.7 Hz, 1H), 7.27 (dd, J=0.9, 7.8 Hz, 1H), 7.06 (dd, J=0.9, 7.5 Hz, 1H), 2.89-2.77 (m, 1H), 1.75-1.64 (m, 1H), 1.62-1.48 (m, 1H), 1.45-1.38 (m 12H), 1.30-1.13 (m, 7H), 1.08 (s, 6H); $^{13}$CNMR (CDCl$_3$, 75 Hz): 177.4, 168.6, 141.6, 138.5, 125.3, 120.1, 79.6, 42.6, 41.8, 40.6, 36.8, 28.1, 28.0, 25.2, 25.0, 20.6; MS calcd for C$_{19}$H$_{31}$BrNO$_2$ [M+H]$^+$: 386. Found: 386.

Step 3:

Followed step 4 in Scheme 5. MS calcd for C$_{12}$H$_{17}$BrNO$_2$ [M+H]$^+$: 330. Found: 330.

Step 4:

Followed step 5 in Scheme 5. Compound 11-4 was obtained as a pale yellow thick oil (0.53 g, quantitative yield over two steps). $^1$HNMR (CDCl$_3$, 500 Hz): 7.38 (t, J=7.6 Hz, 1H), 7.23 (dd, J=0.9, 77. Hz, 1H), 7.01 (dd, J=0.8, 7.5 Hz, 1H), 5.30 (s, 2H), 4.65-4.45 (br m, 4H), 3.80 (s, 2H), 3.61 (dd, J=8.1, 9.2 Hz, 2H), 2.84-2.77 (m, 1H), 1.72-1.64 (m, 1H), 1.58-1.50 (, 2H), 1.27-1.22 (m, 4H), 1.26 (s, 6H), 1.23 (d, J=7.0 Hz, 3H), 1.18-1.08 (m, 1H), 0.93 (t, J=8.4 Hz, 2H), 0 (s, 9H); $^{13}$CNMR (CDCl$_3$, 125 Hz): 176.4, 168.4, 154.1, 141.5, 138.6, 125.3, 120.1, 103.1, 101.3, 66.2, 47.0, 42.9, 41.8, 40.0, 36.7, 28.1, 26.2, 24.9, 20.6, 17.8, 0, −1.4; HRMS calcd for C$_{26}$H$_{43}$BrN$_5$O$_2$Si [M+H]$^+$: 564.2364. Found: 564.2350; IR (neat): 2916, 2253, 907, 732, 650 cm$^{-1}$.

Step 5:

Followed step 5 in Scheme 9. Compound 11-5 was obtained as yellow solid (140 mg, 58% yield). $^1$HNMR (CDCl$_3$, 400 Hz): 7.51 (t, J=7.8 Hz, 1H), 6.70 (d, J=7.6 Hz, 1H), 6.69 (s, 1H), 5.46 (d, J=11.5 Hz, 1H), 5.34 (d, J=11.5 Hz, 1H), 4.96 (d, J=11.9 Hz, 1H), 4.75-4.69 (m, 2H), 4.59 (d, J=15.3 Hz, 1H), 3.67-3.55 (m, 2H), 2.80-2.71 (m, 1H), 2.15-2.05 (m, 1H), 1.82-1.73 (m, 1H), 1.68-1.25 (m, 6H), 1.29 (s, 3H), 1.23 (d, J=6.7 Hz, 3H), 1.21 (s, 3H), 0 (s, 9H); HRMS calcd for C$_{26}$H$_{42}$N$_5$O$_2$Si [M+H]$^+$: 484.3102. Found: 484.3088.

Step 6:

Followed step 7 in Scheme 5. Compound 11-6 was obtained as a yellow powder (70 mg, 74% yield). $^1$HNMR (DMSO-d$_6$, 500 Hz): 12.01 (s, 1H), 9.12 (s, 1H), 7.48-7.42 (m, 1H), 6.58-6.54 (m, 2H), 4.87-4.80 (m, 1H), 4.76-4.71 (m, 1H), 4.54-4.36 (m, 2H), 2.64-2.58 (m, 1H), 2.08-2.00 (m, 1H), 1.75-1.68 (m, 1H), 1.59-1.51 (m, 1H), 1.45-1.25 (m, 5H), 1.17 (s, 3H), 1.16 (d, J=5.4 Hz, 3H), 1.12 (s, 3H); $^{13}$CNMR (DMSO-d$_6$, 125 Hz): 175.2, 164.8, 154.3, 151.2, 142.2, 140.7, 137.8, 112.5, 108.8, 106.8, 48.5, 47.2, 42.6, 38.2, 35.0, 27.9, 26.6, 25.5, 21.6, 17.9; HRMS calcd for C$_{20}$H$_{28}$N$_5$O [M+H]$^+$: 354.2288. Found: 354.2282. IR (KBr): 3274, 2961, 2928, 2867, 1608, 1533, 1455, 1397, 1362, 1314, 1245, 1204, 1157, 1091, 1062, 989, 795, 742, 633 cm$^{-1}$.

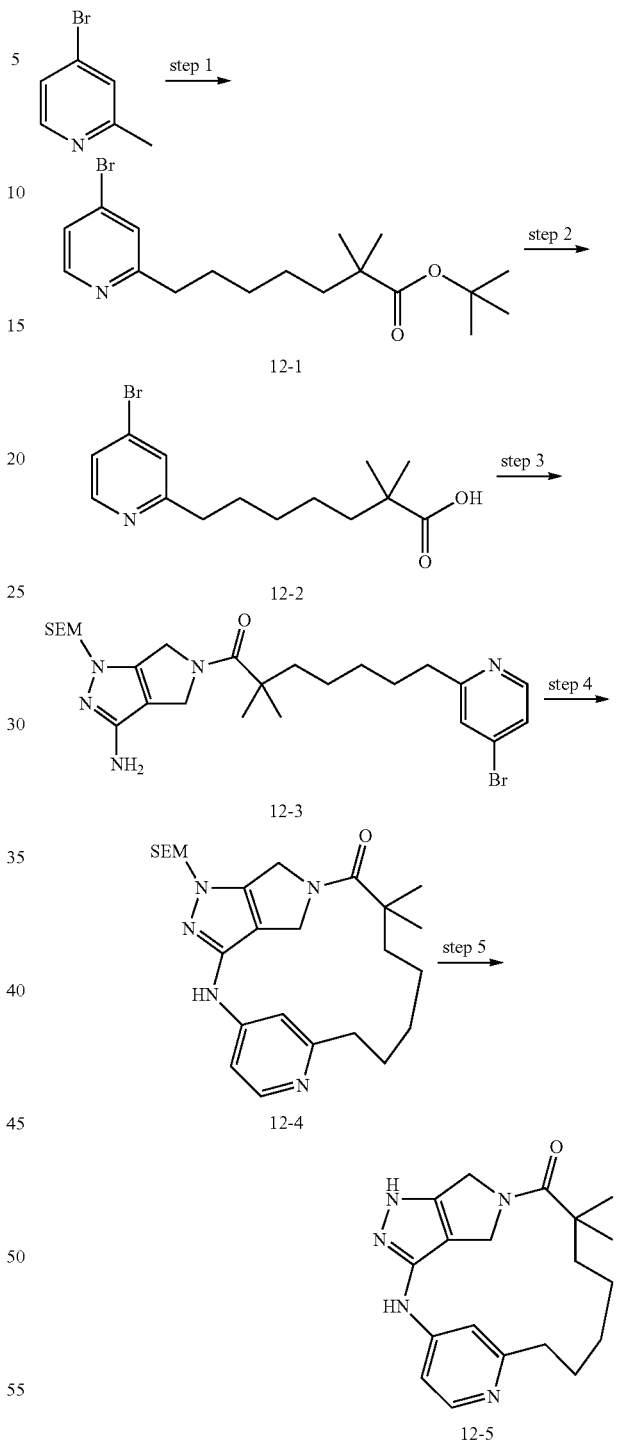

Scheme 12

Step 1:

Follow step 2 in Scheme 11. Compound 12-1 was obtained as a yellow oil (1.3 g, 36% yield). $^1$HNMR (CDCl$_3$, 300 Hz): 8.33 (d, J=5.7 Hz, 1H), 7.32 (d, J=1.8 hz, 1H), 7.27 (dd, J=1.8, 5.6 Hz, 1H), 2.74 (t, J=7.6 Hz, 2H), 1.85-1.19 (m, 8H), 1.42 (s, 9H), 1.10 (s, 6H); $^{13}$CNMR (CDCl$_3$, 75 Hz): 177.3, 164.0, 150.0, 132.9, 126.0, 124.3, 79.6, 42.6, 40.6, 38.1, 29.9, 29.5, 28.0, 25.2, 24.8; MS calcd for C$_{18}$H$_{29}$BrNO$_2$ [M+H]$^+$: 370.

Found: 370. IR (neat): 2975, 2934, 2859, 1722, 1570, 1551, 1467, 1388, 1366, 1322, 1252, 1213, 1147, 1091, 853, 819, 683 cm$^{-1}$.

Step 2:

Followed step 4 in Scheme 5. The crude product was used in the next step. MS calcd for C14H21BrNO2 [M+H]$^+$: 314. Found: 314.

Step 3:

Followed step 5 in Scheme 5. Compound 12-3 was obtained as a pale yellow oil (0.53 g, 97% yield over two steps). MS calcd for C25H41BrN5O2Si [M+H]$^+$: 552. Found: 552.

Step 4:

Followed step 5 in Scheme 9. Compound 12-4 was obtained as a yellow foam (0.25 g, 56% yield). $^1$HNMR (CDCl$_3$, 500 Hz): 8.32 (d, J=5.6 Hz, 1H), 6.57 (dd, J=2.1, 5.6 Hz, 1H), 6.38 (dd, J=2.2 Hz, 1H), 6.11 (s, 1H), 5.40 (s, 2H), 4.70 (s, 2H), 4.44 (s, 2H), 3.59 (t, J=8.3 Hz, 2H), 2.75 (t, J=6.3 Hz, 2H), 1.85-1.80 (m, 2H), 1.55-1.48 (m, 2H), 1.40-1.32 (m, 2H), 1.25-1.18 (m, 2H), 1.24 (s, 6H), 0.93 (t, J=8.4 Hz, 2H), 0 (s, 9H); $^{13}$CNMR (CDCl$_3$, 125 Hz): 176.6, 163.1, 152.9, 150.5, 148.8, 131.9, 112.1, 108.7, 107.3, 77.4, 66.8, 47.8, 46.3, 44.3, 41.0, 36.1, 28.2, 27.9, 26.9, 24.4, 17.9, −1.4; HRMS calcd for C25H40N5O2Si [M+H]$^+$: 470.2946. Found: 470.2929; IR (neat): 2916, 2253, 1597, 1381, 908, 734, 650 cm$^{-1}$.

Step 5:

Followed step 7 in Scheme 5. Compound 12-5 was obtained as a light yellow solid (20 mg, 12% yield). $^1$HNMR (DMSO-d$_6$, 500 Hz): 12.60-12.40 (m, 1H), 8.92 (s, 1H), 8.15 (s, 1H), 6.61 (s, 1H), 6.27 (s, 1H), 4.58-4.42 (m, 2H), 4.38 (s, 2H), 2.59 (t, J=5.9 Hz, 2H), 1.73-1.68 (m, 2H), 1.57-1.52 (m, 2H), 1.34-1.28 (m, 2H), 1.13 (s, 6H), 1.13-1.08 (m, 2H); HSQC, HMBC and COSY are constisant with the structure assignment; HRMS calcd for C19H26N5O [M+H]$^+$: 340.2132. Found: 340.2126.

Scheme 13

Step 1:

To a mixture of 3-methyl-pentane-1,5-diol (5.9 g, 50 mmol) and red phosphorus (1.49 g, 47.9 mmol), stirred and cooled in ice, was added iodine (14.9 g, 58.4 mmol) during a period of 1 h. The mixture was stirred for 1 h at ice-bath temperature and for 10 hours at 28° C. After standing for an additional 4.5 hours at room temperature, the brown-black paste was heated with stirring at 40-45° C. for 1.5 hours and allowed to stand for 24 hours. The mixture was extracted with 120 mL of ethyl ether and the ether solution was washed with 80 mL of water, 40 mL of dilute sodium hydroxide, again with 80 mL of water and dried. The ether was removed under reduced pressure and the residue was distilled to give compound 13-1 (14.8 g, 87%) as a yellow oil. $^1$H NMR (300 MHz, CDCl$_3$) δ 3.28-3.14 (m, 4H), 1.91-1.85 (m, 2H), 1.72-1.65 (m, 3H), 0.90 (d, 3H, J=3.6 Hz). GC-MS: 338, t$_R$=8.78 min.

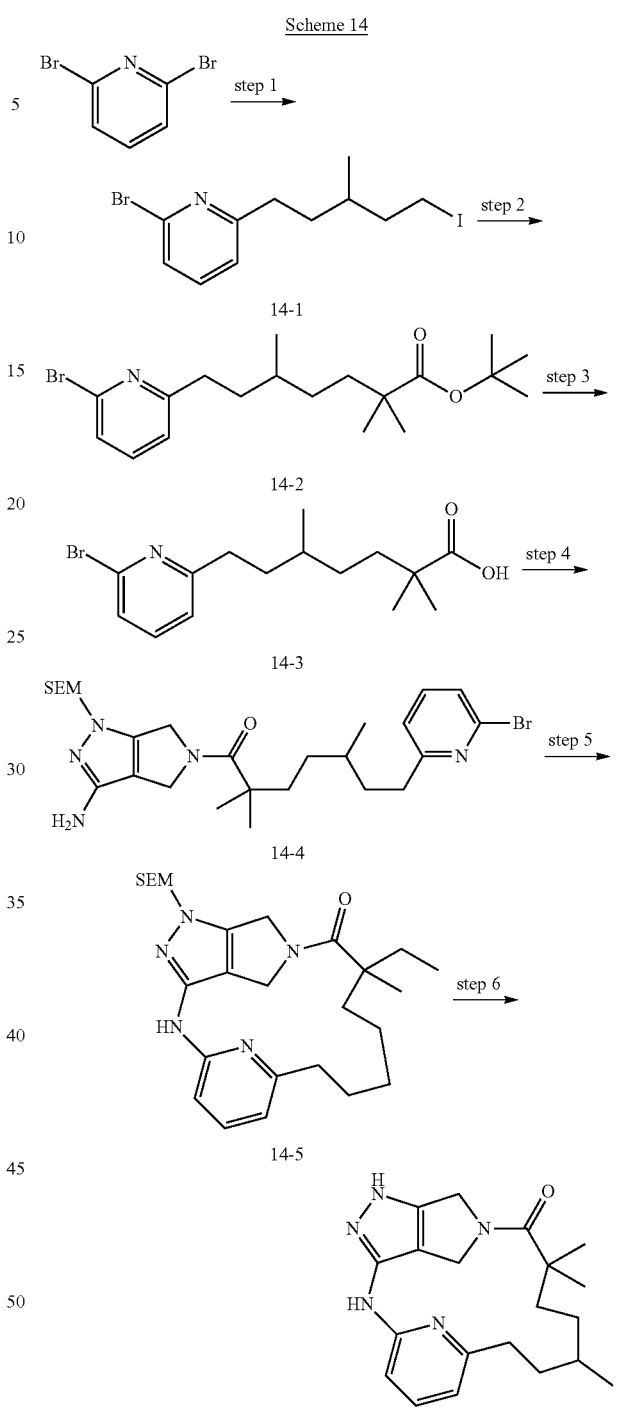

Scheme 14

Step 1:

To a solution of n-BuLi (2.5 M in hexane, 6.8 mL, 17 mmol) in THF (38 mL) at −78° C. was added dropwise 2,6-dibromopyridine (4 g, 17 mmol) in THF (26 mL). After completion of the addition, the resulting dark green solution was stirred for additional 15 min. The solution was cannulated to a solution of 13-1 (8.6 g, 25.5 mmol) in THF (13 mL) at room temperature. After stirring at room temperature for 40 min, the reaction mixture was poured into brine and extracted with ethyl acetate (70 mL×3). The combined organic layers were dried over sodium sulfate, filtered and concentrated. The residue was purified by column chromatography on silica gel (petroleum ether/ethyl acetate=20:1) to give 14-1 (2.0 g, 32%) as a yellow oil. $^1$H NMR (300 MHz, CDCl$_3$) δ 7.45 (t, 1H, J=8.1 Hz), 7.30 (d, 1H, J=7.8 Hz), 7.10 (d, 1H, J=7.8 Hz), 3.27-3.15 (m, 2H), 2.85-2.70 (m, 5H), 2.01-1.85 (m, 1H), 1.74-1.69 (m, 4H), 0.96 (d, 3H, J=6.3 Hz). LC-MS: 368 [M+1]$^+$, $t_R$=1.84 min.

Step 2:

To a solution of diisopropyl amine (1.11 mL, 8 mmol) in THF (18 mL) at −78° C. was added n-BuLi (2.5 M in hexane, 2.9 mL, 1.26 mmol). The dry ice-acetone bath was removed after the addition. The reaction mixture was stirred for 10 min and then cooled to −78° C. A solution of isobutyric acid tert-butyl ester (942 mg, 6.5 mmol) in THF (5 mL) was added to the above prepared LDA solution dropwise at −78° C. After the addition, HMPA (0.32 mL) was added, the mixture was stirred at −78° C. for 15 minutes and warmed to 0° C. for 30 minutes. The mixture was cooled to −78° C. and a solution of 14-1 (2.0 g, 5.5 mmol) in THF (3 mL) was added dropwise, then the mixture was stirred at −78° C. for 30 minutes and stirred at room temperature for 2 hours. The reaction was quenched with saturated aqueous NH$_4$Cl solution. The mixture was warmed to room temperature, diluted with saturated aqueous sodium bicarbonate and brine (1/1), and extracted with ethyl acetate (30 mL×3). The combined organic layers were dried over sodium sulfate, filtered and concentrated. The residue was purified by column chromatography on silica gel (petroleum ether/ethyl acetate=20:1) to give compound 14-2 (1.0 g, 48%) as a yellow oil. $^1$H NMR (300 MHz, CDCl$_3$) δ 7.43 (t, 1H, J=7.8 Hz), 7.28 (d, 1H, J=7.5 Hz), 7.08 (d, 1H, J=7.5 Hz), 2.85-2.65 (m, 2H), 1.80-1.20 (m, 5H), 1.20-1.10 (m, 7H), 0.93 (d, 3H, J=6.3 Hz). LC-MS: 384 [M+1]$^+$, $t_R$=2.10 min.

Step 3:

A solution of compound 14-2 (500 mg, 1.3 mmol) in hexafluoroisopropanol (6 mL) under nitrogen was heated in microwave reactor at 155° C. for 1.5 h. After cooling to room temperature, the solvent was removed under reduced pressure to give the residue (0.43 g, crude) which was used for next step without further purification. LC-MS: 328 [M+1]$^+$, $t_R$=1.70 min Step 4:

To a mixture of the above prepared acid 14-3, amine 1-7 (430 mg, 1.3 mmol), EDCI (304 mg, 1.59 mmol) and HOBT hydrate (214 mg, 1.59 mmol) under nitrogen was added dichloromethane (10 mL) and DIEA (376 mg, 2.92 mmol) sequentially. The reaction mixture was stirred at room temperature overnight, diluted with saturated aqueous sodium bicarbonate (30 ml), and extracted with ethyl acetate (2×20 ml). The combined organic layer was dried over sodium sulfate, filtered and concentrated. The residue was purified by column chromatography on silica gel (2.0 g) eluting with (petroleum ether/ethyl acetate=1:1) to give compound 14-4 (388 mg, 53%) as a yellow oil. $^1$H NMR (300 MHz, CDCl$_3$) δ 7.44 (t, 1H, J=8.4 Hz), 6.65 (d, 1H, J=7.2 Hz), 6.50 (d, 1H, J=8.4 Hz), 5.41 (q, 2H), 5.08 (q, 2H), 4.65 (q, 2H), 3.66-3.59 (m, 2H), 2.75-2.45 (m, 2H), 2.03-1.98 (m, 2H), 1.73-1.52 (m, 5H), 1.28-1.22 (m, 7H), 0.97-0.91 (m, 5H), 0 (s, 9H). LC-MS: 564 [M+1]$^+$, $t_R$=1.78 min.

Step 5:

A mixture of compound 14-4 (776 mg, 1.38 mmol), Pd$_2$(dba)$_3$ (256 mg, 0.276 mmol, 20 mol %), XANTPHOS (197 mg, 0.414 mmol, 30 mol %), and sodium tert-butoxide (199 mg, 2.07 mmol) in a dry flask was evacuated and refilled with nitrogen three times. Freshly degassed toluene (500 mL) was added to the mixture via cannula. The reaction was heated at 105° C. for 8 h. After solvent was removed under reduced pressure, the residue was added brine and extracted with ethyl acetate (30 mL×3). The combined organic layers were dried over sodium sulfate, filtered and concentrated. The residue was purified by flash column chromatography on silica gel (petroleum ether/ethyl acetate=1:1) to give compound 14-5 (360 mg, 54%) as a yellow solid.

$^1$H NMR (300 MHz, CDCl$_3$) δ 7.51 (t, 1H, J=7.5 Hz), 6.72 (d, 1H, J=7.5 Hz), 6.56 (d, 1H, J=8.4 Hz), 5.52 (q, 2H), 5.13 (q, 2H), 4.74 (q, 2H), 3.72-3.66 (m, 2H), 2.80-2.50 (m, 2H), 1.80-1.40 (m, 8H), 1.34-1.28 (m, 7H), 1.05-0.98 (m, 6H), 0.0 (s, 9H). LC-MS: 484 [M+1]$^+$, $t_R$=1.94 min.

Step 6:

To a solution of compound 14-5 (360 mg, 0.75 mmol) in dichloromethane (4 mL) at room temperature was added trifluoroacetic acid (4 mL). The reaction was stirred at room temperature for 1.5 h and then quenched with ice-cooled saturated sodium bicarbonate. The mixture was basified to about pH ~9 with a saturated solution of sodium carbonate and extracted with dichloromethane (5 mL×3). The combined organic layer was dried over sodium sulfate, filtered and concentrated. The residue was purified by column chromatography on silica gel (DCM/MeOH=10:1) to give compound 14-6 (200 mg, 80%) as a yellow solid. $^1$H NMR (300 MHz, CD3OD) δ 7.33 (t, 1H, J=7.5 Hz), 6.51 (d, 1H, J=7.2 Hz), 6.46 (d, 1H, J=8.1 Hz), 5.06 (d, 1H, J=12 Hz), 4.67 (d, 2H, J=1.2 Hz), 4.50 (q, 2H), 2.58-2.45 (m, 2H), 1.92 (t, 1H, J=7.2 Hz), 1.68-1.23 (m, 6H), 1.22 (s, 3H), 1.21 (s, 3H), 0.88 (t, 3H, J=6.3 Hz). LC-MS: 354 [M+1]$^+$, $t_R$=4.82 min. HPLC: $t_R$=5.34 min, 98.8% (214 nm), 99% (254 nm).

Scheme 15

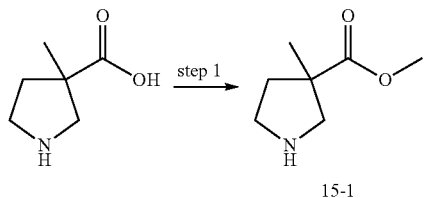

Step 1:

To 20 mL 0° C. methanol was added dropwise 1 mL SOCl$_2$, and the resulting mixture was stirred at 0° C. for 0.5 h. Then 0.5 g of 3-methyl-pyrrolidine-3-carboxylic acid was added and stirred for 20 h. The solvent was removed by evaporation to give compound 15-1 (714 mg) as a white solid. $^1$H NMR (300 MHz, CDCl$_3$): δ 10.08 (br s, 1H), 9.81 (br s, 1H), 3.76 (s, 3H), 3.53-3.36 (m, 2H), 3.20-3.12 (m, 2H), 2.51-2.43 (m, 2H), 2.00-1.90 (m, 1H), 1.45 (s, 3H). LC-MS: 144 [M+1]$^+$, $t_R$=0.414 min.

Scheme 16

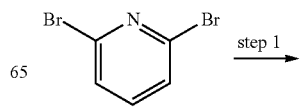

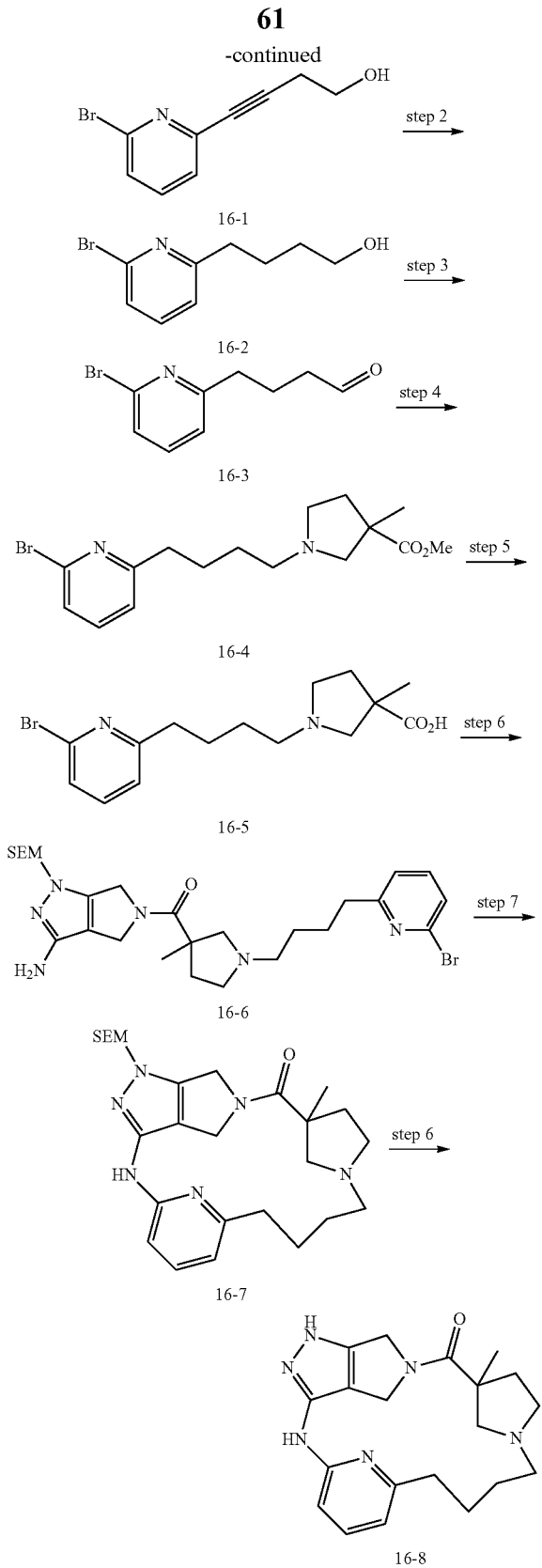

(0.29 g). The resulting reaction was stirred under $N_2$ at room temperature for 16 h. The reaction mixture was concentrated and redissolved in DCM (50 mL), washed with water (50 mL) and brine (50 mL), dried over $Na_2SO_4$ and concentrated. The residue was purified by silica gel column (petroleum ether/ethyl acetate=5:1 to 3:1) to give compound 16-1 (0.5 g, yield 44%) as a yellow oil. $^1$HNMR (300 MHz, $CDCl_3$): δ 7.51-7.46 (m, 1H), 7.41 (d, 1H, J=9.0 Hz), 7.34 (d, 1H, J=9.0 Hz), 3.87-3.85 (m, 2H), 2.72 (t, 3H, J=6.0 Hz). LC-MS: 226, 228 $[M+1]^+$, $t_R$=1.296 min.

Step 2:

To a solution of compound 16-1 (160 mg, 5 mmol) and $Et_3N$ (0.2 mL) in ethanol (15 mL) was added $PtO_2$ (16 mg). The resulting mixture was stirred under $H_2$ at room temperature for 2 h. The reaction mixture was filtered and concentrated in vacuo to give compound 16-2 (0.22 g, crude) as a yellow oil. LC-MS: 230, 232 $[M+1]^+$, $t_R$=1.323 min.

Step 3:

To a solution of compound 16-2 (220 mg, 1 mmol) in DCM (15 mL) was added Dess-Martin periodinane (466 mg, 1.1 mmol). The resulting mixture was stirred at 20° C. for 0.5 h. Then 1 M NaOH (15 mL) was added and stirred for 10 minutes. The organic layer was separated and washed with 15 mL 1 M NaOH and 15 mL brine, dried over anhydrous $Na_2SO_4$. filtered and evaporated to give crude product which was purified by silica gel column (petroleum ether/ethyl acetate=2:1) to give Compound 16-3 (128 mg, yield 56%). $^1$H NMR (300 MHz, $CDCl_3$): δ 9.79 (t, 1H, J=1.51 Hz), 7.47 (t, 1H, J=7.7 Hz), 7.33 (d, 1H, J=7.6 Hz), 7.12 (d, 1H, J=7.1 Hz), 2.81 (t, 2H, J=7.3 Hz), 2.55-2.50 (m, 2H), 2.55-2.50 (m, 2H), 2.13-2.03 (m, 2H), LC-MS: 228, 230 $[M+1]^+$, $t_R$=1.455 min.

Step 4:

To a solution of compound 16-3 (345 mg, 1.51 mmol) and 3-methylpyrrolidine-3-carboxylate hydrochloride (15-1) (327 mg, 1.82 mmol) in 10 mL MeOH was added $Et_3N$ (184 mg, 1.82 mmol), molecular sieves (0.8 g) and $NaBH_3CN$ (190 mg 3.03 mmol). The resulting mixture was stirred under $N_2$ at 20° C. for 20 h. Filtered and evaporated to give crude product which was purified by silica gel column (petroleum ether/ethyl acetate=1:2) to give compound 16-4 (449 mg, yield 84%).

$^1$H NMR (300 MHz, $CDCl_3$): δ 7.46-7.08 (m, 3H), 3.68 (s, 3H), 2.95 (d, 1H, J=9.4 Hz), 2.76 (t, 2H, J=7.6 Hz), 2.62-2.55 (m, 2H), 2.45-2.33 (m, 4H), 1.78-1.41 (m, 6H), 1.33 (m, 3H). LC-MS: 355, 357 $[M+1]^+$, $t_R$=1.217 min.

Step 5:

To a solution of compound 16-4 (449 mg, 1.26 mmol) in 15 mL water/15 mL dioxane was added NaOH (513 mg, 12.8 mmol). The resulting mixture was stirred at 20° C. for 20 h. Neutralized with HCl and evaporated. The residue was washed with 15 mL MeOH, filtered and the filtrate was evaporated to give crude compound 16-5 (0.68 g crude). LC-MS: 341, 343 $[M+1]^+$, $t_R$=1.180 min.

Step 6:

To a solution of the above prepared acid 16-5, amine 1-7 (375 mg, 1.48 mmol), EDCI (309 mg, 1.61 mmol) and HOBt (217 mg, 1.61 mmol) in 40 mL DCM was added DIEA (217 mg, 4.35 mmol). The resulting mixture was stirred at 20° C. for 20 h. Then the reaction was quenched with 35 mL saturated aqueous $NaHCO_3$, and extracted with ethyl acetate (50 mL×3). The combined organic layers were washed with brine and dried over $Na_2SO_4$. The solution was filtered and evaporated to give crude product which was purified by silica gel column (ethyl acetate/methanol=20:1+1% $Et_3N$) to give compound 16-6 (536 mg, yield 66%). $^1$H NMR (300 MHz, $CDCl_3$): δ 7.48-7.10 (m, 3H), 5.30 (s, 2H), 4.60-4.47 (m, 3H), 4.01 (s, 1H), 3.94 (s, 1H), 3.61-3.56 (m, 3H), 3.40-3.27 (m, Step 1:

To a solution of 2,6-dibromopyridine (1.18 g, 5 mmol) in anhydrous THF (20 mL) was added n-but-3-yn-1-ol (0.35 g, 5 mmol), CuI (95 mg, 0.5 mmol), $Et_3N$ (5 mL) and $Pd(PPh_3)_4$ 1H), 3.11-3.03 (m, 2H), 2.81-2.60 (m, 7H), 1.80-1.58 (m, 4H), 1.52-1.24 (m, 7H), 0.96-0.91 (m, 3H), 0.96-0.91 (m, 3H), 0.01 (s, 9H). LC-MS: 577, 579 [M+1]$^+$, $t_R$=1.499 min.

Step 7:

Under $N_2$, compound 16-6 (472 mg, 0.817 mmol), $Pd_2$(dba)$_3$ (70.8 mg, 0.123 mmol), XANTPHOS (141.6 mg, 0.245 mmol) and t-BuONa (110.4 mg 1.149 mmol) was stirred in 236 mL toluene at 105° C. for 20 h. Then the reaction mixture was cooled and quenched with 100 mL saturated sodium bicarbonate aqueous. The organic layer was separated and aqueous phase was extracted with ethyl acetate (200 mL×2). The combined organic layers were washed with brine and dried over anhydrous sodium sulfate. The solution was filtered and evaporated to give crude product which was purified by silica gel column (ethyl acetate+1% Et$_3$N) to give compound 16-7 (102 mg, yield 23%). $^1$H NMR (300 MHz, CDCl$_3$): δ 7.42 (t, 1H, J=7.8 Hz), 7.25 (s, 1H), 6.65 (d, 1H, J=7.26 Hz), 6.44 (d, 1H, J=8.1 Hz), 5.50-5.15 (m, 3H), 4.69-4.55 (m, 2H), 3.72-3.58 (m, 3H), 3.14-3.09 (m, 1H), 2.74-2.58 (m, 3H), 2.46-2.36 (m, 2H), 2.30-2.20 (m, 1H), 2.10 (d, 1H, J=10.2 Hz), 1.91-1.80 (m, 2H), 1.91-1.80 (m, 2H), 1.74-1.52 (m, 4H), 1.28-1.20 (m, 1H), 1.06-0.87 (m, 2H), 0.01 (s, 9H). LC-MS: 497 [M+1]$^+$, $t_R$=1.348 min.

Step 8:

To the solution of compound 16-7 (102 mg, 0.21 mmol) in 2.5 mL DCM was added dropwise 2.5 mL TFA. The resulting mixture was stirred at 20° C. for 2 h, then poured into 150 mL saturated aqueous sodium bicarbonate at 0° C. The mixture was adjusted to pH ~8.5 with solid sodium carbonate and extracted with DCM (80 mL×3). The combined organic layers were dried over anhydrous sodium sulfate, filtered and evaporated. The residue was purified by silica gel column (ethyl acetate:methanol=10:1+1% Et$_3$N) to give 38 mg product (yield 50%). The product was further purified by prep-HPLC to give 33 mg pure compound 16-8 as HCl salt. $^1$H NMR (300 MHz, CD$_3$OD): δ 7.91-7.81 (m, 1H), 7.07-6.91 (m, 2H), 4.85-4.40 (m, 3H), 4.00-3.91 (m, 1H), 3.71-3.59 (m, 1H), 3.47-3.25 (m, 2H), 3.15-2.85 (m, 4H), 2.76-2.62 (m, 1H), 1.99-1.72 (m, 5H), 1.41-1.37 (m, 3H). LC-MS: 367 [M+1]$^+$, $t_R$=0.395 min. HPLC: 95.4% at 214 nm, 95.1% at 254 nm, $t_R$=4.554 min.

Scheme 17

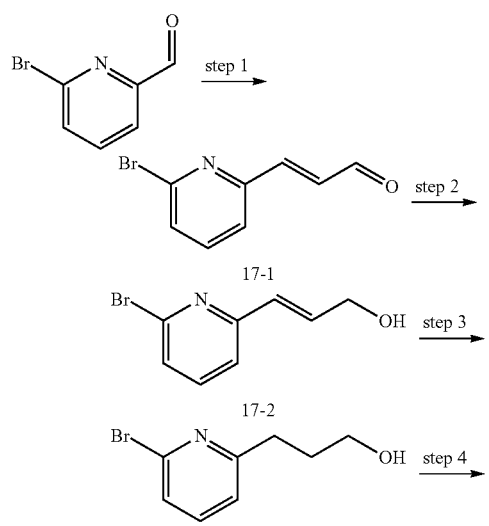

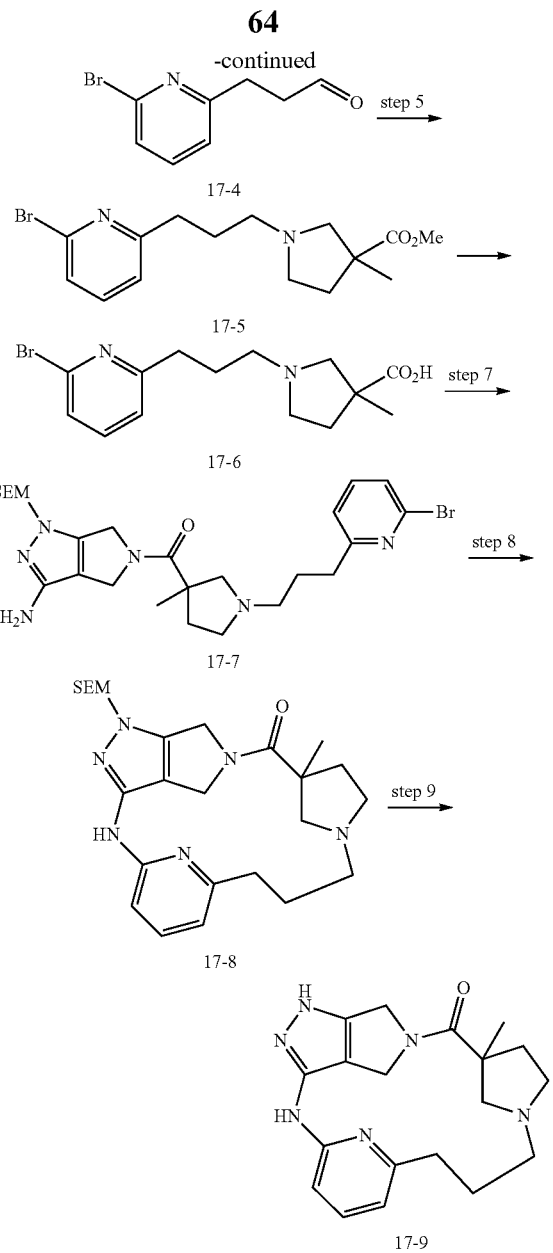

Step 1:

To the solution of 6-bromopyridine-2-carbaldehyde (9.3 g, 50 mmol) in 25 mL DMF was added (formylmethylene)triphenylphosphorane (15.2 g, 50 mmol). The resulting mixture was stirred at 20° C. for 20 h, then poured into 100 mL 0° C. saturated aqueous sodium bicarbonate and extracted with ethyl acetate (100 mL×2). The combined organic layers were dried over anhydrous sodium sulfate, filtered and evaporated. The residue was purified by silica gel column (petroleum ether/ethyl acetate=2:1) to give compound 17-1 (5.87 g, yield 55%). $^1$H NMR (300 MHz, CDCl$_3$): δ 9.77 (d, 1H, J=7.6 Hz), 7.63-7.40 (m, 3H), 7.13-7.05 (m, 1H). LC-MS: 212, 214 [M+1]$^+$, $t_R$=1.462 min.

Step 2:

To the 0° C. solution of compound 17-1 (2.2 g, 10.4 mmol) in 40 mL methanol was added portionwise NaBH$_4$ (1.97 g, 52 mmol). The resulting mixture was stirred at 20° C. for 2 h. Then poured into 100 mL 0° C. water, and evaporated to remove methanol. The resulting aqueous solution was extracted with DCM (50 mL×2). The combined organic layers were dried over anhydrous sodium sulfate, filtered and evaporated to give compound 17-2 (2.13 g, yield 96%). LC-MS: 214, 216 [M+1]$^+$, $t_R$=1.342 min.

Step 3:

To the solution of compound 17-2 (1.3 g, 6.1 mmol) in 20 mL ethanol was added 139 mg PtO$_2$, the resulting mixture was stirred under H$_2$ at 20° C. for 1.5 h. The reaction mixture was filtered and the filtrate was evaporated to give the residue which was purified by silica gel column (petroleum ether/ethyl acetate=1:1+1% Et$_3$N) to give compound 17-3 (1.08 g, yield 83%). $^1$H NMR (300 MHz, CDCl$_3$): δ 7.44 (t, 1H, J=7.7 Hz), 7.28 (d, 1H, J=7.7 Hz), 7.11 (d, 1H, J=7.5 Hz), 3.70-3.64 (m, 2H), 2.96 (br s, 1H), 2.86 (t, 2H, J=7.3 Hz), 2.02-1.91 (m, 2H). LC-MS: 216, 218 [M+1]$^+$, $t_R$=1.860 min.

Step 4:

To the solution of compound 17-3 (1.05 g, 4.86 mmol) in 60 mL DCM was added Dess-Martin periodinane (2.27 g, 5.35 mmol) and the resulting mixture was stirred 20° C. for 1 h. NaOH solution (1N, 40 mL) was added and stirred for 10 min. The organic layer was separated and washed with 40 mL 1 N NaOH and brine, dried over anhydrous sodium sulfate. The solution was filtered and evaporated and the residue was purified by silica gel column (petroleum ether/ethyl acetate=2:1) to give compound 17-4 (575 mg, yield 55%). $^1$H NMR (300 MHz, CDCl$_3$): δ 9.84 (d, 1H, J=0.9 Hz), 7.45 (t, 1H, J=7.8 Hz), 7.31 (d, 1H, J=7.9 Hz), 7.15 (d, 1H, J=7.5 Hz), 3.11-3.06 (m, 2H), 2.99-2.94 (m, 2H). LC-MS: 214, 216 [M+1]$^+$, $t_R$=1.356 min.

Step 5:

To a solution of compound 17-4 (575 mg, 3.2 mmol) and Et$_3$N (324 mg, 3.2 mmol) in 18 mL MeOH was added molecular sieves (1 g), 3-(6-bromopyridin-2-yl)propanal (570 mg, 2.66 mmol) and NaBH$_3$CN (334 mg 5.32 mmol). The resulting mixture was stirred under N$_2$ at 20° C. for 20 h, filtered and evaporated. The residue was purified by silica gel column (petroleum ether/ethyl acetate=1:1+1% Et$_3$N) to give compound 17-5 (545 mg, yield 60%). $^1$H NMR (300 MHz, CDCl$_3$): δ 7.43 (t, 1H, J=7.5 Hz), 7.29 (d, 1H, J=7.8 Hz), 7.10 (d, 1H, J=7.5 Hz), 3.68 (s, 3H), 2.97 (d, 1H, J=9.3 Hz), 2.79 (t, 2H, J=7.5 Hz), 2.61-2.56 (m, 2H), 2.47-2.34 (m, 4H), 1.94-1.84 (m, 2H), 1.67-1.58 (m, 1H), 1.33 (s, 3H). LC-MS: 341, 343 [M+1]$^+$, $t_R$=1.159 min.

Step 6:

To a solution of compound 17-5 (545 mg, 1.6 mmol) in 15 mL dioxane/15 mL water was added NaOH (513 mg, 12.8 mmol) and the resulting mixture was stirred at 15° C. for 20 h. Then the mixture was adjusted with pH to 7-8 and evaporated to dryness. The resulting solid was washed with methanol (30 mL) and filtered. The filtrate was evaporated to dryness to give compound 17-6 (801 mg, crude). LC-MS: 327, 329 [M+1]$^+$, $t_R$=1.190 min.

Step 7:

To a solution of the above acid 17-6, amine 1-7 (447 mg, 1.76 mmol), EDCI (368 mg, 1.92 mmol) and HOBT (259 mg, 1.92 mmol) in 40 mL DCM was added 1 mL DIEA and the resulting mixture was stirred at 10° C. for 20 h. The reaction mixture was quenched with 40 mL saturated aqueous NaHCO$_3$, and extracted with DCM (40 mL×2). The combined organic layers were dried over Na$_2$SO$_4$, filtered and evaporated. The residue was purified by silica gel column (ethyl acetate/methanol=20:1+1% Et$_3$N) to give compound 17-7 (720 mg, yield 80%). $^1$H NMR (300 MHz, CDCl$_3$): δ 7.43 (t, 1H, J=7.9 Hz), 7.29 (d, 1H, J=7.8 Hz), 7.11 (d, 1H, J=7.4 Hz), 5.3 (s, 2H), 4.60-4.42 (m, 4H), 3.93 (s, 2H), 3.60 (t, 2H, J=8.2 Hz), 3.01 (t, 1H, J=9.5 Hz), 2.84-2.75 (m, 3H), 2.60 (t, 1H, J=9.1 Hz), 2.50-2.41 (m, 4H), 1.98-1.87 (m, 2H), 1.83-1.68 (m, 2H), 1.42 (s, 3H), 0.93 (t, 2H, J=8.4 Hz), 0.01 (s, 9H). LC-MS: 563, 565 [M+1]$^+$, $t_R$=1.422 min.

Step 8:

Under N$_2$, compound 17-7 (670 mg, 1.19 mmol), Pd$_2$(dba)$_3$ (103 mg, 0.18 mmol), XANTPHOS (206 mg, 0.36 mmol) and tBuONa (161 mg, 1.68 mmol) was stirred in 350 mL toluene at 105° C. for 20 h. The mixture was cooled and quenched with 200 mL saturated aqueous sodium bicarbonate. The organic layer was separated and aqueous phase was extracted with ethyl acetate (150 mL×3). The combined organic layers were evaporated to dryness and co-evaporated with 20 mL toluene. The residue was purified by silica gel column (ethyl acetate+1% Et$_3$N) to give compound 17-8 (254 mg, yield 41.2%). $^1$H NMR (300 MHz, CDCl$_3$): δ 7.49 (t, 1H, J=7.6 Hz), 7.00 (s, 1H), 6.76 (d, 1H, J=7.4 Hz), 6.50 (d, 1H, J=8.0 Hz), 5.91-5.86 (m, 1H), 5.51-5.35 (m, 2H), 4.82-4.56 (m, 2H), 3.72-3.59 (m, 3H), 3.13-2.99 (m, 2H), 2.81-2.73 (m, 1H), 2.54-2.36 (m, 2H), 2.30-2.18 (m, 2H), 2.05-1.91 (m, 2H), 1.84-1.72 (m, 2H), 1.41 (s, 3H), 1.08-0.86 (m, 2H), 0.03 (s, 9H)

Step 9:

To the solution of compound 17-8 (102 mg, 0.21 mmol) in 10 mL DCM was added dropwise 2.5 mL TFA. The resulting mixture was stirred at 10° C. for 2 h, then poured into 100 mL 0° C. saturated aqueous sodium bicarbonate. Organic layer was separated and the aqueous layer was extracted with ethyl acetate (50 mL×3). Combined organic layers were dried over anhydrous sodium sulfate, filtered and evaporated. The resulting solid was washed with ethyl acetate and filtered to give compound 17-9 as a yellow powder (130 mg, yield 70%). $^1$H NMR (300 MHz, DMSO): δ 11.84 (br s, 1H), 9.23 (d, 1H, J=12.5 Hz), 7.50-7.30 (m, 1H), 6.56 (d, 1H, J=7.0 Hz), 5.63 (d, 1H, J=13.4 Hz), 4.81 (d, 1H, J=13.3 Hz), 4.61-4.29 (m, 2H), 3.70 (d, 1H, J=10.4 Hz), 2.97 (t, 1H, J=7.2 Hz), 2.85-2.75 (m, 1H), 2.64-2.55 (m, 1H), 2.42-2.33 (m, 2H), 2.27-2.18 (m, 1H), 2.12-1.98 (m, 1H), 1.85-1.71 (m, 2H), 1.66-1.53 (m, 2H), 1.26 (s, 3H). LC-MS: 353 [M+1]$^+$, $t_R$=0.284 min. HPLC: 98.8% at 214 nm, 99.2% at 254 nm, $t_R$=3.817 min.

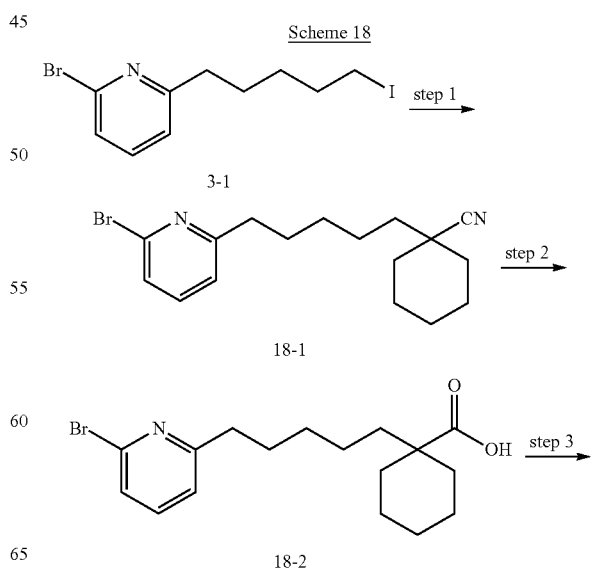

Scheme 18

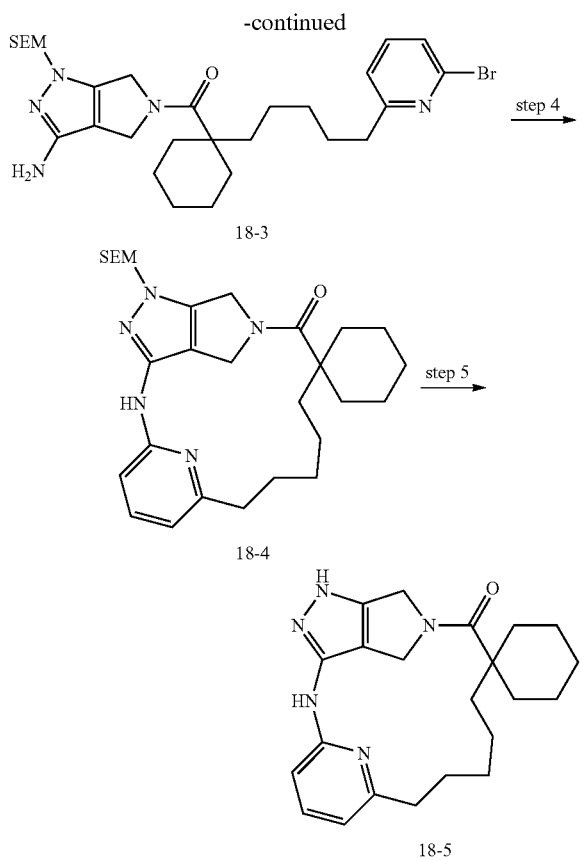

Step 1:

To a solution of diisopropyl amine (851 mg, 8.43 mmol) in THF (20 mL) at −78° C. was added n-BuLi (1.6 M in hexane, 4.79 mL, 7.66 mmol). The dry ice-acetone bath was removed after the addition. The reaction mixture was stirred for 10 min and then cooled to −78° C. A solution of cyclohexanecarbonitrile (835 mg, 7.66 mmol) in THF (5 mL) was added to the above prepared LDA solution dropwise at −78° C. and stirred at −78° C. for 15 minutes. Then a solution of compound 3-1 (904 mg, 2.55 mmol) in THF (5 mL) was added dropwise. The mixture was stirred at −78° C. for 30 minutes, then was poured into saturated aqueous NH$_4$Cl solution (100 mL). The organic layer was separated and the aqueous layer was extracted with ethyl acetate (70 mL×3). The combined organic layers were dried over anhydrous sodium sulfate, filtered and concentrated. The residue was purified by column chromatography on silica gel (petroleum ether/ethyl acetate=100:3) to give compound 18-1 (512 mg, 60% yield) as a colorless oil. $^1$HNMR (300 MHz, CDCl$_3$) δ 7.44 (t, 1H, J=7.7 Hz), 7.29 (d, 1H, J=7.9 Hz), 7.08 (d, 1H, J=7.5 Hz), 2.79-2.71 (m, 2H), 1.95 (d, 2H, J=13.0 Hz), 1.79-1.63 (m, 6H), 1.61-1.45 (m, 5H), 1.41-1.32 (m, 2H), 1.26-1.11 (m, 3H). LC-MS: 335, 337 [M+1]$^+$, t$_R$=1.835 min.

Step 2:

To a solution of compound 18-1 (512 mg, 1.53 mmol) in AcOH (20 mL) was added HBr (30 mL, 40%) at room temperature. The resulting reaction mixture was heated to 145° C. for 7 hours. Then it was cooled and basified with saturated aqueous NaHCO$_3$ solution to pH ~7 under ice water bath, and extracted with ethyl acetate (50 mL×3). The combined organic was dried over Na$_2$SO$_4$, concentrated under reduced pressure and purified by column chromatography on silica gel (petroleum ether/ethyl acetate=10:1) to give compound 18-2 (430 mg, 79% yield) as a pale yellow oil. $^1$H NMR (300 MHz, CDCl$_3$) δ 7.43 (t, 1H, J=7.7 Hz), 7.28 (d, 1H, J=7.6 Hz), 7.07 (d, 1H, J=7.4 Hz), 2.76-2.67 (m, 2H), 2.10-1.97 (m, 2H), 1.71-1.64 (m, 2H), 1.62-1.39 (m, 6H), 1.39-1.14 (m, 8H). LC-MS: 354, 356 [M+1]$^+$, t$_R$=1.702 min.

Step 3:

To a solution of compound 18-2 (390 mg, 1.1 mmol) and HATU (501.5 mg, 1.32 mmol) in dry DMF (10 mL) was added DIEA (426 mg, 3.3 mmol) at room temperature. After stirring for 1 h, amine 1-7 (348.7 mg, 1.36 mmol) was added and the resulting red solution was stirred overnight at 25° C. Then it was heated to 70° C. for 30 min. It was cooled to room temperature, diluted with ethyl acetate (100 mL), washed with water (50 mL×3), brine (50 mL), dried over Na$_2$SO4, concentrated under reduced pressure and purified by column chromatography on silica gel (petroleum ether/ethyl acetate=3:1~2:1+1% TEA) to give compound 18-3 (460 mg, 70.9% yield) as a yellow oil. $^1$H NMR (300 MHz, CDCl$_3$) δ 7.41 (t, 1H, J=7.7 Hz), 7.29-7.24 (m, 1H), 7.03 (d, 1H, J=7.0 Hz), 5.30 (s, 2H), 4.62-4.52 (m, 4H), 3.91 (s, 2H), 3.63-3.57 (m, 2H), 2.80 (s, 3H), 2.72-2.67 (m, 2H), 2.24-2.19 (m, 2H), 1.59-1.54 (m, 6H), 1.49-1.26 (m, 10H), 0.95-0.90 (m, 2H), 0.00 (s, 9H). LC-MS: 590, 592 [M+1]$^+$, t$_R$=1.866 min.

Step 4:

Under N$_2$, compound 18-3 (50 mg, 0.085 mmol), Pd$_2$(dba)$_3$ (7.3 mg, 0.013 mmol), XANTPHOS (14.7 mg, 0.025 mmol) and tBuONa (11.4 mg, 0.025 mmol) was stirred in 200 mL toluene at 105° C. for 6 h. The reaction mixture was cooled and quenched with 100 mL saturated aqueous sodium bicarbonate. The organic layer was separated and aqueous phase was extracted with ethyl acetate (30 mL×3). The combined organic layers were evaporated to dryness and co-evaporated with 20 mL toluene. The residue was purified by silica gel column (petroleum ether/ethyl acetate=1:2+1% Et$_3$N) to give compound 18-4 (35 mg, yield 81%). $^1$H NMR (300 MHz, CDCl$_3$) δ 7.48-7.42 (m, 1H), 6.77 (s, 1H), 6.66 (d, 1H, J=7.3 Hz), 6.50 (d, 1H, J=8.2 Hz), 5.42 (s, 2H), 4.97 (s, 2H), 4.71 (s, 2H), 3.68-3.60 (m, 2H), 2.69-2.60 (m, 2H), 2.12-2.06 (m, 2H), 1.81-1.73 (m, 4H), 1.58-1.433 (m, 12H), 1.02-0.93 (m, 2H), 0.03-0.01 (m, 9H). LC-MS: 510 [M+1]$^+$, t$_R$=3.424 min.

Step 5:

To a solution of compound 18-4 (200 mg, 0.39 mmol) in DCM (15 mL) was added TFA (3 mL). The resulting pale yellow solution was stirred for 2 hours at room temperature until the starting material was consumed completely by TLC. Then it was concentrated under reduced pressure and the residue was purified by prep-HPLC, compound 18-5 was obtained (50 mg, 26% yield) as the HCl salt. $^1$H NMR (300 MHz, CD$_3$OD) δ 7.89 (t, 1H, J=8.0 Hz), 6.98-6.89 (m, 2H), 4.64 (s, 2H), 4.53 (s, 2H), 2.71 (t, 2H, J=7.3 Hz), 1.94-1.90 (m, 2H), 1.75-1.61 (m, 3H), 1.41-1.39 (m, 13H). LC-MS: 380 [M+1]$^+$, t$_R$=4.799 min. HPLC: 96.68% at 214 nm, 98.97% at 254 nm, t$_R$=7.76 min.

Scheme 19

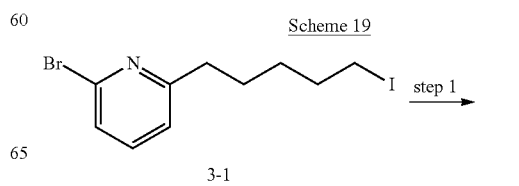

3-1

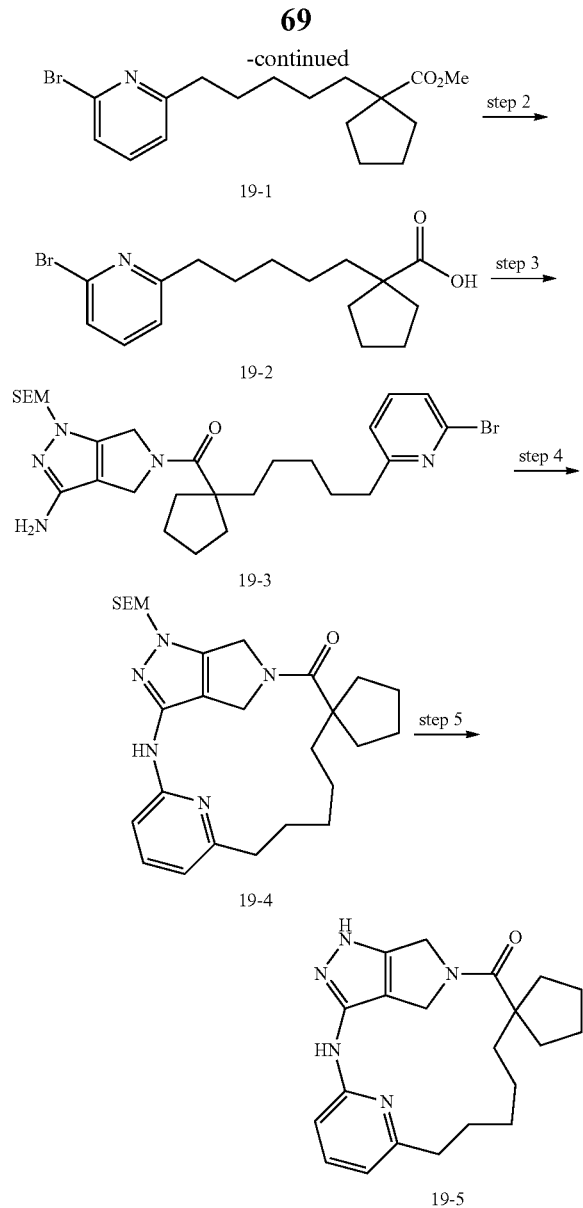

2.15-2.02 (m, 2H), 1.72-1.59 (m, 7H), 1.49-1.40 (m, 2H), 1.36-1.17 (m, 5H). LC-MS: 354, 356 [M+1]$^+$, $t_R$=3.190 min.

Step 2:

To a solution of compound 19-1 (2.0 g, 5.67 mmol) in 70 mL water/70 mL dioxane was added NaOH (2.3 g). The resulting mixture was stirred at 60° C. for 15 h. The mixture was evaporated to a small volume, 200 mL water was added and the mixture was adjusted to pH ~4 by HCl. The mixture was extracted with tBuOMe (200 mL×3) and combined organic layers were dried over anhydrous sodium sulfate, filtered and the filtrate was evaporated to give compound 19-2 (1.9 g, yield 99%).

$^1$H NMR (300 MHz, CDCl$_3$) δ 7.43 (t, 1H, J=7.7 Hz), 7.31-7.26 (m, 1H), 7.07 (d, 1H, J=7.5 Hz), 2.79-2.68 (m, 2H), 2.21-2.07 (m, 2H), 1.65-1.60 (m, 7H), 1.53-1.44 (m, 2H), 1.35-1.26 (m, 5H). LC-MS: 340, 342 [M+1]$^+$, $t_R$=2.959 min.

Step 3:

To a solution of compound 19-2 (500 mg, 1.475 mmol) in 25 mL DMF was added HATU (616 mg, 1.622 mmol) and DIEA (0.8 mL, 4.866 mmol). The resulting mixture was stirred at 0° C. for 0.5 h and amine 1-7 (412 mg, 1.622 mmol) was added and the resulting mixture was stirred at room temperature for 1.5 hours. The reaction mixture was cooled and evaporated to residue which was purified by silica gel column (petroleum ether/ethyl acetate=2:1+0.3% Et$_3$N) to give compound 19-3 (560 mg, yield 66%). $^1$H NMR (300 MHz, CDCl$_3$) δ 7.41 (t, 1H, J=7.7 Hz), 7.28 (s, 1H), 7.04 (d, 1H, J=7.6 Hz), 5.31 (s, 2H), 4.63-4.47 (m, 4H), 3.89 (s, 2H), 3.65-3.54 (m, 2H), 2.74-2.65 (m, 2H), 2.22 (s, 2H), 1.63-1.60 (m, 8H), 1.32-1.23 (m, 6H), 0.98-0.89 (m, 2H), 0.00 (s, 9H). LC-MS: 576, 578 [M+1]$^+$, $t_R$=1.794 min.

Step 4:

Under N$_2$, Compound 19-3 (560 mg, 0.974 mmol), Pd$_2$(dba)$_3$ (84 mg, 0.146 mmol), XANTPHOS (169 mg, 0.292 mmol) and tBuONa (131 mg, 1.363 mmol) was stirred in 280 mL toluene at 105° C. for 6 h. The reaction mixture was cooled and quenched with 200 mL saturated aqueous sodium bicarbonate. The organic layer was separated and aqueous phase was extracted with ethyl acetate (150 mL×3). Combined organic layers were evaporated to dryness and co-evaporated with 30 mL toluene. The residue was purified by silica gel column (petroleum ether/ethyl acetate=5:1 to 3:1+ 0.3% Et$_3$N) to give compound 19-4 (280 mg, yield 58%). $^1$H NMR (300 MHz, CDCl$_3$) δ 7.49-7.42 (m, 1H), 6.86 (s, 1H), 6.67 (d, 1H, J=7.3 Hz), 6.50 (d, 1H, J=8.2 Hz), 5.42 (s, 2H), 4.98 (s, 2H), 4.66 (s, 2H), 3.69-3.60 (m, 2H), 2.68-2.62 (m, 2H), 2.34-2.29 (m, 2H), 1.84-1.79 (m, 4H), 1.68-1.62 (m, 6H), 1.54-1.51 (m, 4H), 1.01-0.94 (m, 2H), 0.02 (s, 6H), 0.01 (s, 3H). LC-MS: 496 [M+1]$^+$, $t_R$=3.400 min.

Step 5:

To the solution of compound 19-4 (280 mg, 0.566 mmol) in 15 mL DCM was added dropwise 3 mL TFA. The resulting mixture was stirred at 15° C. for 2 h, then poured into 150 mL 0° C. saturated aqueous sodium bicarbonate. The reaction mixture was adjusted to pH ~9 with solid sodium carbonate. Organic layer was separated and the aqueous layer was extracted with DCM (100 mL×3). The combined organic layers were dried over anhydrous sodium sulfate, filtered and evaporated to give compound 19-5 (210 mg, yield 100%). $^1$H NMR (300 MHz, CD$_3$OD) δ 7.93-7.81 (m, 1H), 6.92 (dd, 2H, J$_1$=16.3, J$_2$=8.0 Hz), 4.60 (d, 4H, J=8.4 Hz), 2.71 (t, 2H, J=7.7 Hz), 2.17-2.09 (m, 2H), 1.69 (d, 4H, J=8.0 Hz), 1.57-1.54 (m, 6H), 1.36 (s, 4H). LC-MS: 366 [M+1]$^+$, $t_R$=4.541 min. HPLC: 97.6% at 214 nm, 98.6% at 254 nm, $t_R$=7.530 min.

Step 1:

To a solution of diisopropyl amine (4.23 g, 29.7 mmol) in THF (40 mL) at −78° C. was added n-BuLi (1.6 M in hexane, 17.1 mL, 27 mmol). The dry ice-acetone bath was removed after the addition. The reaction mixture was stirred for 10 min and then cooled to −78° C. A solution of cyclopentanecarboxylic acid methyl ester (3.4 g, 27 mmol) in THF (15 mL) was added to the above prepared LDA solution dropwise at −78° C. and stirred at −78° C. for 15 minutes. Then a solution of compound 3-1 (3.18 g, 9 mmol) and HMPA (1.62 mL, 9 mmol) in THF (35 mL) was added dropwise. After the mixture was stirred at −78° C. for 30 minutes, the reaction mixture was poured into saturated aqueous NH$_4$Cl solution (250 mL). The organic layer was separated and the aqueous layer was extracted with DCM (100 mL×3). The combined organic layers were dried over anhydrous sodium sulfate, filtered and concentrated. The residue was purified by column chromatography on silica gel (petroleum ether/ethyl acetate=50:1) to give compound 19-1 (2 g, 63%) as a yellow oil. $^1$H NMR (300 MHz, CDCl$_3$) δ 7.43 (t, 1H, J=7.7 Hz), 7.30-7.26 (m, 1H), 7.07 (d, 1H, J=7.5 Hz), 3.65 (s, 3H), 2.76-2.68 (m, 2H),

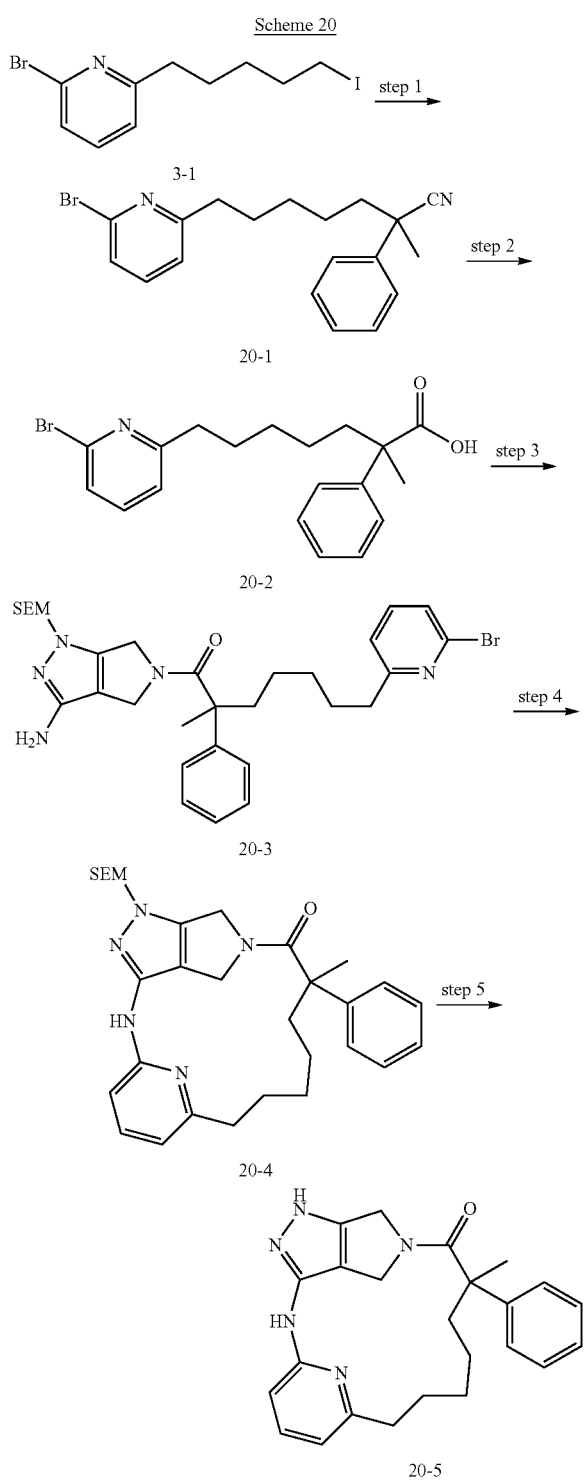

Scheme 20 mmol) and HMPA (506 mg, 2.82 mmol) in THF (5 mL) was added dropwise. After the mixture was stirred at −78° C. for 30 minutes, the reaction mixture was poured into saturated aqueous NH$_4$Cl solution (100 mL). The organic layer was separated and the aqueous layer was extracted with ethyl acetate (70 mL×3). The combined organic layers were dried over anhydrous sodium sulfate, filtered and concentrated. The residue was purified by column chromatography on silica gel (petroleum ether/ethyl acetate=50:1) to give compound 20-1 (900 mg, 89% yield) as a yellowish oil. $^1$H NMR (300 MHz, CDCl$_3$) δ 7.45-7.28 (m, 7H), 7.04 (d, 1H, J=7.4 Hz), 2.75-2.66 (m, 2H), 1.94-1.86 (m, 2H), 1.71 (s, 3H), 1.63-1.16 (m, 6H). LC-MS: 357, 359 [M+1]$^+$, $t_R$=1.777 min.

Step 2:

To a solution of compound 20-1 (900 mg, 2.52 mmol) in AcOH (5 mL) was added HBr (30 mL, 40%) at room temperature. The resulting reaction mixture was heated to 145° C. for 7 hours. Then it was cooled and basified with saturated aqueous NaHCO$_3$ solution to pH ~7 under ice water bath, extracted with ethyl acetate (70 mL×3). The combined organic layers was dried over Na$_2$SO$_4$, concentrated under reduced pressure and purified by column chromatography on silica gel (petroleum ether/ethyl acetate=7:1) to give compound 20-2 (746 mg, 78.9% yield) as a colorless oil. $^1$H NMR (300 MHz, CDCl$_3$) δ 7.40-7.28 (m, 6H), 7.25-7.20 (m, 1H), 7.04 (d, 1H, J=7.3 Hz), 2.76-2.67 (m, 2H), 2.04-1.85 (m, 2H), 1.63-1.73 (m, 2H), 1.57 (s, 3H), 1.35-1.20 (m, 4H). LC-MS: 376, 378 [M+1]$^+$, $t_R$=1.659 min.

Step 3:

To a solution of compound 20-2 (400 mg, 1.06 mmol) and HATU (485 mg, 1.28 mmol) in dry DMF (10 mL) was added DIEA (411 mg, 3.19 mmol) at room temperature. After stirring for 1 h, amine 1-7 (324.5 mg, 1.28 mmol) was added and the resulting red solution was stirred overnight at 25° C. Then it was heated to 70° C. for 30 min. It was cooled to room temperature, diluted with ethyl acetate (100 mL), washed with water (50 mL×3), brine (50 mL), dried over Na$_2$SO$_4$, concentrated under reduced pressure and purified by column chromatography on silica gel (petroleum ether/ethyl acetate=4:1~1:1+1% Et$_3$N) to give compound 20-3 (420 mg, 64.4% yield) as a yellow solid. $^1$H NMR (300 MHz, CDCl$_3$) δ 7.44-7.26 (m, 4H), 7.23-7.21 (m, 3H), 7.03 (d, 1H, J=7.4 Hz), 5.22 (d, 2H, J=9.0 Hz), 4.57-4.50 (m, 2H), 3.84 (s, 1H), 3.73-3.64 (m, 2H), 3.58-3.49 (m, 2H), 2.81 (s, 1H), 2.70 (t, 2H, J=7.6 Hz), 2.15-2.05 (m, 1H), 1.95-1.88 (m, 1H), 1.72-1.63 (m, 2H), 1.59 (s, 3H), 1.38-1.18 (m, 5H), 0.91-0.85 (m, 2H), 0.01-0.03 (m, 9H). LC-MS: 612, 614 [M+1]$^+$, $t_R$=1.803 min.

Step 4:

Under N$_2$, compound 20-3 (420 mg, 0.69 mmol), Pd$_2$(dba)$_3$ (59 mg, 0.10 mmol), XANTPHOS (119.8 mg, 0.21 mmol) and tBuONa (92.8 mg, 0.97 mmol) was stirred in 200 mL toluene at 105° C. for 6 h. Then the reaction mixture was cooled and quenched with 100 mL saturated aqueous sodium bicarbonate. The organic layer was separated and aqueous phase was extracted with ethyl acetate (100 mL×3). The combined organic layers were evaporated to dryness and co-evaporated with 20 mL toluene. The residue was purified by silica gel column (petroleum ether/ethyl acetate=1:2+1% Et$_3$N) to give compound 20-4 (95 mg, yield 26%). $^1$H NMR (300 MHz, CDCl$_3$) δ 7.43 (t, 1H, J=7.7 Hz), 7.34-7.28 (m, 4H), 7.20-7.18 (m, 1H), 6.63 (d, 1H, J=7.4 Hz), 6.53 (s, 1H), 6.45 (d, 1H, J=8.1 Hz), 5.45 (d, 1H, J=11.4 Hz), 5.28 (d, 1H, J=11.6 Hz), 5.04 (d, 1H, J=12.2 Hz), 4.88 (d, 1H, J=16.0 Hz), 4.57 (d, 1H, J=15.5 Hz), 3.80 (d, 1H, J=11.9 Hz), 3.64-3.50 (m, 2H), 2.81-2.73 (m, 2H), 2.62-2.53 (m, 1H), 1.87-1.70 (m, Step 1:

To a solution of diisopropyl amine (940 mg, 9.31 mmol) in THF (20 mL) at −78° C. was added n-BuLi (1.6 M in hexane, 5.29 mL, 8.46 mmol). The dry ice-acetone bath was removed after the addition. The reaction mixture was stirred for 10 min and then cooled to −78° C. A solution of 2-phenyl-propionitrile (1.11 g, 8.46 mmol) in THF (5 mL) was added to the above prepared LDA solution dropwise at −78° C. and stirred at −78° C. for 15 minutes. Then a solution of 3-1 (1 g, 2.82

5H), 1.59-1.42 (m, 6H), 0.97-0.86 (m, 2H), 0.00 (d, 9H, J=4.6 Hz). LC-MS: 532 [M+1]$^+$, $t_R$=3.329 min.

Step 5:

To a solution of compound 20-4 (120 mg, 0.23 mmol) in DCM (15 mL) was added TFA (3 mL). The resulting pale yellow solution was stirred for 2 hours at room temperature until the starting material was consumed completely by TLC. Then it was concentrated under reduced pressure and the residue was purified by prep-HPLC, compound 20-5 was obtained (28 mg, 24% yield) as HCl salt. $^1$H NMR (301 MHz, CD$_3$OD) δ 7.98 (t, 1H, J=7.9 Hz), 7.34-7.29 (m, 5H), 7.01 (t, 2H, J=7.9 Hz), 4.97 (s, 1H), 4.61 (d, 1H, J=15.5 Hz), 4.33 (d, 1H, J=12.9 Hz), 3.81 (d, 1H, J=12.7 Hz), 2.99-2.97 (m, 1H), 2.77-2.43 (m, 2H), 2.11-1.61 (m, 5H), 1.43-1.40 (m, 5H). LC-MS: 402 [M+1]$^+$, $t_R$=4.453 min. HPLC: 98.73% at 214 nm, 99.45% at 254 nm, $t_R$=5.91 min.

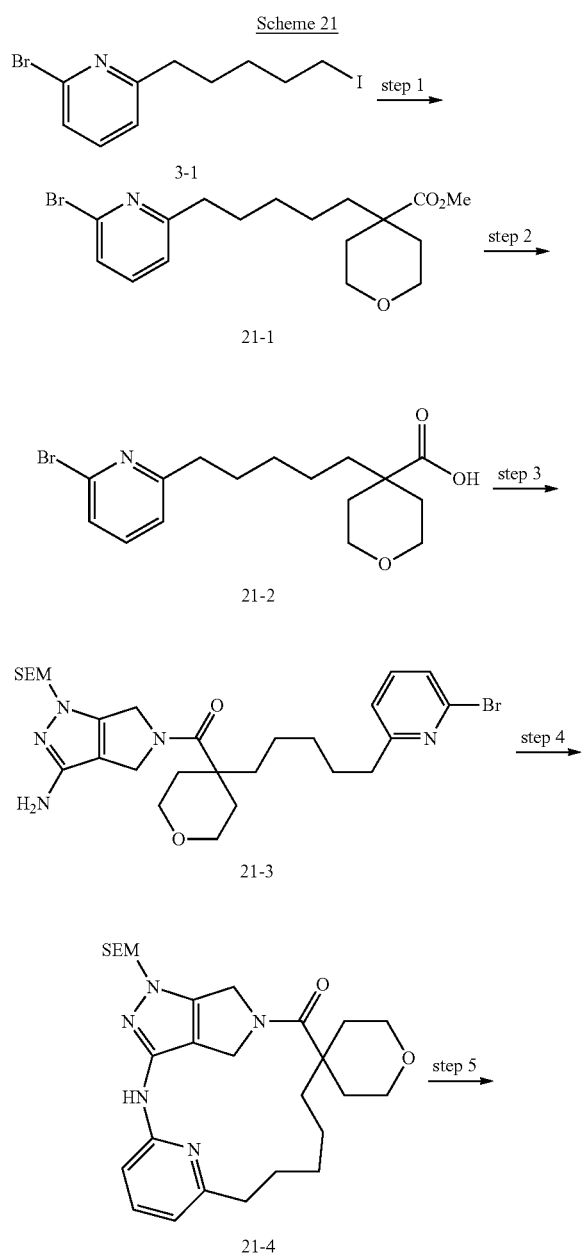

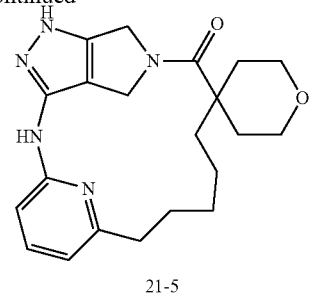

Step 1:

To a solution of diisopropyl amine (147 mg, 3.3 mmol) in THF (2 mL) at −78° C. was added n-BuLi (2.5 M in hexane, 1.2 mL, 3.0 mmol). The dry ice-acetone bath was removed after the addition. The reaction mixture was stirred for 10 min and then cooled to −78° C. A solution of tetrahydropyran-4-carboxylic acid methyl ester (190 mg, 3.0 mmol) in THF (1 mL) was added to the above prepared LDA solution dropwise at −78° C. and stirred at −78° C. for 15 minutes. Then a solution of compound 3-1 (155 mg, 1 mmol) and HMPA (0.08 mL, 1 mmol) in THF (2 mL) was added dropwise. After the mixture was stirred at −78° C. for 30 minutes, the reaction mixture was poured into saturated aqueous NH$_4$Cl solution (50 mL). The organic layer was separated and the aqueous layer was extracted with DCM (30 mL×3). The combined organic layers were dried over anhydrous sodium sulfate, filtered and concentrated. The residue was purified by column chromatography on silica gel (petroleum ether/ethyl acetate=10:1 to 6:1) to give compound 21-1 (95 mg, 59%) as a yellow oil. LC-MS: 370, 372 [M+1]$^+$, $t_R$=1.689 min.

Step 2:

To a solution of compound 21-1 (460 mg, 1.24 mmol) in 20 mL water/20 mL dioxane was added NaOH (497 mg). The resulting mixture was stirred at 60° C. for 15 h and then cooled down to room temperature. The mixture was evaporated to a small volume, water (20 mL) was added and the mixture was adjusted to pH ~4 by HCl. The mixture was extracted with tBuOMe (20 mL×3) and combined organic layers were dried over anhydrous sodium sulfate, filtered and the filtrate was evaporated to give compound 21-2 (410 mg, yield 93%). LC-MS: 356, 358 [M+1]$^+$, $t_R$=1.499 min.

Step 3:

To a solution of compound 21-2 (410 mg, 1.155 mmol) in 10 mL DCM was added HATU (527 mg, 1.386 mmol) and DIEA (0.72 mL, 3.465 mmol). The resulting mixture was stirred at 0° C. for 0.5 h and amine 1-7 (352 mg, 1.386 mmol) was added and the resulting mixture was stirred at 10° C. for 16 h, then refluxed for 8 h. The mixture was cooled and evaporated. The residue was purified by silica gel column (petroleum ether/ethyl acetate=1:1+1% Et$_3$N) to give compound 21-3 (380 mg, yield 47%). $^1$H NMR (300 MHz, CDCl$_3$) δ 7.42 (t, 1H, J=7.7 Hz), 7.29-7.23 (m, 1H), 7.04 (d, 1H, J=7.4 Hz), 5.34 (s, 2H), 4.60-4.58 (m, 4H), 4.23-3.92 (m, 1H), 3.85-3.57 (m, 7H), 2.77-2.66 (m, 2H), 2.26 (d, 2H, J=12.8 Hz), 1.74-1.50 (m, 7H), 1.29 (s, 5H), 1.00-0.89 (m, 2H), 0.01 (s, 9H). LC-MS: 592, 594 [M+1]$^+$, $t_R$=1.634 min.

Step 4:

Under N$_2$, compound 21-3 (330 mg, 0.558 mmol), Pd$_2$(dba)$_3$ (48.2 mg, 0.084 mmol), XANTPHOS (97 mg, 0.168 mmol) and tBuONa (75 mg, 0.782 mmol) was stirred in 165 mL toluene at 105° C. for 6 h. The reaction mixture was cooled and quenched with 100 mL saturated aqueous sodium bicarbonate. The organic layer was separated and aqueous phase was extracted with ethyl acetate (100 mL×3). Combined organic layers were evaporated to dryness and co-evaporated with 20 mL toluene. The residue was purified by silica gel column (petroleum ether/ethyl acetate=1:1+1% Et$_3$N) to give compound 21-4 (190 mg, yield 66.7%). $^1$H NMR (300 MHz, CDCl$_3$) δ 7.46 (t, 1H, J=7.7 Hz), 6.98-6.86 (m, 1H), 6.66 (d, 1H, J=7.3 Hz), 6.53 (d, 1H, J=8.1 Hz), 5.43 (s, 2H), 4.94 (s, 2H), 4.73 (s, 2H), 3.78-3.76 (m, 4H), 3.66-3.59 (m, 2H), 2.71-2.58 (m, 2H), 2.17 (d, 2H, J=13.6 Hz), 1.88-1.42 (m, 12H), 1.01-0.90 (m, 2H), 0.01 (d, 9H, J=3.5 Hz). LC-MS: 512 [M+1]$^+$, $t_R$=1.724 min.

Step 5:

To the solution of compound 21-4 (210 mg, 0.41 mmol) in 10 mL DCM was added dropwise 3 mL TFA. The resulting mixture was stirred at 15° C. for 2 h, then poured into 150 mL 0° C. saturated aqueous sodium bicarbonate and pH was adjusted to 9 with solid sodium carbonate. Organic layer was separated and the aqueous layer was extracted with DCM (100 mL×3). Combined organic layers were dried over anhydrous sodium sulfate, filtered and evaporated to give compound 21-5 (160 mg, yield 100%). A portion of the product (100 mg) was further purified by prep-HPLC to give 50 mg of pure 21-5 as HCl salt. $^1$H NMR (300 MHz, CD$_3$OD) δ 7.89 (dd, 1H, J$_1$=8.7 Hz, J$_2$=7.4 Hz), 6.98-6.89 (m, 2H), 4.67 (s, 2H), 4.52 (s, 2H), 3.64-3.58 (m, 4H), 2.71 (t, 2H, J=7.6 Hz), 2.04 (d, 2H, J=13.7 Hz), 1.76-1.66 (m, 4H), 1.54-1.20 (m, 7H). LC-MS: 382 [M+1]$^+$, $t_R$=3.462 min. HPLC: 100% at 214 nm, 100% at 254 nm, $t_R$=5.956 min.

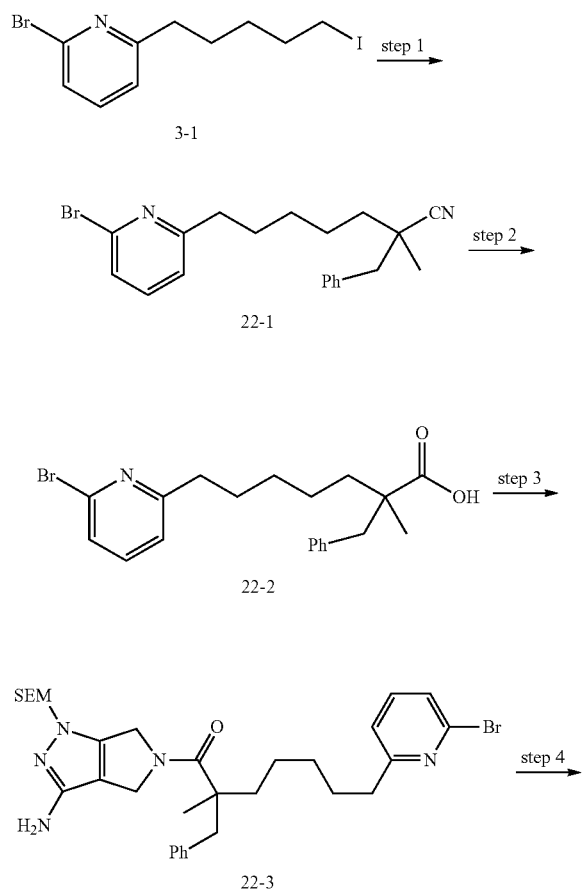

Scheme 22

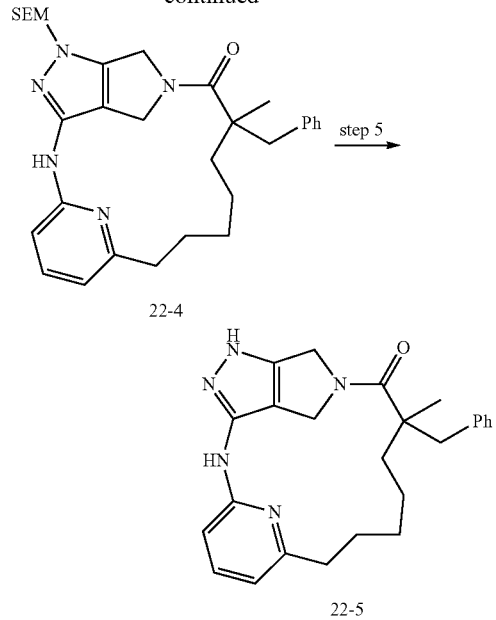

Step 1:

To a solution of diisopropyl amine (0.94 mL, 6.6 mmol) in THF (12 mL) at −78° C. was added n-BuLi (2.5 M in hexane, 3.8 mL, 6.0 mmol). The dry ice-acetone bath was removed after the addition. The reaction mixture was stirred for 10 min and then cooled to −78° C. A solution of 2-methyl-3-phenyl-propionic acid methyl ester (1.02 g, 6.0 mmol) in THF (4 mL) was added to the above prepared LDA solution dropwise at −78° C. and stirred at −78° C. for 15 minutes. Then a solution of compound 3-1 (706 mg, 2 mmol) and HMPA (0.36 mL, 2 mmol) in THF (4 mL) was added dropwise. After the mixture was stirred at −78° C. for 30 minutes, the reaction mixture was poured into saturated aqueous NH$_4$Cl solution (100 mL). The organic layer was separated and the aqueous layer was extracted with DCM (50 mL×3). The combined organic layers were dried over anhydrous sodium sulfate, filtered and concentrated. The residue was purified by column chromatography on silica gel (petroleum ether/ethyl acetate=50:1) to give compound 22-1 (650 mg, 80%) as a yellowish oil. $^1$H NMR (300 MHz, CDCl$_3$) δ 7.44 (t, 1H, J=7.7 Hz), 7.30-7.19 (m, 5H), 7.07 (d, 2H, J=7.2 Hz), 3.65 (s, 3H), 3.01 (d, 1H, J=13.2 Hz), 2.77-2.66 (m, 3H), 1.77-1.66 (m, 3H), 1.44-1.20 (m, 5H), 1.08 (s, 3H). LC-MS: 404, 406 [M+1]$^+$, $t_R$=1.933 min.

Step 2:

To a solution of compound 22-1 (650 mg, 1.61 mmol) in 25 mL water/25 ml dioxane was added NaOH (613 mg). The resulting mixture was stirred at 60° C. for 40 h then evaporated to a small volume, 20 mL water was added and the mixture was adjusted to pH ~4 with HCl. The mixture was extracted with tBuOMe (20 mL×3) and combined organic layers were dried over anhydrous sodium sulfate, filtered and the filtrate was evaporated to give compound 22-2 (509 mg, yield 81%). LC-MS: 390, 392 [M+1]$^+$, $t_R$=1.734 min.

Step 3:

To a solution of compound 22-2 (509 mg, 1.305 mmol) in 15 mL DCM was added HATU (597 mg, 1.57 mmol) and DIEA (0.69 ml, 3.92 mmol). The resulting mixture was stirred at 0° C. for 0.5 h and amine 1-7 (665 mg, 2.61 mmol) was added and the resulting mixture was stirred at 10° C. for 16 h, then refluxed for 8 h. The reaction mixture was cooled and evaporated. The residue was purified by silica gel column (petroleum ether/ethyl acetate=1:1+1% Et$_3$N) to give compound 22-3 (620 mg, yield 76%). $^1$H NMR (300 MHz, CDCl$_3$): δ 7.41 (t, 1H, J=7.6 Hz), 7.28-7.04 (m, 7H), 5.29 (s, 2H), 4.61-4.25 (m, 4H), 3.99-3.82 (m, 2H), 3.59 (t, 2H, J=8.3 Hz), 3.18-3.09 (m, 1H), 2.82-2.67 (m, 11H), 2.02-1.91 (m, 1H), 1.75-1.65 (m, 2H), 1.44-1.28 (m, 7H), 0.96-0.88 (m, 2H), 0.00 (s, 9H). LC-MS: 626, 628 [M+1]$^+$, t$_R$=1.828 min.

Step 4:

Under N$_2$, compound 22-3 (545 mg, 0.87 mmol), Pd$_2$(dba)$_3$ (75 mg, 0.13 mmol), XANTPHOS (150 mg, 0.26 mmol) and tBuONa (117 mg 1.22 mmol) was stirred in 380 mL toluene at 105° C. for 5.5 h. Then the reaction was cooled and quenched with 100 mL saturated aqueous sodium bicarbonate. The organic layer was separated and aqueous phase was extracted with ethyl acetate (100 mL×3). Combined organic layers were evaporated to dryness and co-evaporated with 20 mL toluene. The residue was purified by silica gel column (petroleum ether/ethyl acetate=1:1+1% Et$_3$N) to give compound 22-4 (274 mg, yield 47%). $^1$H NMR (300 MHz, CDCl$_3$): δ 7.44 (t, 1H, J=7.8 Hz), 7.22-7.08 (m, 5H), 6.67-6.45 (m, 3H), 5.46-5.31 (m, 2H), 4.94-4.56 (m, 3H), 4.27 (d, 1H, J=12.4 Hz), 3.64-3.57 (m, 2H), 2.94-2.51 (m, 4H), 2.09-2.01 (m, 1H), 1.80-1.38 (m, 8H), 1.10-0.78 (m, 3H), 0.01 (s, 9H). LC-MS: 546 [M+1]$^+$, t$_R$=1.943 min.

Step 5:

To the solution of compound 22-4 (260 mg, 0.48 mmol) in 10 mL DCM was added dropwise 2.5 mL TFA. The resulting mixture was stirred at 15° C. for 2 h, then poured into 150 mL 0° C. saturated aqueous sodium bicarbonate and pH was adjusted to 9 with solid sodium carbonate. Organic layer was separated and the aqueous layer was extracted with DCM (100 mL×3). Combined organic layers were dried over anhydrous sodium sulfate, filtered and evaporated to give compound 22-5 (209 mg, yield 100%) as HCl salt. $^1$H NMR (300 MHz, CD$_3$OD): δ 7.99 (d, 1H, J=8.06 Hz), 7.23-7.00 (m, 7H), 4.83-4.78 (m, 1H), 4.58-4.53 (m, 1H), 4.29-4.24 (m, 1H), 3.85-3.78 (m, 1H), 2.97-2.71 (m, 4H), 2.02-1.78 (m, 3H), 1.63-1.43 (m, 3H), 1.28 (s, 3H), 1.26-0.99 (m, 2H). LC-MS: 416 [M+1]$^+$, t$_R$=4.768 min. HPLC: 98.1% at 214 nm, 98.7% at 254 nm, t$_R$=5.73 min.

JAK Assay Information

Determination of IC$_{50}$ of Janus Kinase (JAK) inhibition:

Enzymes and peptide substrate used are described below:
JAK1: Recombinant human kinase domain (866-1154) from Invitrogen (Cat #PV4774)
JAK3: Recombinant human kinase domain (810-1124) made in house by Roche Palo Alto
JAK2: Recombinant human kinase domain (808-1132) from Millipore (Cat #14-640)
Substrate: N-terminally biotinylated 14-mer peptide derived from activation loop of JAK1 with sequence of the peptide substrate: Biotin-KAIETDKEYYTVKD Assay conditions used are described below:
Assay Buffer: JAK Kinase Buffer: 50 mM Hepes [pH 7.2], 10 mM MgCl$_2$, 1 mM DTT, 1 mg/ml BSA. The assay is carried out in this buffer.
Assay Format: The kinase activity of all three JAK kinases is measured using a radioactive, end-point assay and with trace amounts of $^{33}$P-ATP. The assays are carried out in 96-well polypropylene plates.

Experimental Method:

All concentrations are final in the reaction mixture and all incubations are carried at room temperature. Assay steps are described below:

1) Compounds are serially diluted in 100% DMSO typically at a 10× starting concentration of 1 mM. Final concentration of DMSO in the reaction is 10%.
2) Compounds are preincubated with enzyme (0.1 nM JAK3, 1 nM JAK2, 5 nM JAK1) for 10 minutes.
3) Reactions are initiated by the addition of a cocktail of the two substrates (ATP and peptide premixed in the JAK Kinase Buffer). In the JAK1/JAK2/JAK3 assays, ATP and the peptide are used at concentrations of 1.5 uM and 50 uM, respectively. The duration of the assay for JAK2 and JAK3 is 20 minutes. JAK1 assay is carried out for 45 minutes. With all three enzymes, reactions are terminated by the addition of 0.5M EDTA to a final concentration of 100 mM.
4) 25 ul of terminated reactions are transferred to 150 ul of a 7.5% (v/v) slurry of streptavidin-coated sepharose beads in MgCl$_2$- and CaCl$_2$-free 1× Phosphate Buffered Saline containing 50 mM of EDTA in 96-well, 1.2 um MultiScreen-BV filter plates.
5) After a 30-minute incubation, the beads are washed under vacuum with the following buffers:
   a. 3 to 4 washes with 200 ul of 2M NaCl.
   b. 3 to 4 washes with 200 ul of 2M NaCl plus 1% (v/v) phosphoric acid.
   c. 1 wash with water.
6) Washed plates are dried in a 60° C. oven for between 1 to 2 hours.
7) 70 ul of Microscint 20 scintillation fluid is added to each well of filter plates and after at least 30 minutes of incubation, radioactive counts are measured in a Perkin Elmer microplate scintillation counter.

Representative IC$_{50}$ (μM) results are in Table II below:

TABLE II

| Compound | JAK3 Enzyme IC50 (μM) |
|---|---|
| I-1 | 0.915 |
| I-2 | 0.795 |
| I-3 | >10 |
| I-4 | 0.280 |
| I-5 | 0.530 |
| I-6 | 0.502 |
| I-7 | 0.811 |
| I-8 | 1.04 |
| I-9 | >3 |
| I-10 | 0.343 |
| I-11 | 0.487 |
| I-12 | 0.0426 |
| I-13 | 0.0928 |
| I-14 | 4.21 |
| I-15 | 0.444 |
| I-16 | >1 |
| I-17 | >1 |
| I-18 | 10 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula I

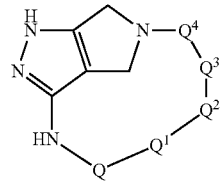

wherein:

Q is phenyl or heteroaryl, optionally substituted with one or more Q';

Q' is halogen, hydroxy, lower alkyl, lower haloalkyl, lower hydroxyalkyl, amino, lower alkoxy, or lower haloalkoxy;

$Q^1$ is O or $C(Q^{1'})_2$;

each $Q^{1'}$ is independently H, halogen, hydroxy, lower alkyl, lower haloalkyl, lower hydroxyalkyl, amino, lower alkoxy, or lower haloalkoxy;

$Q^2$ is $(C(Q^{2'})_2)_n$, $N(Q^{2''})$, or $C(Q^{2'})_2C(Q^{2'})_2$;

each $Q^{2'}$ is independently H, halogen, hydroxy, lower alkyl, lower haloalkyl, lower hydroxyalkyl, amino, lower alkoxy, or lower haloalkoxy;

or $Q^{2''}$ and $Q^{3'}$ together form a heterocyclic ring;

n is 2, 3, 4, or 5;

$Q^3$ is O, $N(Q^{3'})$, $C(Q^{3'})_2$, carbocyclyl, or heterocyclyl;

each $Q^{3'}$ is independently H, halogen, hydroxy, lower alkyl, lower haloalkyl, lower hydroxyalkyl, amino, lower alkoxy, phenyl, benzyl, or lower haloalkoxy;

or both $Q^{3'}$ together form a spirocyclic carbocyclic or heterocyclic ring; and $Q^4$ is C(=O) or S(=O)$_2$;

with the proviso that when $Q^2$ is $N(Q^{2''})$, then $Q^3$ is not $N(Q^{3'})$;

or a pharmaceutically acceptable salt thereof.

2. The compound of claim 1, wherein Q is pyridine.

3. The compound of claim 2, wherein $Q^4$ is C(=O).

4. The compound of claim 3, wherein $Q^3$ is $C(CH_3)_2$ or $C(CH_3)(CH_2CH_3)$.

5. The compound of claim 4, wherein $Q^1$ is $CH_2$.

6. The compound of claim 5, wherein $Q^2$ is $C(CH_2)n$.

7. The compound of claim 6, wherein n is 2.

8. The compound of claim 6, wherein n is 3.

9. The compound of claim 6, wherein n is 4.

10. The compound of claim 4, wherein $Q^1$ is O.

11. The compound of claim 10, wherein $Q^2$ is $C(CH_2)n$.

12. The compound of claim 11, wherein n is 3.

13. The compound of claim 11, wherein n is 4.

14. A compound of Formula II

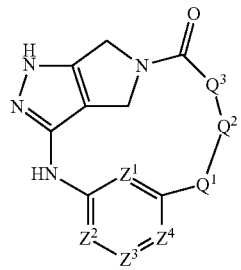

wherein:

each of $Z^1$, $Z^2$, $Z^3$, and $Z^4$ are independently C(Z') or N;

each Z' is independently H, halogen, hydroxy, lower alkyl, lower haloalkyl, lower hydroxyalkyl, amino, lower alkoxy, or lower haloalkoxy;

$Q^1$ is O or $C(Q^{1'})_2$;

each $Q^{1'}$ is independently H, halogen, hydroxy, lower alkyl, lower haloalkyl, lower hydroxyalkyl, amino, lower alkoxy, or lower haloalkoxy; $Q^2$ is $(C(Q^{2'})_2)_n$, $N(Q^{2''})$, or $C(Q^{2'})_2C(Q^{2'})_2$;

each $Q^{2'}$ is independently H, halogen, hydroxy, lower alkyl, lower haloalkyl, lower hydroxyalkyl, amino, lower alkoxy, or lower haloalkoxy;

or $Q^{2''}$ and $Q^{3'}$ together form a heterocyclic ring;

n is 2, 3, 4, or 5;

$Q^3$ is O, $N(Q^{3'})$, $C(Q^{3'})_2$, carbocyclyl, or heterocyclyl;

each $Q^{3'}$ is independently H, halogen, hydroxy, lower alkyl, lower haloalkyl, lower hydroxyalkyl, amino, lower alkoxy, phenyl, benzyl, or lower haloalkoxy;

or both $Q^{3'}$ together form a spirocyclic carbocyclic or heterocyclic ring; and with the proviso that when $Q^2$ is $N(Q^{2''})$, then $Q^3$ is not $N(Q^{3'})$;

or a pharmaceutically acceptable salt thereof.

15. The compound of claim 14, wherein $Z^1$ is N, $Z^2$ is CH, $Z^3$ is CH, and $Z^4$ is CH.

16. The compound of claim 15, wherein $Q^3$ is $C(CH_3)_2$ or $C(CH_3)(CH_2CH_3)$.

17. The compound of claim 16, wherein $Q^1$ is $CH_2$.

18. The compound of claim 17, wherein $Q^2$ is $C(CH_2)n$.

19. The compound of claim 18, wherein n is 2.

20. The compound of claim 18, wherein n is 3.

21. The compound of claim 18, wherein n is 4.

22. The compound of claim 16, wherein $Q^1$ is O.

23. The compound of claim 22, wherein $Q^2$ is $C(CH_2)n$.

24. The compound of claim 23, wherein n is 3.

25. The compound of claim 23, wherein n is 4.

26. A compound selected from the group consisting of:

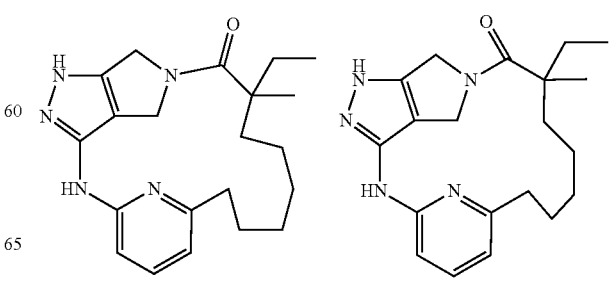

81
-continued
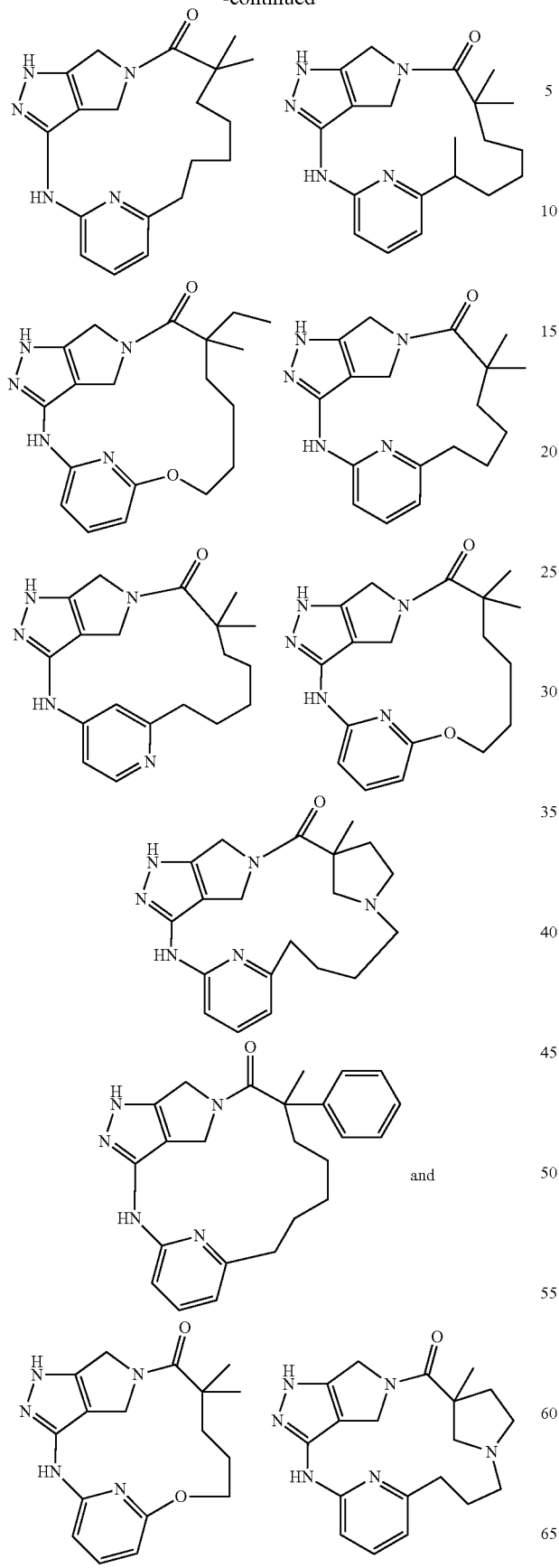
and
82
-continued
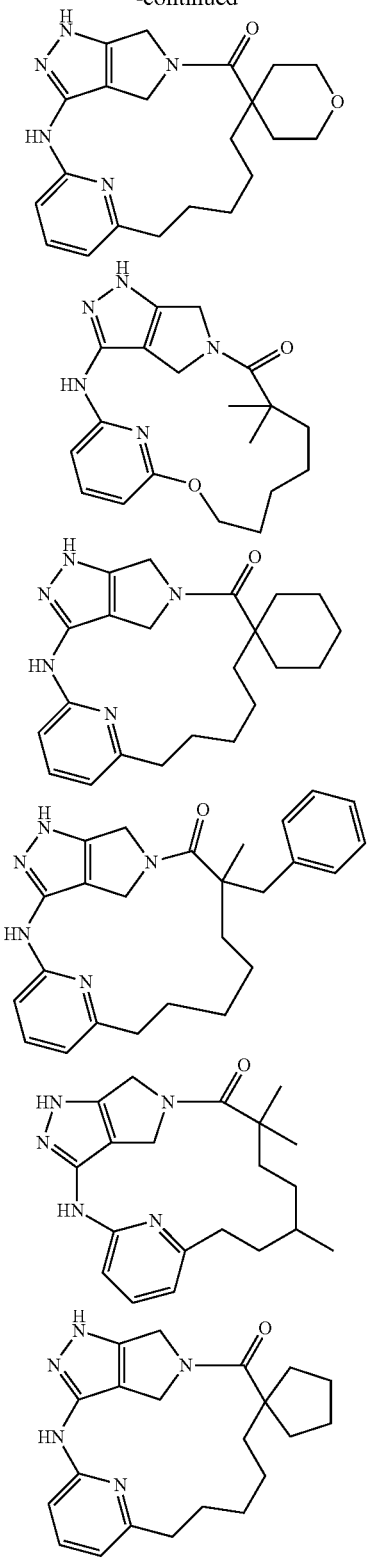
27. A pharmaceutical composition comprising the compound of claim 1, admixed with at least one pharmaceutically acceptable carrier, excipient or diluent.
28. The pharmaceutical composition of claim 27, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

29. A method for treating rheumatoid arthritis comprising administering to a patient in need thereof a therapeutically effective amount of the compound of claim 1.

30. A method for treating asthma comprising administering to a patient in need thereof a therapeutically effective amount of the compound of claim 1.

* * * * *